United States Patent
Sato et al.

(10) Patent No.: US 11,530,427 B2
(45) Date of Patent: Dec. 20, 2022

(54) USES OF SURFACTANTS IN STARCH PROCESSING

(71) Applicants: BASF SE, Ludwigshafen (DE); BASF Enzymes LLC, San Diego, CA (US)

(72) Inventors: Yukiko Sato, San Diego, CA (US); Frank Reinhold, Wyandotte, MI (US); Justin Andrew Bordley, Charlotte, NC (US); Joseph P Borst, Wyandotte, MI (US); Matthew Gerard Lyon, Wyandotte, MI (US); Christopher Paul Myers, Wyandotte, MI (US); Katrina Marie Knauer, Tarrytown, NY (US)

(73) Assignees: BASF SE, Ludwigshafen am Rhein (DE); BASF Enzymes LLC, San Diego, CA (US)

( * ) Notice: Subject to any disclaimer, the term of this patent is extended or adjusted under 35 U.S.C. 154(b) by 0 days.

(21) Appl. No.: 17/050,054

(22) PCT Filed: May 23, 2019

(86) PCT No.: PCT/US2019/033653
§ 371 (c)(1),
(2) Date: Oct. 23, 2020

(87) PCT Pub. No.: WO2019/226845
PCT Pub. Date: Nov. 28, 2019

(65) Prior Publication Data
US 2021/0207176 A1 Jul. 8, 2021

Related U.S. Application Data

(60) Provisional application No. 62/676,477, filed on May 25, 2018.

(51) Int. Cl.
*C12P 7/06* (2006.01)
*C12P 19/14* (2006.01)

(52) U.S. Cl.
CPC ............... *C12P 7/06* (2013.01); *C12P 19/14* (2013.01); *C12Y 302/01001* (2013.01); *C12Y 302/01002* (2013.01); *C12Y 302/01003* (2013.01)

(58) Field of Classification Search
CPC .... C12P 19/14; C12P 7/06; C12Y 302/01003; C12Y 302/01002; C12Y 302/01001; Y02E 50/10
See application file for complete search history.

(56) References Cited

U.S. PATENT DOCUMENTS

| 7,273,740 | B2 * | 9/2007 | Callen | A21D 8/042 536/23.4 |
| 7,407,677 | B2 * | 8/2008 | Callen | C12P 19/14 435/254.2 |
| 11,034,923 | B2 * | 6/2021 | Zack | C12F 3/10 |

FOREIGN PATENT DOCUMENTS

DE 102014225475 A1 6/2016

OTHER PUBLICATIONS

Nair et al., Bioconversion of Cellulo-Starch Waste from Cassava Starch Industries for Ethanol Production: Pretreatment Techniques and Improved Enzyme Systems. Indust. Biotechnol., 2012, vol. 8(5): 300-308. (Year: 2012).*
Rodriguez et al., Modification of the activity of an α-amylase from Bacillus licheniformis by several surfactants. Electronic J. Biotechnol., 2006, vol. 9(5): 567-571. (Year: 2006).*
Steeples S., Rheological Characterization of Four Kansas Hard Red Winter Wheat Flour-Water Dough Systems. Master's Thesis, 2010, Kansas State Univ., Manhattan, Kansas, pp. 1-106. (Year: 2010).*
Steertegem et al., Combined impact of Bacillus stearothermophilus maltogenic alpha-amylase and surfactants on starch pasting and gelation properties. Food Chem., 2013, vol. 139: 1113-1120. (Year: 2013).*
Hoshino, et al., "Enhancement of enzymatic catalysis of Bacillus amyloliquefaciens αamylase by nonionic surfactant micelles", Journal of Surfactants and Detergents, vol. 6, Issue 4, Oct. 2003, pp. 299-303.
International Search Report for PCT Patent Application No. PCT/US2019/033653, dated Aug. 22, 2019, 5 pages.
Krister Holmberg, "Interactions between surfactants and hydrolytic enzymes", Colloids and Surfaces B: Biointerfaces, vol. 168, Aug. 1, 2018, pp. 169-177.
Lou, et al., "Nonionic surfactants enhanced enzymatic hydrolysis of cellulose by reducing cellulase deactivation caused by shear force and air-liquid interface", Bioresource Technology, vol. 249, Feb. 2018, pp. 1-8.
Needleman, et al., "A general method applicable to the search for similarities in the amino acid sequence of two proteins", Journal of Molecular Biology, vol. 48, Issue 3, Mar. 28, 1970, pp. 443-453.
Simair, et al., "Amylase Production from Thermophilic *Bacillus* sp. BCC 021-50 Isolated from a Marine Environment", Fermentation, vol. 3, Issue 2, Jun. 1, 2017, pp. 1-12.

(Continued)

*Primary Examiner* — Ganapathirama Raghu
(74) *Attorney, Agent, or Firm* — DLA Piper LLP (US)

(57) ABSTRACT

Disclosed herein include methods of reducing the viscosity of a starch slurry during starch processing by the addition of one or more surfactants and one or more amylases. In some embodiments, the unexpected reduction in slurry viscosity results in a surprising increase in corn oil recovery, reduction in residual starch, and increased fermentation rate.

19 Claims, 4 Drawing Sheets
Specification includes a Sequence Listing.

(56) References Cited

OTHER PUBLICATIONS

Vernon-Carter, et al., "In vitro digestibility of normal and waxy corn starch is modified by the addition of Tween 80", International Journal of Biological Macromolecules, vol. 116, Sep. 2018, pp. 715-720.

Wu, et al., "Purification and biochemical characterization of a thermostable and acid-stable alpha-amylase from Bacillus licheniformis B4-423", International Journal of Biological Macromolecules, vol. 109, Apr. 1, 2018, pp. 329-337.

* cited by examiner

SEQUENCE LISTING

```
<160> NUMBER OF SEQ ID NOS: 51

<210> SEQ ID NO 1
<211> LENGTH: 436
<212> TYPE: PRT
<213> ORGANISM: Artificial Sequence
<220> FEATURE:
<223> OTHER INFORMATION: Synthetic protein

<400> SEQUENCE: 1

Met Ala Lys Tyr Ser Glu Leu Glu Lys Gly Gly Val Ile Met Gln Ala
1               5                   10                  15

Phe Tyr Trp Asp Val Pro Ser Gly Gly Ile Trp Trp Asp Thr Ile Arg
            20                  25                  30

Gln Lys Ile Pro Glu Trp Tyr Asp Ala Gly Ile Ser Ala Ile Trp Ile
        35                  40                  45

Pro Pro Ala Ser Lys Gly Met Gly Gly Ala Tyr Ser Met Gly Tyr Asp
    50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Met Lys Val Ile Ala Asp Ile Val Ile Asn His
```

```
            100                 105                 110
Arg Ala Gly Gly Asp Leu Glu Trp Asn Pro Phe Val Asn Asp Tyr Thr
        115                 120                 125

Trp Thr Asp Phe Ser Lys Val Ala Ser Gly Lys Tyr Thr Ala Asn Tyr
        130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
        180                 185                 190

Ile Asp Ala Trp Arg Phe Asp Tyr Val Lys Gly Tyr Ala Pro Trp Val
        195                 200                 205

Val Lys Asp Trp Leu Asn Trp Trp Gly Gly Trp Ala Val Gly Glu Tyr
        210                 215                 220

Trp Asp Thr Asn Val Asp Ala Val Leu Asn Trp Ala Tyr Ser Ser Gly
225                 230                 235                 240

Ala Lys Val Phe Asp Phe Ala Leu Tyr Tyr Lys Met Asp Glu Ala Phe
                245                 250                 255

Asp Asn Lys Asn Ile Pro Ala Leu Val Ser Ala Leu Gln Asn Gly Gln
                260                 265                 270

Thr Val Val Ser Arg Asp Pro Phe Lys Ala Val Thr Phe Val Ala Asn
        275                 280                 285

His Asp Thr Asp Ile Ile Trp Asn Lys Tyr Pro Ala Tyr Ala Phe Ile
        290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Glu Asn
                325                 330                 335

Leu Ala Gly Gly Ser Thr Asp Ile Val Tyr Tyr Asp Asn Asp Glu Leu
                340                 345                 350

Ile Phe Val Arg Asn Gly Tyr Gly Asp Lys Pro Gly Leu Ile Thr Tyr
        355                 360                 365

Ile Asn Leu Gly Ser Ser Lys Ala Gly Arg Trp Val Tyr Val Pro Lys
        370                 375                 380

Phe Ala Gly Ala Cys Ile His Glu Tyr Thr Gly Asn Leu Gly Gly Trp
385                 390                 395                 400

Val Asp Lys Tyr Val Tyr Ser Ser Gly Trp Val Tyr Leu Glu Ala Pro
                405                 410                 415

Ala Tyr Asp Pro Ala Asn Gly Gln Tyr Gly Tyr Ser Val Trp Ser Tyr
                420                 425                 430

Cys Gly Val Gly
        435

<210> SEQ ID NO 2
<211> LENGTH: 436
<212> TYPE: PRT
<213> ORGANISM: Artificial Sequence
<220> FEATURE:
<223> OTHER INFORMATION: Synthetic protein

<400> SEQUENCE: 2

Met Ala Lys Tyr Ser Glu Leu Glu Glu Gly Gly Leu Ile Met Gln Ala
1               5                   10                  15

Phe Tyr Trp Asp Val Pro Met Gly Gly Ile Trp Trp Asp Thr Ile Ala
```

```
                    20                  25                  30
Gln Lys Ile Pro Asp Trp Ala Ser Ala Gly Ile Ser Ala Ile Trp Ile
                35                  40                  45
Pro Pro Ala Ser Lys Gly Met Gly Gly Ala Tyr Ser Met Gly Tyr Asp
            50                  55                  60
Pro Tyr Asp Phe Phe Asp Leu Gly Glu Tyr Asp Gln Lys Gly Thr Val
65                  70                  75                  80
Glu Thr Arg Phe Gly Ser Lys Gln Glu Leu Val Asn Met Ile Asn Thr
                85                  90                  95
Ala His Ala Tyr Gly Met Lys Val Ile Ala Asp Ile Val Ile Asn His
            100                 105                 110
Arg Ala Gly Gly Asp Leu Glu Trp Asn Pro Phe Val Asn Asp Tyr Thr
        115                 120                 125
Trp Thr Asp Phe Ser Lys Val Ala Ser Gly Lys Tyr Thr Ala Asn Tyr
        130                 135                 140
Leu Asp Phe His Pro Asn Glu Leu His Ala Gly Asp Ser Gly Thr Phe
145                 150                 155                 160
Gly Gly Tyr Pro Asp Ile Cys His Asp Lys Ser Trp Asp Gln Tyr Trp
            165                 170                 175
Leu Trp Ala Ser Gln Glu Ser Tyr Ala Ala Tyr Leu Arg Ser Ile Gly
        180                 185                 190
Ile Asp Ala Trp Arg Phe Asp Tyr Val Lys Gly Tyr Gly Ala Trp Val
        195                 200                 205
Val Lys Asp Trp Leu Asp Trp Trp Gly Gly Trp Ala Val Gly Glu Tyr
        210                 215                 220
Trp Asp Thr Asn Val Asp Ala Leu Leu Asn Trp Ala Tyr Ser Ser Asp
225                 230                 235                 240
Ala Lys Val Phe Asp Phe Pro Leu Tyr Tyr Lys Met Asp Ala Ala Phe
            245                 250                 255
Asp Asn Lys Asn Ile Pro Ala Leu Val Glu Ala Leu Lys Asn Gly Gly
            260                 265                 270
Thr Val Val Ser Arg Asp Pro Phe Lys Ala Val Thr Phe Val Ala Asn
        275                 280                 285
His Asp Thr Asp Ile Ile Trp Asn Lys Tyr Pro Ala Tyr Ala Phe Ile
        290                 295                 300
Leu Thr Tyr Glu Gly Gln Pro Thr Ile Phe Tyr Arg Asp Tyr Glu Glu
305                 310                 315                 320
Trp Leu Asn Lys Asp Lys Leu Lys Asn Leu Ile Trp Ile His Asp Asn
            325                 330                 335
Leu Ala Gly Gly Ser Thr Asp Ile Val Tyr Tyr Asp Asn Asp Glu Leu
            340                 345                 350
Ile Phe Val Arg Asn Gly Tyr Gly Ser Lys Pro Gly Leu Ile Thr Tyr
        355                 360                 365
Ile Asn Leu Ala Ser Ser Lys Ala Gly Arg Trp Val Tyr Val Pro Lys
        370                 375                 380
Phe Ala Gly Ser Cys Ile His Glu Tyr Thr Gly Asn Leu Gly Gly Trp
385                 390                 395                 400
Val Asp Lys Trp Val Asp Ser Ser Gly Trp Val Tyr Leu Glu Ala Pro
            405                 410                 415
Ala His Asp Pro Ala Asn Gly Gln Tyr Gly Tyr Ser Val Trp Ser Tyr
            420                 425                 430
Cys Gly Val Gly
        435
```

<210> SEQ ID NO 3
<211> LENGTH: 436
<212> TYPE: PRT
<213> ORGANISM: Artificial Sequence
<220> FEATURE:
<223> OTHER INFORMATION: Synthetic protein

<400> SEQUENCE: 3

```
Met Ala Lys Tyr Leu Glu Leu Glu Gly Gly Leu Ile Met Gln Ala
1               5                   10                  15

Phe Tyr Trp Asp Val Pro Met Gly Gly Ile Trp Trp Asp Thr Ile Ala
                20                  25                  30

Gln Lys Ile Pro Asp Trp Ala Ser Ala Gly Ile Ser Ala Ile Trp Ile
                35                  40                  45

Pro Pro Ala Ser Lys Gly Met Gly Gly Ala Tyr Ser Met Gly Tyr Asp
50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Ile Lys Val Ile Ala Asp Ile Val Ile Asn His
                100                 105                 110

Arg Ala Gly Gly Asp Leu Glu Trp Asn Pro Phe Val Asn Asp Tyr Thr
                115                 120                 125

Trp Thr Asp Phe Ser Lys Val Ala Ser Gly Lys Tyr Thr Ala Asn Tyr
                130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
                180                 185                 190

Ile Asp Ala Trp Arg Phe Asp Tyr Val Lys Gly Tyr Ala Pro Trp Val
                195                 200                 205

Val Lys Asp Trp Leu Asn Trp Trp Gly Gly Trp Ala Val Gly Glu Tyr
210                 215                 220

Trp Asp Thr Asn Val Asp Ala Val Leu Asn Trp Ala Tyr Ser Ser Gly
225                 230                 235                 240

Ala Lys Val Phe Asp Phe Ala Leu Tyr Tyr Lys Met Asp Glu Ala Phe
                245                 250                 255

Asp Asn Lys Asn Ile Pro Ala Leu Val Ser Ala Leu Gln Asn Gly Gln
                260                 265                 270

Thr Val Val Ser Arg Asp Pro Phe Lys Ala Val Thr Phe Val Ala Asn
                275                 280                 285

His Asp Thr Asp Ile Ile Trp Asn Lys Tyr Pro Ala Tyr Ala Phe Ile
                290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
                325                 330                 335

Leu Ala Gly Gly Ser Thr Asp Ile Val Tyr Tyr Asp Asn Asp Glu Leu
                340                 345                 350

Ile Phe Val Arg Asn Gly Tyr Gly Ser Lys Pro Gly Leu Ile Thr Tyr
                355                 360                 365
```

```
Ile Asn Leu Ala Ser Ser Glu Ala Gly Arg Trp Val Tyr Val Pro Lys
    370                 375                 380

Phe Ala Gly Ala Cys Ile His Glu Tyr Thr Gly Asn Leu Gly Gly Trp
385                 390                 395                 400

Val Asp Lys Trp Val Asp Ser Ser Gly Trp Val Tyr Leu Glu Ala Pro
                405                 410                 415

Ala His Asp Pro Ala Asn Gly Tyr Tyr Gly Tyr Ser Val Trp Ser Tyr
                420                 425                 430

Cys Gly Val Gly
            435

<210> SEQ ID NO 4
<211> LENGTH: 436
<212> TYPE: PRT
<213> ORGANISM: Artificial Sequence
<220> FEATURE:
<223> OTHER INFORMATION: Synthetic protein

<400> SEQUENCE: 4

Met Ala Lys Tyr Ser Glu Leu Glu Glu Gly Val Ile Met Gln Ala
1               5                   10                  15

Phe Tyr Trp Asp Val Pro Gly Gly Ile Trp Trp Asp Thr Ile Arg
                20                  25                  30

Ser Lys Ile Pro Glu Trp Tyr Glu Ala Gly Ile Ser Ala Ile Trp Ile
            35                  40                  45

Pro Pro Ala Ser Lys Gly Met Gly Gly Ala Tyr Ser Met Gly Tyr Asp
50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Met Lys Val Ile Ala Asp Ile Val Ile Asn His
                100                 105                 110

Arg Ala Gly Gly Asp Leu Glu Trp Asn Pro Phe Val Asn Asp Tyr Thr
            115                 120                 125

Trp Thr Asp Phe Ser Lys Val Ala Ser Gly Lys Tyr Thr Ala Asn Tyr
    130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Ala Pro Trp Val
            195                 200                 205

Val Lys Asp Trp Leu Asn Trp Trp Gly Gly Trp Ala Val Gly Glu Tyr
            210                 215                 220

Trp Asp Thr Asn Val Asp Ala Val Leu Asn Trp Ala Tyr Ser Ser Gly
225                 230                 235                 240

Ala Lys Val Phe Asp Phe Ala Leu Tyr Tyr Lys Met Asp Glu Ala Phe
                245                 250                 255

Asp Asn Lys Asn Ile Pro Ala Leu Val Ser Ala Leu Gln Asn Gly Gln
            260                 265                 270

Thr Val Val Ser Arg Asp Pro Phe Lys Ala Val Thr Phe Val Ala Asn
            275                 280                 285
```

His Asp Thr Asp Ile Ile Trp Asn Lys Tyr Leu Ala Tyr Ala Phe Ile
            290                 295                 300

Leu Thr Tyr Glu Gly Gln Pro Val Ile Phe Tyr Arg Asp His Glu Glu
305                 310                 315                 320

Trp Leu Asn Lys Asp Arg Leu Asn Asn Leu Ile Trp Ile His Asp His
                325                 330                 335

Leu Ala Gly Gly Ser Thr Asp Ile Val Tyr Tyr Asp Asn Asp Glu Leu
            340                 345                 350

Ile Phe Val Arg Asn Gly Tyr Gly Asp Lys Pro Gly Leu Ile Thr Tyr
                355                 360                 365

Ile Asn Leu Gly Ser Ser Lys Ala Gly Arg Trp Val Tyr Val Pro Lys
            370                 375                 380

Phe Ala Gly Ala Cys Ile His Glu Tyr Thr Gly Asn Leu Gly Gly Trp
385                 390                 395                 400

Val Asp Lys Tyr Val Tyr Ser Ser Gly Trp Val Tyr Leu Glu Ala Pro
                405                 410                 415

Ala Tyr Asp Pro Ala Asn Gly Gln Tyr Gly Tyr Ser Val Trp Ser Tyr
            420                 425                 430

Cys Gly Val Gly
            435

<210> SEQ ID NO 5
<211> LENGTH: 436
<212> TYPE: PRT
<213> ORGANISM: Artificial Sequence
<220> FEATURE:
<223> OTHER INFORMATION: Synthetic protein

<400> SEQUENCE: 5

Met Ala Lys Tyr Ser Glu Leu Glu Glu Gly Gly Leu Ile Met Gln Ala
1               5                   10                  15

Phe Tyr Trp Asp Val Pro Met Gly Gly Ile Trp Trp Asp Thr Ile Ala
                20                  25                  30

Gln Lys Ile Pro Asp Trp Ala Ser Ala Gly Ile Ser Ala Ile Trp Ile
            35                  40                  45

Pro Pro Ala Ser Lys Gly Met Gly Gly Ala Tyr Ser Met Gly Tyr Asp
        50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Ile Lys Val Ile Ala Asp Ile Val Ile Asn His
            100                 105                 110

Arg Ala Gly Gly Asp Leu Glu Trp Asn Pro Phe Val Gly Asp Tyr Thr
        115                 120                 125

Trp Thr Asp Phe Ser Lys Val Ala Ser Gly Lys Tyr Thr Ala Asn Tyr
        130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Ala Pro Trp Val
        195                 200                 205

Val Lys Asp Trp Leu Asn Trp Trp Gly Gly Trp Ala Val Gly Glu Tyr
210                 215                 220

Trp Asp Thr Asn Val Asp Ala Val Leu Asn Trp Ala Tyr Ser Ser Gly
225                 230                 235                 240

Ala Lys Val Phe Asp Phe Ala Leu Tyr Tyr Lys Met Asp Glu Ala Phe
            245                 250                 255

Asp Asn Asn Asn Ile Pro Ala Leu Val Asp Ala Leu Arg Tyr Gly Gln
                260                 265                 270

Thr Val Val Ser Arg Asp Pro Phe Lys Ala Val Thr Phe Val Ala Asn
            275                 280                 285

His Asp Thr Asp Ile Ile Trp Asn Lys Tyr Pro Ala Tyr Ala Phe Ile
290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
                325                 330                 335

Leu Ala Gly Gly Ser Thr Asp Ile Val Tyr Tyr Asp Asn Asp Glu Leu
            340                 345                 350

Ile Phe Ala Arg Asn Gly Tyr Gly Ser Lys Pro Gly Leu Ile Thr Tyr
            355                 360                 365

Ile Asn Leu Ala Ser Ser Lys Ala Gly Arg Trp Val Tyr Val Pro Lys
370                 375                 380

Phe Ala Gly Ser Cys Ile His Glu Tyr Thr Gly Asn Leu Gly Gly Trp
385                 390                 395                 400

Val Asp Lys Trp Val Asp Ser Ser Gly Trp Val Tyr Leu Glu Ala Pro
                405                 410                 415

Ala His Asp Pro Ala Asn Gly Gln Tyr Gly Tyr Ser Val Trp Ser Tyr
            420                 425                 430

Cys Gly Val Gly
        435

<210> SEQ ID NO 6
<211> LENGTH: 436
<212> TYPE: PRT
<213> ORGANISM: Artificial Sequence
<220> FEATURE:
<223> OTHER INFORMATION: Synthetic protein

<400> SEQUENCE: 6

Met Ala Lys Tyr Leu Glu Leu Glu Gly Gly Leu Ile Met Gln Ala
1               5                   10                  15

Phe Tyr Trp Asp Val Pro Met Gly Gly Ile Trp Trp Asp Thr Ile Ala
                20                  25                  30

Gln Lys Ile Pro Asp Trp Ala Ser Ala Gly Ile Ser Ala Ile Trp Ile
            35                  40                  45

Pro Pro Ala Ser Lys Gly Met Gly Gly Ala Tyr Ser Met Gly Tyr Asp
        50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Met Lys Val Ile Ala Asp Ile Val Ile Asn His
            100                 105                 110

Arg Ala Gly Gly Asp Leu Glu Trp Asn Pro Phe Val Asn Asp Tyr Thr
        115                 120                 125

Trp Thr Asp Phe Ser Lys Val Ala Ser Gly Lys Tyr Thr Ala Asn Tyr
            130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Ala Pro Trp Val
        195                 200                 205

Val Lys Asp Trp Leu Asn Trp Trp Gly Gly Trp Ala Val Gly Glu Tyr
    210                 215                 220

Trp Asp Thr Asn Val Asp Ala Val Leu Asn Trp Ala Tyr Ser Ser Gly
225                 230                 235                 240

Ala Lys Val Phe Asp Phe Ala Leu Tyr Tyr Lys Met Asp Glu Ala Phe
                245                 250                 255

Asp Asn Asn Asn Ile Pro Ala Leu Val Asp Ala Leu Arg Tyr Gly Gln
            260                 265                 270

Thr Val Val Ser Arg Asp Pro Phe Lys Ala Val Thr Phe Val Ala Asn
        275                 280                 285

His Asp Thr Asp Ile Ile Trp Asn Lys Tyr Pro Ala Tyr Ala Phe Ile
    290                 295                 300

Leu Thr Tyr Glu Gly Gln Pro Thr Ile Phe Tyr Arg Asp Tyr Glu Glu
305                 310                 315                 320

Trp Leu Asn Lys Asp Thr Leu Lys Asn Leu Ile Trp Ile His Asp Asn
                325                 330                 335

Leu Ala Gly Gly Ser Thr Ser Ile Val Tyr Tyr Asp Ser Asp Glu Met
            340                 345                 350

Ile Phe Val Arg Asn Gly Tyr Gly Ser Lys Pro Gly Leu Ile Thr Tyr
        355                 360                 365

Ile Asn Leu Gly Ser Ser Lys Val Gly Arg Trp Val Tyr Val Pro Lys
    370                 375                 380

Phe Ala Gly Ala Cys Ile His Glu Tyr Thr Gly Asn Leu Gly Gly Trp
385                 390                 395                 400

Val Asp Lys Trp Val Asp Ser Ser Gly Trp Val Tyr Leu Glu Ala Pro
                405                 410                 415

Ala His Asp Pro Ala Asn Gly Tyr Tyr Gly Tyr Ser Val Trp Ser Tyr
            420                 425                 430

Cys Gly Val Gly
        435

<210> SEQ ID NO 7
<211> LENGTH: 436
<212> TYPE: PRT
<213> ORGANISM: Artificial Sequence
<220> FEATURE:
<223> OTHER INFORMATION: Synthetic protein

<400> SEQUENCE: 7

Met Ala Lys Tyr Leu Glu Leu Glu Glu Gly Gly Val Ile Met Gln Ala
1               5                   10                  15

Phe Tyr Trp Asp Val Pro Ser Gly Gly Ile Trp Trp Asp Thr Ile Arg
            20                  25                  30

Gln Lys Ile Pro Glu Trp Tyr Asp Ala Gly Ile Ser Ala Ile Trp Ile
        35                  40                  45

Pro Pro Ala Ser Lys Gly Met Gly Gly Ala Tyr Ser Met Gly Tyr Asp
 50                  55                  60

Pro Tyr Asp Phe Phe Asp Leu Gly Glu Tyr Asp Gln Lys Gly Thr Val
 65                  70                  75                  80

Glu Thr Arg Phe Gly Ser Lys Gln Glu Leu Val Asn Met Ile Asn Thr
                 85                  90                  95

Ala His Ala Tyr Gly Ile Lys Val Ile Ala Asp Ile Val Ile Asn His
             100                 105                 110

Arg Ala Gly Gly Asp Leu Glu Trp Asn Pro Phe Val Gly Asp Tyr Thr
         115                 120                 125

Trp Thr Asp Phe Ser Lys Val Ala Ser Gly Lys Tyr Thr Ala Asn Tyr
     130                 135                 140

Leu Asp Phe His Pro Asn Glu Val Lys Cys Cys Asp Glu Gly Thr Phe
145                 150                 155                 160

Gly Gly Phe Pro Asp Ile Ala His Glu Lys Ser Trp Asp Gln His Trp
                 165                 170                 175

Leu Trp Ala Ser Asp Glu Ser Tyr Ala Ala Tyr Leu Arg Ser Ile Gly
             180                 185                 190

Val Asp Ala Trp Arg Phe Asp Tyr Val Lys Gly Tyr Gly Ala Trp Val
         195                 200                 205

Val Lys Asp Trp Leu Asp Trp Trp Gly Gly Trp Ala Val Gly Glu Tyr
     210                 215                 220

Trp Asp Thr Asn Val Asp Ala Leu Leu Asn Trp Ala Tyr Ser Ser Asp
225                 230                 235                 240

Ala Lys Val Phe Asp Phe Pro Leu Tyr Tyr Lys Met Asp Glu Ala Phe
                 245                 250                 255

Asp Asn Lys Asn Ile Pro Ala Leu Val Ser Ala Leu Gln Asn Gly Gln
             260                 265                 270

Thr Val Val Ser Arg Asp Pro Phe Lys Ala Val Thr Phe Val Ala Asn
         275                 280                 285

His Asp Thr Asp Ile Ile Trp Asn Lys Tyr Pro Ala Tyr Ala Phe Ile
     290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
                 325                 330                 335

Leu Ala Gly Gly Ser Thr Asp Ile Val Tyr Tyr Asp Asn Asp Glu Leu
             340                 345                 350

Ile Phe Val Arg Asn Gly Tyr Gly Asp Lys Pro Gly Leu Ile Thr Tyr
         355                 360                 365

Ile Asn Leu Gly Ser Ser Lys Ala Gly Arg Trp Val Tyr Val Pro Lys
     370                 375                 380

Phe Ala Gly Ala Cys Ile His Glu Tyr Thr Gly Asn Leu Gly Gly Trp
385                 390                 395                 400

Val Asp Lys Tyr Val Tyr Ser Ser Gly Trp Val Tyr Leu Glu Ala Pro
                 405                 410                 415

Ala Tyr Asp Pro Ala Asn Gly Gln Tyr Gly Tyr Ser Val Trp Ser Tyr
             420                 425                 430

Cys Gly Val Gly
         435

<210> SEQ ID NO 8
<211> LENGTH: 436

<212> TYPE: PRT
<213> ORGANISM: Artificial Sequence
<220> FEATURE:
<223> OTHER INFORMATION: Synthetic protein

<400> SEQUENCE: 8

```
Met Ala Lys Tyr Ser Glu Leu Glu Glu Gly Gly Leu Ile Met Gln Ala
1               5                   10                  15

Phe Tyr Trp Asp Val Pro Met Gly Gly Ile Trp Trp Asp Thr Ile Ala
            20                  25                  30

Gln Lys Ile Pro Asp Trp Ala Ser Ala Gly Ile Ser Ala Ile Trp Ile
        35                  40                  45

Pro Pro Ala Ser Lys Gly Met Gly Gly Ala Tyr Ser Met Gly Tyr Asp
    50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Ile Lys Val Ile Ala Asp Ile Val Ile Asn His
            100                 105                 110

Arg Ala Gly Gly Asp Leu Glu Trp Asn Pro Phe Val Gly Asp Tyr Thr
        115                 120                 125

Trp Thr Asp Phe Ser Lys Val Ala Ser Gly Lys Tyr Thr Ala Asn Tyr
    130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Gly Ala Trp Val
        195                 200                 205

Val Lys Asp Trp Leu Asp Trp Trp Gly Gly Trp Ala Val Gly Glu Tyr
    210                 215                 220

Trp Asp Thr Asn Val Asp Ala Leu Leu Asn Trp Ala Tyr Ser Ser Asp
225                 230                 235                 240

Ala Lys Val Phe Asp Phe Pro Leu Tyr Tyr Lys Met Asp Glu Ala Phe
                245                 250                 255

Asp Asn Lys Asn Ile Pro Ala Leu Val Ser Ala Leu Gln Asn Gly Gln
            260                 265                 270

Thr Val Val Ser Arg Asp Pro Phe Lys Ala Val Thr Phe Val Ala Asn
        275                 280                 285

His Asp Thr Asp Ile Ile Trp Asn Lys Tyr Pro Ala Tyr Ala Phe Ile
    290                 295                 300

Leu Thr Tyr Glu Gly Gln Pro Thr Ile Phe Tyr Arg Asp Tyr Glu Glu
305                 310                 315                 320

Trp Leu Asn Lys Asp Arg Leu Lys Asn Leu Ile Trp Ile His Asp His
                325                 330                 335

Leu Ala Gly Gly Ser Thr Asp Ile Val Tyr Tyr Asp Asn Asp Glu Leu
            340                 345                 350

Ile Phe Val Arg Asn Gly Tyr Gly Ser Lys Pro Gly Leu Ile Thr Tyr
        355                 360                 365

Ile Asn Leu Ala Ser Ser Lys Ala Gly Arg Trp Val Tyr Val Pro Lys
    370                 375                 380
```

```
Phe Ala Gly Ala Cys Ile His Glu Tyr Thr Gly Asn Leu Gly Gly Trp
385                 390                 395                 400

Val Asp Lys Tyr Val Tyr Ser Ser Gly Trp Val Tyr Leu Glu Ala Pro
            405                 410                 415

Ala Tyr Asp Pro Ala Asn Gly Gln Tyr Gly Tyr Ser Val Trp Ser Tyr
            420                 425                 430

Cys Gly Val Gly
        435

<210> SEQ ID NO 9
<211> LENGTH: 436
<212> TYPE: PRT
<213> ORGANISM: Artificial Sequence
<220> FEATURE:
<223> OTHER INFORMATION: Synthetic protein

<400> SEQUENCE: 9

Met Ala Lys Tyr Ser Glu Leu Glu Gly Gly Gly Leu Ile Met Gln Ala
1               5                   10                  15

Phe Tyr Trp Asp Val Pro Met Gly Gly Ile Trp Trp Asp Thr Ile Ala
            20                  25                  30

Gln Lys Ile Pro Asp Trp Ala Ser Ala Gly Ile Ser Ala Ile Trp Ile
        35                  40                  45

Pro Pro Ala Ser Lys Gly Met Gly Gly Ala Tyr Ser Met Gly Tyr Asp
50                  55                  60

Pro Tyr Asp Phe Phe Asp Leu Gly Glu Tyr Asp Gln Glu Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Ile Lys Val Ile Ala Asp Ile Val Ile Asn His
            100                 105                 110

Arg Ala Gly Gly Asp Leu Glu Trp Asn Pro Phe Val Gly Asp Tyr Thr
        115                 120                 125

Trp Thr Asp Phe Ser Lys Val Ala Ser Gly Lys Tyr Thr Ala Asn Tyr
130                 135                 140

Leu Asp Phe His Pro Asn Glu Val Lys Cys Cys Asp Glu Gly Thr Phe
145                 150                 155                 160

Gly Gly Phe Pro Asp Ile Ala His Glu Lys Ser Trp Asp Gln His Trp
                165                 170                 175

Leu Trp Ala Ser Asp Glu Ser Tyr Ala Ala Tyr Leu Arg Ser Ile Gly
            180                 185                 190

Val Asp Ala Trp Arg Phe Asp Tyr Val Lys Gly Tyr Gly Ala Trp Val
        195                 200                 205

Val Lys Asp Trp Leu Asp Trp Trp Gly Gly Trp Ala Val Gly Glu Tyr
210                 215                 220

Trp Asp Thr Asn Val Asp Ala Leu Leu Asn Trp Ala Tyr Ser Ser Asp
225                 230                 235                 240

Ala Lys Val Phe Asp Phe Pro Leu Tyr Tyr Lys Met Asp Ala Ala Phe
                245                 250                 255

Asp Asn Lys Asn Ile Pro Ala Leu Val Glu Ala Leu Lys Asn Gly Gly
            260                 265                 270

Thr Val Val Ser Arg Asp Pro Phe Lys Ala Val Thr Phe Val Ala Asn
        275                 280                 285

His Asp Thr Asp Ile Ile Trp Asn Lys Tyr Pro Ala Tyr Ala Phe Ile
290                 295                 300
```

```
Leu Thr Tyr Glu Gly Gln Pro Thr Ile Phe Tyr Arg Asp Tyr Glu
305                 310                 315                 320

Trp Leu Asn Lys Asp Lys Leu Lys Asn Leu Ile Trp Ile His Asp Asn
                325                 330                 335

Leu Ala Gly Gly Ser Thr Ser Ile Val Tyr Tyr Asp Ser Asp Glu Met
                340                 345                 350

Ile Phe Val Arg Asn Gly Tyr Gly Ser Lys Pro Gly Leu Ile Thr Tyr
                355                 360                 365

Ile Asn Leu Gly Ser Ser Lys Val Gly Arg Trp Val Tyr Val Pro Lys
                370                 375                 380

Phe Ala Gly Ser Cys Ile His Glu Tyr Thr Gly Asn Leu Gly Gly Trp
385                 390                 395                 400

Val Asp Lys Trp Val Asp Ser Ser Gly Trp Val Tyr Leu Glu Ala Pro
                405                 410                 415

Ala His Asp Pro Ala Asn Gly Gln Tyr Gly Tyr Ser Val Trp Ser Tyr
                420                 425                 430

Cys Gly Val Gly
            435
```

<210> SEQ ID NO 10
<211> LENGTH: 436
<212> TYPE: PRT
<213> ORGANISM: Artificial Sequence
<220> FEATURE:
<223> OTHER INFORMATION: Synthetic protein

<400> SEQUENCE: 10

```
Met Ala Lys Tyr Leu Glu Leu Glu Glu Gly Gly Leu Ile Met Gln Ala
1               5                   10                  15

Phe Tyr Trp Asp Val Pro Met Gly Gly Ile Trp Trp Asp Thr Ile Ala
                20                  25                  30

Gln Lys Ile Pro Asp Trp Ala Ser Ala Gly Ile Ser Ala Ile Trp Ile
                35                  40                  45

Pro Pro Ala Ser Lys Gly Met Ser Gly Gly Tyr Ser Met Gly Tyr Asp
            50                  55                  60

Pro Tyr Asp Tyr Phe Asp Leu Gly Glu Tyr Tyr Gln Lys Gly Thr Val
65                  70                  75                  80

Glu Thr Arg Phe Gly Ser Lys Gln Glu Leu Ile Asn Met Ile Asn Thr
                85                  90                  95

Ala His Ala Tyr Gly Ile Lys Val Ile Ala Asp Ile Val Ile Asn His
                100                 105                 110

Arg Ala Gly Gly Asp Leu Glu Trp Asn Pro Phe Val Gly Asp Tyr Thr
            115                 120                 125

Trp Thr Asp Phe Ser Lys Val Ala Ser Gly Lys Tyr Thr Ala Asn Tyr
130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Ala Pro Trp Val
            195                 200                 205

Val Lys Asp Trp Leu Asn Trp Trp Gly Gly Trp Ala Val Gly Glu Tyr
        210                 215                 220
```

Trp Asp Thr Asn Val Asp Ala Val Leu Asn Trp Ala Tyr Ser Ser Gly
225                 230                 235                 240

Ala Lys Val Phe Asp Phe Ala Leu Tyr Tyr Lys Met Asp Glu Ala Phe
            245                 250                 255

Asp Asn Lys Asn Ile Pro Ala Leu Val Ser Ala Leu Gln Asn Gly Gln
            260                 265                 270

Thr Val Val Ser Arg Asp Pro Phe Lys Ala Val Thr Phe Val Ala Asn
            275                 280                 285

His Asp Thr Asp Ile Ile Trp Asn Lys Tyr Pro Ala Tyr Ala Phe Ile
            290                 295                 300

Leu Thr Tyr Glu Gly Gln Pro Thr Ile Phe Tyr Arg Asp Tyr Glu Glu
305                 310                 315                 320

Trp Leu Asn Lys Asp Arg Leu Lys Asn Leu Ile Trp Ile His Asp His
                325                 330                 335

Leu Ala Gly Gly Ser Thr Asp Ile Val Tyr Tyr Asp Asn Asp Glu Leu
                340                 345                 350

Ile Phe Val Arg Asn Gly Tyr Gly Ser Lys Pro Gly Leu Ile Thr Tyr
                355                 360                 365

Ile Asn Leu Ala Ser Ser Lys Ala Gly Arg Trp Val Tyr Val Pro Lys
                370                 375                 380

Phe Ala Gly Ala Cys Ile His Glu His Thr Gly Asn Leu Gly Gly Trp
385                 390                 395                 400

Val Asp Lys Tyr Val Tyr Ser Ser Gly Trp Val Tyr Leu Glu Ala Pro
                405                 410                 415

Ala Tyr Asp Pro Ala Asn Gly Gln Tyr Gly Tyr Ser Val Trp Ser Tyr
                420                 425                 430

Cys Gly Val Gly
            435

<210> SEQ ID NO 11
<211> LENGTH: 436
<212> TYPE: PRT
<213> ORGANISM: Artificial Sequence
<220> FEATURE:
<223> OTHER INFORMATION: Synthetic protein

<400> SEQUENCE: 11

Met Ala Lys Tyr Ser Glu Leu Glu Glu Gly Gly Val Ile Met Gln Ala
1               5                   10                  15

Phe Tyr Trp Asp Val Pro Gly Gly Ile Trp Trp Asp Thr Ile Arg
                20                  25                  30

Ser Lys Ile Pro Glu Trp Tyr Glu Ala Gly Ile Ser Ala Ile Trp Ile
            35                  40                  45

Pro Pro Gly Ser Lys Gly Met Ser Gly Gly Tyr Ser Met Gly Tyr Asp
        50                  55                  60

Pro Tyr Asp Asp Leu Asp Leu Gly Glu Tyr Tyr Gln Lys Gly Thr Val
65                  70                  75                  80

Glu Thr Arg Phe Gly Ser Lys Gln Glu Leu Ile Asn Met Ile Asn Thr
                85                  90                  95

Ala His Ala Tyr Gly Ile Lys Val Ile Ala Asp Ile Val Ile Asn His
            100                 105                 110

Arg Ala Gly Gly Asp Leu Glu Trp Asn Pro Phe Val Gly Asp Tyr Thr
        115                 120                 125

Trp Thr Asp Phe Ser Lys Val Ala Ser Gly Lys Tyr Thr Ala Asn Tyr
    130                 135                 140

```
Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
            165                 170                 175

Leu Trp Ala Ser Gln Glu Ser Tyr Ala Val Tyr Leu Arg Ser Ile Gly
            180                 185                 190

Ile Asp Ala Trp Arg Phe Asp Tyr Val Lys Gly Tyr Gly Ala Trp Val
            195                 200                 205

Val Lys Asp Trp Leu Asp Trp Trp Gly Trp Ala Val Gly Glu Tyr
210                 215                 220

Trp Asp Thr Asn Val Asp Ala Leu Leu Asn Trp Ala Tyr Ser Ser Asp
225                 230                 235                 240

Ala Lys Val Phe Asp Phe Pro Leu Tyr Tyr Lys Met Asp Glu Ala Phe
            245                 250                 255

Asp Asn Lys Asn Ile Pro Ala Leu Val Ser Ala Leu Gln Asn Gly Gln
            260                 265                 270

Thr Val Val Ser Arg Asp Pro Phe Lys Ala Val Thr Phe Val Ala Asn
            275                 280                 285

His Asp Thr Asp Ile Ile Trp Asn Lys Tyr Pro Ala Tyr Ala Phe Ile
290                 295                 300

Leu Thr Tyr Glu Gly Gln Pro Thr Ile Phe Tyr Arg Asp Tyr Glu Glu
305                 310                 315                 320

Trp Leu Asn Lys Asp Arg Leu Lys Asn Leu Ile Trp Ile His Asp Tyr
            325                 330                 335

Leu Ala Gly Gly Ser Thr Asp Ile Val Tyr Tyr Asp Asn Asp Glu Leu
            340                 345                 350

Ile Phe Val Arg Asn Gly Tyr Gly Ser Lys Pro Gly Leu Ile Thr Tyr
            355                 360                 365

Ile Asn Leu Ala Ser Ser Lys Ala Gly Arg Trp Val Tyr Val Pro Lys
370                 375                 380

Phe Ala Gly Ala Cys Ile His Glu Tyr Thr Gly Asn Leu Gly Gly Trp
385                 390                 395                 400

Val Asp Lys Tyr Val Tyr Ser Ser Gly Trp Val Tyr Leu Glu Ala Pro
            405                 410                 415

Ala Tyr Asp Pro Ala Asn Gly Gln Tyr Gly Tyr Ser Val Trp Ser Tyr
            420                 425                 430

Cys Gly Val Gly
        435

<210> SEQ ID NO 12
<211> LENGTH: 436
<212> TYPE: PRT
<213> ORGANISM: Artificial Sequence
<220> FEATURE:
<223> OTHER INFORMATION: Synthetic protein

<400> SEQUENCE: 12

Met Ala Lys Tyr Ser Glu Leu Glu Glu Gly Gly Val Ile Val Gln Ala
1               5                   10                  15

Phe Tyr Trp Asp Val Pro Gly Gly Gly Ile Trp Trp Asp Thr Ile Arg
            20                  25                  30

Ser Lys Ile Pro Glu Trp Tyr Glu Ala Gly Ile Ser Ala Ile Trp Ile
        35                  40                  45

Pro Pro Ala Ser Lys Gly Met Gly Gly Ala Tyr Ser Met Gly Tyr Asp
    50                  55                  60
```

Pro Tyr Asp Phe Phe Asp Leu Gly Glu Tyr Asp Gln Lys Gly Thr Val
 65                  70                  75                  80

Glu Thr Arg Phe Gly Ser Lys Gln Glu Leu Val Asn Met Ile Asn Thr
             85                  90                  95

Ala His Ala Tyr Gly Ile Lys Val Ile Ala Asp Ile Val Ile Asn His
            100                 105                 110

Arg Ala Gly Gly Asp Leu Glu Trp Asn Pro Phe Val Gly Asp Tyr Thr
        115                 120                 125

Trp Thr Asp Phe Ser Lys Val Ala Ser Gly Lys Tyr Thr Ala Asn Tyr
    130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Gly Ala Trp Val
        195                 200                 205

Val Lys Asp Trp Leu Asp Trp Trp Gly Gly Trp Ala Val Gly Glu Tyr
    210                 215                 220

Trp Asp Thr Asn Val Asp Ala Leu Leu Asn Trp Ala Tyr Ser Ser Asp
225                 230                 235                 240

Ala Lys Val Phe Asp Phe Pro Leu Tyr Tyr Lys Met Asp Glu Ala Phe
                245                 250                 255

Asp Asn Lys Asn Ile Pro Ala Leu Val Ser Ala Leu Gln Asn Gly Gln
            260                 265                 270

Thr Val Val Ser Arg Asp Pro Phe Lys Ala Val Thr Phe Val Ala Asn
        275                 280                 285

His Asp Thr Asp Ile Ile Trp Asn Lys Tyr Pro Ala Tyr Ala Phe Ile
    290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
                325                 330                 335

Leu Ala Gly Gly Ser Met Ser Ile Val Tyr Tyr Asp Ser Asp Glu Met
            340                 345                 350

Ile Phe Val Arg Asn Gly Tyr Gly Ser Lys Pro Gly Leu Ile Thr Tyr
        355                 360                 365

Ile Asn Leu Gly Ser Ser Lys Val Gly Arg Trp Val Tyr Val Pro Lys
    370                 375                 380

Phe Ala Gly Ala Cys Ile His Glu Tyr Thr Gly Asn Leu Gly Gly Trp
385                 390                 395                 400

Val Asp Lys Trp Val Asp Ser Ser Gly Trp Val Tyr Leu Glu Ala Pro
                405                 410                 415

Ala His Asp Pro Ala Asn Gly Tyr Tyr Gly Tyr Ser Val Trp Ser Tyr
            420                 425                 430

Cys Gly Val Gly
        435

<210> SEQ ID NO 13
<211> LENGTH: 436
<212> TYPE: PRT
<213> ORGANISM: Artificial Sequence
<220> FEATURE:
<223> OTHER INFORMATION: Synthetic protein

<400> SEQUENCE: 13

| | | | | | | | | | | | | | | |
|---|---|---|---|---|---|---|---|---|---|---|---|---|---|---|
|Met|Ala|Lys|Tyr|Leu|Glu|Leu|Glu|Glu|Gly|Gly|Leu|Ile|Met|Gln|Ala|
|1| | | |5| | | | |10| | | | |15| |

Phe Tyr Trp Asp Val Pro Met Gly Gly Ile Trp Trp Asp Thr Ile Ala
                    20                  25                  30

Gln Lys Ile Pro Asp Trp Ala Ser Ala Gly Ile Ser Ala Ile Trp Ile
                35                  40                  45

Pro Pro Ala Ser Lys Gly Met Ser Gly Gly Tyr Ser Met Gly Tyr Asp
50                      55                  60

Pro Tyr Asp Tyr Phe Asp Leu Gly Glu Tyr Tyr Gln Lys Gly Thr Val
65                  70                  75                  80

Glu Thr Arg Phe Gly Ser Lys Gln Glu Leu Ile Asn Met Ile Asn Thr
                85                  90                  95

Ala His Ala Tyr Gly Met Lys Val Ile Ala Asp Ile Val Ile Asn His
                    100                 105                 110

Arg Ala Gly Gly Asp Leu Glu Trp Asn Pro Phe Val Asn Asp Tyr Thr
                115                 120                 125

Trp Thr Asp Phe Ser Lys Val Ala Ser Gly Lys Tyr Thr Ala Asn Tyr
            130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                    165                 170                 175

Leu Trp Ala Ser Gln Glu Ser Tyr Ala Ala Tyr Leu Arg Ser Ile Gly
                180                 185                 190

Ile Asp Ala Trp Arg Phe Asp Tyr Val Lys Gly Tyr Ala Pro Trp Val
            195                 200                 205

Val Lys Asp Trp Leu Asn Trp Trp Gly Gly Trp Ala Val Gly Glu Tyr
210                 215                 220

Trp Asp Thr Asn Val Asp Ala Val Leu Asn Trp Ala Tyr Ser Ser Gly
225                 230                 235                 240

Ala Lys Val Phe Asp Phe Ala Leu Tyr Tyr Lys Met Asp Glu Ala Phe
                    245                 250                 255

Asp Asn Asn Asn Ile Pro Ala Leu Val Gly Ala Leu Arg Tyr Gly Gln
                260                 265                 270

Thr Val Val Ser Arg Asp Pro Phe Lys Ala Val Thr Phe Val Ala Asn
            275                 280                 285

His Asp Thr Asp Ile Ile Trp Asn Lys Tyr Pro Ala Tyr Ala Phe Ile
290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
                    325                 330                 335

Leu Ala Gly Gly Ser Thr Asp Ile Val Tyr Tyr Asp Asn Asp Glu Leu
                340                 345                 350

Ile Phe Val Arg His Gly Tyr Gly Asp Lys Pro Gly Leu Ile Thr Tyr
            355                 360                 365

Ile Asn Leu Gly Ser Ser Lys Ala Gly Arg Trp Val Tyr Val Pro Lys
370                 375                 380

Phe Ala Gly Ser Cys Ile His Glu Tyr Thr Gly Asn Leu Gly Gly Trp
385                 390                 395                 400

Val Asp Lys Trp Val Asp Ser Ser Gly Trp Val Tyr Leu Glu Ala Pro

-continued

```
                405                 410                 415
Ala His Asp Pro Ala Asn Gly Gln Tyr Gly Tyr Ser Val Trp Ser Tyr
                420                 425                 430

Cys Gly Val Gly
        435

<210> SEQ ID NO 14
<211> LENGTH: 436
<212> TYPE: PRT
<213> ORGANISM: Artificial Sequence
<220> FEATURE:
<223> OTHER INFORMATION: Synthetic protein

<400> SEQUENCE: 14

Met Ala Lys Tyr Ser Glu Leu Glu Glu Gly Val Ile Met Gln Ala
1               5                   10                  15

Phe Tyr Trp Asp Val Pro Gly Gly Ile Trp Trp Asp Thr Ile Arg
                20                  25                  30

Ser Lys Ile Pro Glu Trp Tyr Glu Ala Gly Ile Ser Ala Ile Trp Ile
                35                  40                  45

Pro Pro Ala Ser Lys Gly Met Ser Gly Gly Tyr Ser Met Gly Tyr Asp
50                  55                  60

Pro Tyr Asp Tyr Phe Asp Leu Gly Glu Tyr Tyr Gln Lys Gly Thr Val
65                  70                  75                  80

Glu Thr Arg Phe Gly Ser Lys Gln Glu Leu Ile Asn Met Ile Asn Thr
                85                  90                  95

Ala His Ala Tyr Gly Ile Lys Val Ile Ala Asp Ile Val Ile Asn His
                100                 105                 110

Arg Ala Gly Gly Asp Leu Glu Trp Asn Pro Phe Val Gly Asp Tyr Thr
            115                 120                 125

Trp Thr Asp Phe Ser Lys Val Ala Ser Gly Lys Tyr Thr Ala Asn Tyr
        130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Ala Pro Trp Val
        195                 200                 205

Val Lys Asp Trp Leu Asn Trp Trp Gly Gly Trp Ala Val Gly Glu Tyr
    210                 215                 220

Trp Asp Thr Asn Val Asp Ala Val Leu Asn Trp Ala Tyr Ser Ser Gly
225                 230                 235                 240

Ala Lys Val Phe Asp Phe Ala Leu Tyr Tyr Lys Met Asp Ala Ala Phe
                245                 250                 255

Asp Asn Lys Asn Ile Pro Ala Leu Val Glu Ala Leu Lys Asn Gly Gly
            260                 265                 270

Thr Val Val Ser Arg Asp Pro Phe Lys Ala Val Thr Phe Val Ala Asn
        275                 280                 285

His Asp Thr Asp Ile Ile Trp Asn Lys Tyr Pro Ala Tyr Ala Phe Ile
    290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
```

```
                      325                 330                 335
Leu Ala Gly Gly Ser Thr Asp Ile Val Tyr Tyr Asp Asn Asp Glu Leu
                340                 345                 350

Ile Phe Val Arg Asn Gly Tyr Gly Ser Lys Pro Gly Leu Ile Thr Tyr
            355                 360                 365

Ile Asn Leu Ala Ser Ser Lys Ala Gly Arg Trp Val Tyr Val Pro Lys
        370                 375                 380

Phe Ala Gly Ser Cys Ile His Glu Tyr Thr Gly Asn Leu Gly Gly Trp
385                 390                 395                 400

Val Asp Lys Trp Val Asp Ser Ser Gly Trp Val Tyr Leu Glu Ala Pro
                405                 410                 415

Ala His Asp Pro Ala Asn Gly Gln Tyr Gly Tyr Ser Val Trp Ser Tyr
            420                 425                 430

Cys Gly Val Gly
            435

<210> SEQ ID NO 15
<211> LENGTH: 436
<212> TYPE: PRT
<213> ORGANISM: Artificial Sequence
<220> FEATURE:
<223> OTHER INFORMATION: Synthetic protein

<400> SEQUENCE: 15

Met Ala Lys Tyr Leu Glu Leu Glu Glu Gly Gly Leu Ile Met Gln Ala
1               5                   10                  15

Phe Tyr Trp Asp Val Pro Met Gly Gly Ile Trp Trp Asp Thr Val Ala
                20                  25                  30

Gln Lys Ile Pro Asp Trp Ala Ser Ala Gly Ile Ser Ala Ile Trp Ile
            35                  40                  45

Pro Pro Ala Ser Lys Gly Met Gly Gly Ala Tyr Ser Met Gly Tyr Asp
        50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Ile Lys Val Ile Ala Asp Ile Val Ile Asn His
            100                 105                 110

Arg Ala Gly Gly Asp Leu Glu Trp Asn Pro Phe Val Gly Asp Tyr Thr
        115                 120                 125

Trp Thr Asp Phe Ser Lys Val Val Ser Gly Lys Tyr Thr Ala Asn Tyr
    130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Ala Pro Trp Val
        195                 200                 205

Val Lys Asp Trp Leu Asn Trp Trp Gly Gly Trp Ala Val Gly Glu Tyr
    210                 215                 220

Trp Asp Thr Asn Val Asp Ala Val Leu Asn Trp Ala Tyr Ser Ser Gly
225                 230                 235                 240

Ala Lys Val Phe Asp Phe Ala Leu Tyr Tyr Lys Met Asp Glu Ala Phe
```

```
                    245                 250                 255
Asp Asn Lys Asn Ile Pro Ala Leu Val Ser Ala Leu Gln Asn Gly Gln
            260                 265                 270

Thr Val Val Ser Arg Asp Pro Phe Lys Ala Val Thr Phe Val Ala Asn
            275                 280                 285

His Asp Thr Asp Ile Ile Trp Asn Lys Tyr Leu Ala Tyr Ala Phe Ile
            290                 295                 300

Leu Thr Tyr Glu Gly Gln Pro Val Ile Phe Tyr Arg Asp Tyr Glu Glu
305                 310                 315                 320

Trp Leu Asn Lys Asp Arg Leu Asn Asn Leu Ile Trp Ile His Asp His
                325                 330                 335

Leu Ala Gly Gly Ser Thr Asp Ile Val Tyr Tyr Asp Asn Asp Glu Leu
            340                 345                 350

Ile Phe Val Arg Asn Gly Tyr Gly Asp Lys Pro Gly Leu Ile Thr Tyr
                355                 360                 365

Ile Asn Leu Gly Ser Ser Lys Ala Gly Arg Trp Val Tyr Val Pro Lys
            370                 375                 380

Phe Ala Gly Ala Cys Ile His Glu Tyr Thr Gly Asn Leu Gly Gly Trp
385                 390                 395                 400

Val Asp Lys Tyr Val Tyr Ser Ser Gly Trp Val Tyr Leu Glu Ala Pro
                405                 410                 415

Ala Tyr Asp Pro Ala Asn Gly Gln Tyr Gly Tyr Ser Val Trp Ser Tyr
            420                 425                 430

Cys Gly Val Gly
            435

<210> SEQ ID NO 16
<211> LENGTH: 436
<212> TYPE: PRT
<213> ORGANISM: Artificial Sequence
<220> FEATURE:
<223> OTHER INFORMATION: Synthetic protein

<400> SEQUENCE: 16

Met Ala Lys Tyr Ser Glu Leu Glu Glu Gly Gly Val Ile Met Gln Ala
1               5                   10                  15

Phe Tyr Trp Asp Val Pro Gly Gly Ile Trp Trp Asp Thr Ile Arg
            20                  25                  30

Ser Arg Ile Pro Glu Trp Tyr Glu Ala Gly Ile Ser Ala Ile Trp Ile
            35                  40                  45

Pro Pro Ala Ser Lys Gly Met Gly Gly Ala Tyr Ser Met Gly Tyr Asp
        50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Ile Lys Val Ile Ala Asp Ile Val Ile Asn His
            100                 105                 110

Arg Ala Gly Gly Asp Leu Glu Trp Asn Pro Phe Val Gly Asp Tyr Thr
        115                 120                 125

Trp Thr Asp Phe Ser Lys Val Ala Ser Gly Lys Tyr Thr Ala Asn Tyr
        130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
```

```
                165                 170                 175
Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Gly Ala Trp Val
        195                 200                 205

Val Lys Asp Trp Leu Asn Trp Trp Gly Trp Ala Val Gly Glu Tyr
    210                 215                 220

Trp Asp Thr Asn Val Asp Ala Leu Leu Asn Trp Ala Tyr Ser Ser Gly
225                 230                 235                 240

Ala Lys Val Phe Asp Phe Pro Leu Tyr Tyr Lys Met Asp Glu Ala Phe
                245                 250                 255

Asp Asn Asn Asn Ile Pro Ala Leu Val Asp Ala Leu Arg Tyr Gly Gln
                260                 265                 270

Thr Val Val Ser Arg Asp Pro Phe Lys Ala Val Thr Phe Val Ala Asn
            275                 280                 285

His Asp Thr Asp Ile Ile Trp Asn Lys Tyr Pro Ala Tyr Ala Phe Ile
        290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
                325                 330                 335

Leu Ala Gly Gly Ser Thr Ser Ile Val Tyr Tyr Asp Ser Asp Glu Met
                340                 345                 350

Ile Phe Val Arg Thr Gly Tyr Gly Ser Lys Pro Gly Leu Ile Thr Tyr
            355                 360                 365

Ile Asn Leu Gly Ser Ser Lys Val Gly Arg Trp Val Tyr Val Pro Lys
        370                 375                 380

Phe Ala Gly Ala Cys Ile His Glu Tyr Thr Gly Asn Leu Gly Gly Trp
385                 390                 395                 400

Val Asp Lys Tyr Val Tyr Ser Ser Gly Trp Val Tyr Leu Glu Ala Pro
                405                 410                 415

Ala Tyr Asp Pro Ala Asn Gly Gln Tyr Gly Tyr Ser Val Trp Ser Tyr
                420                 425                 430

Cys Gly Val Gly
        435

<210> SEQ ID NO 17
<211> LENGTH: 436
<212> TYPE: PRT
<213> ORGANISM: Artificial Sequence
<220> FEATURE:
<223> OTHER INFORMATION: Synthetic protein

<400> SEQUENCE: 17

Met Ala Lys Tyr Ser Glu Leu Glu Glu Gly Gly Val Ile Met Gln Ala
1               5                   10                  15

Phe Tyr Trp Asp Val Pro Ser Gly Gly Ile Trp Trp Asp Thr Ile Arg
            20                  25                  30

Gln Lys Ile Pro Glu Trp Tyr Asp Ala Gly Ile Ser Ala Ile Trp Ile
        35                  40                  45

Pro Pro Ala Ser Lys Gly Met Ser Gly Gly Tyr Ser Met Gly Tyr Asp
    50                  55                  60

Pro Tyr Asp Tyr Phe Asp Leu Gly Glu Tyr Tyr Gln Lys Gly Thr Val
65                  70                  75                  80

Glu Thr Arg Phe Gly Ser Lys Gln Glu Leu Ile Asn Met Ile Asn Thr
```

85                  90                  95
Ala His Ala Tyr Gly Ile Lys Val Ile Ala Asp Ile Val Ile Asn His
            100                 105                 110

Arg Ala Gly Asp Leu Glu Trp Asn Pro Phe Val Gly Asp Tyr Thr
            115                 120                 125

Trp Thr Asp Phe Ser Lys Val Ala Ser Gly Lys Tyr Thr Ala Asn Tyr
    130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Gly Ala Trp Val
            195                 200                 205

Val Lys Asp Trp Leu Asn Trp Trp Gly Gly Trp Ala Val Gly Glu Tyr
    210                 215                 220

Trp Asp Thr Asn Val Asp Ala Leu Leu Asn Trp Ala Tyr Ser Ser Gly
225                 230                 235                 240

Ala Lys Val Phe Asp Phe Pro Leu Tyr Tyr Lys Met Asp Ala Ala Phe
                245                 250                 255

Asp Asn Lys Asn Ile Pro Ala Leu Val Glu Ala Leu Lys Asn Gly Gly
            260                 265                 270

Thr Val Val Ser Arg Asp Pro Phe Lys Ala Val Thr Phe Val Ala Asn
    275                 280                 285

His Asp Thr Asp Ile Ile Trp Thr Lys Tyr Leu Ala Tyr Ala Phe Ile
290                 295                 300

Leu Thr Tyr Glu Gly Gln Pro Val Ile Phe Tyr Arg Asp Tyr Glu Glu
305                 310                 315                 320

Trp Leu Asn Lys Asp Arg Leu Asn Asn Leu Ile Trp Ile His Asp His
                325                 330                 335

Leu Ala Gly Gly Ser Thr Asp Ile Val Tyr Tyr Asp Asn Asp Glu Leu
            340                 345                 350

Ile Phe Val Arg Asn Gly Tyr Gly Asp Lys Pro Gly Leu Ile Thr Tyr
    355                 360                 365

Ile Asn Leu Gly Ser Ser Lys Ala Gly Arg Trp Val Tyr Val Pro Lys
370                 375                 380

Phe Ala Gly Ser Cys Ile His Glu Tyr Thr Gly Asn Leu Gly Gly Trp
385                 390                 395                 400

Val Asp Lys Trp Val Asp Ser Ser Gly Trp Val Tyr Leu Glu Ala Pro
                405                 410                 415

Ala His Asp Pro Ala Asn Gly Gln Tyr Gly Tyr Ser Val Trp Ser Tyr
            420                 425                 430

Cys Gly Val Gly
        435

<210> SEQ ID NO 18
<211> LENGTH: 436
<212> TYPE: PRT
<213> ORGANISM: Artificial Sequence
<220> FEATURE:
<223> OTHER INFORMATION: Synthetic protein

<400> SEQUENCE: 18

Met Ala Lys Tyr Ser Glu Leu Glu Glu Gly Gly Val Ile Met Gln Ala

-continued

```
1               5                   10                  15
Phe Tyr Trp Asp Val Pro Gly Gly Ile Trp Trp Asp Thr Ile Arg
                20                  25                  30
Ser Lys Ile Pro Glu Trp Tyr Glu Ala Gly Ile Ser Ala Ile Trp Ile
                35                  40                  45
Pro Pro Ala Ser Lys Gly Met Gly Gly Ala Tyr Ser Met Gly Tyr Asp
 50                  55                  60
Pro Tyr Asp Phe Phe Asp Leu Gly Glu Tyr Asp Gln Lys Gly Thr Val
 65                  70                  75                  80
Glu Thr Arg Phe Gly Ser Lys Gln Glu Leu Val Asn Met Ile Asn Thr
                85                  90                  95
Ala His Ala Tyr Gly Ile Lys Val Ile Ala Asp Ile Val Ile Asn His
                100                 105                 110
Arg Ala Gly Gly Asp Leu Glu Trp Asn Pro Phe Val Asn Asp Tyr Thr
                115                 120                 125
Trp Thr Asp Phe Ser Lys Val Ala Ser Gly Lys Tyr Thr Ala Asn Tyr
 130                 135                 140
Leu Asp Phe His Pro Asn Glu Val Lys Cys Cys Asp Glu Gly Thr Phe
 145                 150                 155                 160
Gly Gly Phe Pro Asp Ile Ala His Glu Lys Ser Trp Asp Gln His Trp
                165                 170                 175
Leu Trp Ala Ser Asp Glu Ser Tyr Ala Ala Tyr Leu Arg Ser Ile Gly
                180                 185                 190
Val Asp Ala Trp Arg Phe Asp Tyr Val Lys Gly Tyr Ala Pro Trp Val
                195                 200                 205
Val Lys Asp Trp Leu Asn Trp Trp Gly Gly Trp Ala Val Gly Glu Tyr
 210                 215                 220
Trp Asp Thr Asn Val Asp Ala Val Leu Asn Trp Ala Tyr Ser Ser Gly
 225                 230                 235                 240
Ala Lys Val Phe Asp Phe Ala Leu Tyr Tyr Lys Met Asp Ala Ala Phe
                245                 250                 255
Asp Asn Lys Asn Ile Pro Ala Leu Val Glu Ala Leu Lys Asn Gly Gly
                260                 265                 270
Thr Val Val Ser Arg Asp Pro Phe Lys Ala Val Thr Phe Val Ala Asn
                275                 280                 285
His Asp Thr Asp Ile Ile Trp Asn Lys Tyr Pro Ala Tyr Ala Phe Ile
                290                 295                 300
Leu Thr Tyr Glu Gly Gln Pro Thr Ile Phe Tyr Arg Asp Tyr Glu Glu
 305                 310                 315                 320
Trp Leu Asn Lys Asp Lys Leu Lys Asn Leu Ile Trp Ile His Asp Asn
                325                 330                 335
Val Ala Gly Gly Ser Thr Asp Ile Val Tyr Tyr Asp Asn Asp Glu Leu
                340                 345                 350
Ile Phe Val Arg Asn Gly Tyr Gly Asp Lys Pro Gly Leu Ile Thr Tyr
                355                 360                 365
Ile Asn Leu Gly Ser Ser Lys Ala Gly Arg Trp Val Tyr Val Pro Lys
 370                 375                 380
Phe Ala Gly Ser Cys Ile His Glu Tyr Thr Gly Asn Leu Gly Gly Trp
 385                 390                 395                 400
Val Asp Lys Trp Val Asp Ser Ser Gly Trp Val Tyr Leu Glu Ala Pro
                405                 410                 415
Ala His Asp Pro Ala Asn Gly Gln Tyr Gly Tyr Ser Val Trp Ser Tyr
                420                 425                 430
```

```
Cys Gly Val Gly
        435

<210> SEQ ID NO 19
<211> LENGTH: 436
<212> TYPE: PRT
<213> ORGANISM: Artificial Sequence
<220> FEATURE:
<223> OTHER INFORMATION: Synthetic protein

<400> SEQUENCE: 19

Met Ala Lys Tyr Leu Glu Leu Glu Glu Gly Gly Val Ile Met Gln Ala
1               5                   10                  15

Phe Tyr Trp Asp Val Pro Ser Gly Gly Ile Trp Trp Asp Thr Ile Arg
            20                  25                  30

Gln Lys Ile Pro Glu Trp Tyr Asp Ala Gly Ile Ser Ala Ile Trp Ile
        35                  40                  45

Pro Pro Ala Ser Lys Gly Met Gly Gly Ala Tyr Ser Met Gly Tyr Asp
    50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Met Lys Val Ile Ala Asp Ile Val Ile Asn His
            100                 105                 110

Arg Ala Gly Gly Asp Leu Glu Trp Asn Pro Phe Val Asn Asp Tyr Thr
        115                 120                 125

Trp Thr Asp Phe Ser Lys Val Ala Ser Gly Lys Tyr Thr Ala Asn Tyr
    130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Gly Ala Arg Val
        195                 200                 205

Val Lys Asp Trp Leu Asn Trp Trp Gly Gly Trp Ala Val Gly Glu Tyr
    210                 215                 220

Trp Asp Thr Asn Val Asp Ala Leu Leu Asn Trp Ala Tyr Ser Ser Gly
225                 230                 235                 240

Ala Lys Val Phe Asp Phe Pro Leu Tyr Tyr Lys Met Asp Glu Ala Phe
                245                 250                 255

Asp Asn Lys Asn Ile Pro Ala Leu Val Ser Ala Leu Gln Asn Gly Gln
            260                 265                 270

Thr Val Val Ser Arg Asp Pro Phe Lys Ala Val Thr Phe Val Ala Asn
        275                 280                 285

His Asp Thr Asp Ile Ile Trp Asn Lys Tyr Pro Ala Tyr Ala Phe Ile
    290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
                325                 330                 335

Leu Ala Gly Gly Ser Thr Asp Ile Val Tyr Tyr Asp Asn Asp Glu Leu
            340                 345                 350
```

Ile Phe Val Arg Asn Gly Tyr Gly Ser Lys Pro Gly Leu Ile Thr Tyr
            355                 360                 365

Ile Asn Leu Ala Ser Ser Lys Ala Gly Arg Trp Val Tyr Val Pro Lys
            370                 375                 380

Phe Ala Gly Ser Cys Ile His Glu Tyr Thr Gly Asn Leu Gly Gly Trp
385                 390                 395                 400

Val Asp Lys Trp Val Asp Ser Ser Gly Trp Val Tyr Leu Glu Ala Pro
            405                 410                 415

Ala His Asp Pro Ala Asn Gly Gln Tyr Gly Tyr Ser Val Trp Ser Tyr
            420                 425                 430

Cys Gly Val Gly
        435

<210> SEQ ID NO 20
<211> LENGTH: 436
<212> TYPE: PRT
<213> ORGANISM: Artificial Sequence
<220> FEATURE:
<223> OTHER INFORMATION: Synthetic protein

<400> SEQUENCE: 20

Met Ala Lys Tyr Leu Glu Leu Glu Glu Gly Gly Val Ile Met Gln Ala
1               5                   10                  15

Phe Tyr Trp Asp Val Pro Ser Gly Gly Ile Trp Trp Asp Thr Ile Arg
            20                  25                  30

Gln Lys Ile Pro Glu Trp Tyr Asp Ala Gly Ile Ser Ala Ile Trp Ile
            35                  40                  45

Pro Pro Ala Ser Arg Gly Met Ser Gly Gly Tyr Ser Met Gly Tyr Asp
50                  55                  60

Pro Tyr Asp Tyr Phe Asp Leu Gly Glu Tyr Tyr Gln Lys Gly Thr Val
65                  70                  75                  80

Glu Thr Arg Phe Gly Ser Lys Gln Glu Leu Ile Asn Met Ile Asn Thr
            85                  90                  95

Ala His Ala Tyr Gly Met Lys Val Ile Ala Asp Ile Val Ile Asn His
            100                 105                 110

Arg Ala Gly Gly Asp Leu Glu Trp Asn Pro Phe Val Asn Asp Tyr Thr
            115                 120                 125

Trp Thr Asp Phe Ser Lys Val Ala Ser Gly Lys Tyr Thr Ala Asn Tyr
            130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
            165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Gly Ala Trp Val
            195                 200                 205

Val Lys Asp Trp Leu Asn Trp Trp Gly Gly Trp Ala Val Gly Glu Tyr
            210                 215                 220

Trp Asp Pro Asn Val Asp Ala Leu Leu Pro Trp Ala Tyr Ser Ser Gly
225                 230                 235                 240

Ala Lys Val Phe Asp Phe Pro Leu Tyr Tyr Lys Met Asp Glu Ala Phe
            245                 250                 255

Asp Asn Lys Asn Ile Pro Ala Leu Val Ser Ala Leu Gln Asn Gly Gln
            260                 265                 270

```
Thr Val Val Ser Arg Asp Pro Phe Lys Ala Val Thr Phe Val Ala Asn
            275                 280                 285

His Asp Thr Asp Ile Ile Trp Asn Lys Tyr Pro Ala Tyr Ala Phe Ile
        290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
                325                 330                 335

Leu Ala Gly Gly Ser Thr Asp Ile Val Tyr Tyr Asp Asn Asp Glu Leu
            340                 345                 350

Ile Phe Val Arg Asn Gly Tyr Gly Asp Lys Pro Gly Leu Ile Thr Tyr
            355                 360                 365

Ile Asn Leu Gly Ser Ser Lys Ala Gly Arg Trp Val Tyr Val Pro Lys
        370                 375                 380

Phe Ala Gly Ala Cys Ile His Glu Tyr Thr Gly Asn Leu Gly Gly Trp
385                 390                 395                 400

Val Asp Lys Trp Val Asp Ser Ser Gly Trp Val Tyr Leu Glu Ala Pro
                405                 410                 415

Ala His Asp Pro Ala Asn Gly Tyr Tyr Gly Tyr Ser Val Trp Ser Tyr
            420                 425                 430

Cys Gly Val Gly
        435

<210> SEQ ID NO 21
<211> LENGTH: 436
<212> TYPE: PRT
<213> ORGANISM: Artificial Sequence
<220> FEATURE:
<223> OTHER INFORMATION: Synthetic protein

<400> SEQUENCE: 21

Met Ala Lys Tyr Leu Glu Leu Glu Glu Gly Gly Val Ile Met Gln Ala
1               5                   10                  15

Phe Tyr Trp Asp Val Pro Ser Gly Gly Ile Trp Trp Asp Thr Ile Arg
            20                  25                  30

Gln Lys Ile Pro Glu Trp Tyr Asp Ala Gly Ile Ser Ala Ile Trp Ile
        35                  40                  45

Pro Pro Ala Ser Lys Gly Met Ser Gly Gly Tyr Ser Met Gly Tyr Asp
    50                  55                  60

Pro Tyr Asp Tyr Phe Asp Leu Gly Glu Tyr Tyr Gln Lys Gly Thr Val
65                  70                  75                  80

Glu Thr Arg Phe Gly Ser Lys Gln Glu Leu Ile Asn Met Ile Asn Thr
                85                  90                  95

Ala His Ala Tyr Gly Ile Lys Val Ile Ala Asp Ile Val Ile Asn His
            100                 105                 110

Arg Ala Gly Gly Asp Leu Glu Trp Asn Pro Phe Val Gly Asp Tyr Thr
        115                 120                 125

Trp Thr Asp Phe Ser Lys Val Ala Ser Gly Lys Tyr Thr Ala Asn Tyr
    130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190
```

```
Ile Asp Ala Trp Arg Phe Asp Tyr Val Lys Gly Tyr Gly Ala Trp Val
            195                 200                 205

Val Lys Asp Trp Leu Asn Trp Trp Gly Gly Trp Ala Val Gly Glu Tyr
210                 215                 220

Trp Asp Thr Asn Val Asp Ala Leu Leu Asn Trp Ala Tyr Ser Ser Gly
225                 230                 235                 240

Ala Lys Val Phe Asp Phe Pro Leu Tyr Tyr Lys Met Asp Ala Ala Phe
            245                 250                 255

Asp Asn Lys Asn Ile Pro Ala Leu Val Glu Ala Leu Lys Asn Gly Gly
            260                 265                 270

Thr Val Val Ser Arg Asp Pro Phe Lys Ala Val Thr Phe Val Ala Asn
            275                 280                 285

His Asp Thr Asp Ile Ile Trp Asn Lys Tyr Pro Ala Tyr Ala Phe Ile
            290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
            325                 330                 335

Leu Ala Gly Gly Ser Thr Ser Ile Val Tyr Tyr Asp Ser Asp Glu Met
            340                 345                 350

Ile Phe Val Arg Asn Gly Tyr Gly Ser Lys Pro Gly Leu Ile Thr Tyr
            355                 360                 365

Ile Asn Leu Gly Ser Ser Lys Val Gly Arg Trp Val Tyr Val Pro Lys
370                 375                 380

Phe Ala Gly Ala Cys Ile His Glu Tyr Thr Gly Asn Leu Gly Gly Trp
385                 390                 395                 400

Val Asp Lys Tyr Val Tyr Ser Ser Gly Trp Val Tyr Leu Glu Ala Pro
            405                 410                 415

Ala Tyr Asp Pro Ala Asn Gly Gln Tyr Gly Tyr Ser Val Trp Ser Tyr
            420                 425                 430

Cys Gly Val Gly
            435

<210> SEQ ID NO 22
<211> LENGTH: 436
<212> TYPE: PRT
<213> ORGANISM: Artificial Sequence
<220> FEATURE:
<223> OTHER INFORMATION: Synthetic protein

<400> SEQUENCE: 22

Met Ala Lys Tyr Ser Glu Leu Glu Glu Gly Gly Val Ile Met Gln Ala
1               5                   10                  15

Phe Tyr Trp Asp Val Pro Gly Gly Gly Ile Trp Trp Asp Thr Ile Arg
            20                  25                  30

Ser Lys Ile Pro Glu Trp Tyr Glu Ala Gly Ile Ser Ala Ile Trp Ile
        35                  40                  45

Pro Pro Ala Ser Lys Gly Met Gly Gly Ala Tyr Ser Met Gly Tyr Asp
    50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Ile Lys Val Ile Ala Asp Ile Val Ile Asn His
            100                 105                 110
```

Arg Ala Gly Gly Asp Leu Glu Trp Asn Pro Phe Val Gly Asp Tyr Thr
            115                 120                 125

Trp Thr Asp Phe Ser Lys Val Ala Ser Gly Lys Tyr Thr Ala Asn Tyr
130                 135                 140

Leu Asp Phe His Pro Asn Glu Val Lys Cys Cys Asp Glu Gly Thr Phe
145                 150                 155                 160

Gly Gly Phe Pro Asp Ile Ala His Glu Lys Ser Trp Asp Gln His Trp
                165                 170                 175

Leu Trp Ala Ser Asp Glu Ser Tyr Ala Ala Tyr Leu Arg Ser Ile Gly
            180                 185                 190

Val Asp Ala Trp Arg Phe Asp Tyr Val Lys Gly Tyr Gly Ala Trp Val
            195                 200                 205

Val Lys Asp Trp Leu Asp Trp Trp Gly Gly Trp Ala Val Gly Glu Tyr
        210                 215                 220

Trp Asp Thr Asn Val Asp Ala Leu Leu Asn Trp Ala Tyr Ser Ser Asp
225                 230                 235                 240

Ala Lys Val Phe Asp Phe Pro Leu Tyr Tyr Lys Met Asp Glu Ala Phe
                245                 250                 255

Asp Asn Lys Asn Ile Pro Ala Leu Val Ser Ala Leu Gln Asn Gly Gln
            260                 265                 270

Thr Val Val Ser Arg Asp Pro Phe Lys Ala Val Thr Phe Val Ala Asn
        275                 280                 285

His Asp Thr Asp Ile Ile Trp Asn Lys Tyr Pro Ala Tyr Ala Phe Ile
        290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
                325                 330                 335

Leu Val Gly Gly Ser Thr Ser Ile Val Tyr Tyr Asp Ser Asp Glu Met
            340                 345                 350

Ile Phe Val Arg Asn Gly Tyr Gly Ser Lys Pro Gly Leu Ile Thr Tyr
            355                 360                 365

Ile Asn Leu Gly Ser Ser Lys Val Gly Arg Trp Val Tyr Val Pro Lys
        370                 375                 380

Phe Ala Gly Ser Cys Ile His Glu Tyr Thr Gly Asn Leu Gly Gly Trp
385                 390                 395                 400

Val Asp Lys Trp Val Asp Ser Ser Gly Trp Val Tyr Leu Glu Ala Pro
                405                 410                 415

Ala His Asp Pro Ala Asn Gly Gln Tyr Gly Tyr Ser Val Trp Ser Tyr
            420                 425                 430

Cys Gly Val Gly
        435

<210> SEQ ID NO 23
<211> LENGTH: 436
<212> TYPE: PRT
<213> ORGANISM: Artificial Sequence
<220> FEATURE:
<223> OTHER INFORMATION: Synthetic protein

<400> SEQUENCE: 23

Met Ala Lys Tyr Ser Asp Leu Glu Glu Gly Gly Val Ile Met Gln Ala
1                   5                   10                  15

Phe Tyr Trp Asp Val Pro Gly Gly Gly Ile Trp Trp Asp Thr Ile Arg
            20                  25                  30

```
Ser Lys Ile Pro Glu Trp Tyr Glu Ala Gly Ile Ser Ala Ile Trp Ile
        35                  40                  45
Pro Pro Ala Ser Lys Gly Met Gly Gly Ala Tyr Ser Met Gly Tyr Asp
 50                  55                  60
Pro Tyr Asp Phe Phe Asp Leu Gly Glu Tyr Asp Gln Lys Gly Thr Val
 65                  70                  75                  80
Glu Thr Arg Phe Gly Ser Lys Gln Glu Leu Val Asn Met Ile Asn Thr
                 85                  90                  95
Ala His Ala Tyr Gly Ile Lys Val Ile Ala Asp Ile Val Ile Asn His
                100                 105                 110
Arg Ala Gly Gly Asp Leu Glu Trp Asn Pro Phe Val Gly Asp Tyr Thr
                115                 120                 125
Trp Thr Asp Phe Ser Lys Val Ala Ser Gly Lys Tyr Thr Ala Asn Tyr
        130                 135                 140
Leu Asp Phe His Pro Asn Glu Val Lys Cys Cys Asp Glu Gly Thr Phe
145                 150                 155                 160
Gly Gly Phe Pro Asp Ile Ala His Glu Lys Ser Trp Asp Gln His Trp
                165                 170                 175
Leu Trp Ala Ser Asp Glu Ser Tyr Ala Ala Tyr Leu Arg Ser Ile Gly
        180                 185                 190
Val Asp Ala Trp Arg Phe Asp Tyr Val Lys Gly Tyr Gly Ala Trp Val
        195                 200                 205
Val Lys Asp Trp Leu Asn Trp Trp Gly Gly Trp Ala Val Gly Glu Tyr
        210                 215                 220
Trp Asp Thr Asn Val Asp Ala Leu Leu Asn Trp Ala Tyr Ser Ser Gly
225                 230                 235                 240
Ala Lys Val Phe Asp Phe Pro Leu Tyr Tyr Lys Met Asp Glu Ala Phe
                245                 250                 255
Asp Asn Lys Asn Ile Pro Ala Leu Val Ser Ala Leu Gln Asn Gly Gln
                260                 265                 270
Thr Val Val Ser Arg Asp Pro Phe Lys Ala Val Thr Phe Val Ala Asn
        275                 280                 285
His Asp Thr Asp Ile Ile Trp Asn Lys Tyr Pro Ala Tyr Ala Phe Ile
        290                 295                 300
Leu Thr Tyr Glu Gly Gln Pro Thr Ile Phe Tyr Arg Asp Tyr Glu Glu
305                 310                 315                 320
Trp Leu Asn Lys Asp Lys Leu Lys Asn Leu Ile Trp Ile His Asp Asn
                325                 330                 335
Leu Ala Gly Gly Ser Thr Asp Ile Val Tyr Tyr Asp Asn Asp Glu Leu
                340                 345                 350
Ile Phe Val Arg Asn Gly Tyr Gly Asp Lys Pro Gly Leu Ile Thr Tyr
                355                 360                 365
Ile Asn Leu Gly Ser Ser Lys Ala Gly Arg Trp Val Tyr Val Pro Lys
370                 375                 380
Phe Ala Gly Ala Cys Ile His Glu Tyr Thr Gly Asn Leu Gly Gly Trp
385                 390                 395                 400
Val Asp Lys Tyr Val Tyr Ser Ser Gly Trp Val Tyr Leu Glu Ala Pro
                405                 410                 415
Ala Tyr Asp Pro Ala Asn Gly Gln Tyr Gly Tyr Ser Val Trp Ser Tyr
                420                 425                 430
Cys Gly Val Gly
        435
```

<210> SEQ ID NO 24
<211> LENGTH: 436
<212> TYPE: PRT
<213> ORGANISM: Artificial Sequence
<220> FEATURE:
<223> OTHER INFORMATION: Synthetic protein

<400> SEQUENCE: 24

```
Met Ala Lys Tyr Thr Glu Leu Glu Glu Gly Val Ile Met Gln Ala
1               5                   10                  15

Phe Tyr Trp Asp Val Pro Gly Gly Ile Trp Trp Asp Thr Ile Arg
                20                  25                  30

Ser Lys Ile Pro Glu Trp Tyr Glu Ala Gly Ile Ser Ala Ile Trp Ile
            35                  40                  45

Pro Pro Ala Ser Lys Gly Met Gly Gly Ala Tyr Ser Met Gly Tyr Asp
        50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Met Lys Val Ile Ala Asp Ile Val Ile Asn His
            100                 105                 110

Arg Ala Gly Gly Asp Leu Glu Trp Asn Pro Phe Val Asn Asp Tyr Thr
        115                 120                 125

Trp Thr Asp Phe Ser Lys Val Ala Ser Gly Lys Tyr Thr Ala Asn Tyr
130                 135                 140

Leu Asp Phe His Pro Asn Glu Val Lys Cys Cys Asp Glu Gly Thr Phe
145                 150                 155                 160

Gly Gly Phe Pro Asp Ile Ala His Glu Lys Ser Trp Asp Gln His Trp
                165                 170                 175

Leu Trp Ala Ser Asp Glu Ser Tyr Ala Ala Tyr Leu Arg Ser Ile Gly
            180                 185                 190

Val Asp Ala Trp Arg Phe Asp Tyr Val Lys Gly Tyr Gly Ala Trp Val
        195                 200                 205

Val Lys Asp Trp Leu Asn Trp Trp Gly Gly Trp Ala Val Gly Glu Tyr
210                 215                 220

Trp Asp Thr Asn Val Asp Ala Leu Leu Asn Trp Ala Tyr Ser Ser Gly
225                 230                 235                 240

Ala Lys Val Phe Asp Phe Pro Leu Tyr Tyr Lys Met Asp Glu Ala Phe
                245                 250                 255

Asp Asn Lys Asn Ile Pro Ala Leu Val Ser Ala Leu Gln Asn Gly Gln
            260                 265                 270

Thr Val Val Ser Arg Asp Pro Phe Lys Ala Val Thr Phe Val Ala Asn
        275                 280                 285

His Asp Thr Asp Ile Ile Trp Asn Lys Tyr Leu Ala Tyr Ala Phe Ile
290                 295                 300

Leu Thr Tyr Glu Gly Gln Pro Val Ile Phe Tyr Arg Asp Tyr Glu Glu
305                 310                 315                 320

Trp Leu Asn Lys Asp Arg Leu Asn Asn Leu Ile Trp Ile His Asp His
                325                 330                 335

Leu Ala Gly Gly Ser Thr Ser Ile Val Tyr Tyr Asp Ser Asp Glu Met
            340                 345                 350

Ile Phe Val Arg Asn Gly Tyr Gly Ser Lys Pro Gly Leu Ile Thr Tyr
        355                 360                 365
```

```
Ile Asn Leu Gly Ser Ser Lys Val Gly Arg Trp Val Tyr Val Pro Lys
370                 375                 380

Phe Ala Gly Pro Cys Ile His Glu Tyr Thr Gly Asn Leu Gly Gly Trp
385                 390                 395                 400

Val Asp Lys Trp Val Asp Ser Ser Gly Trp Val Tyr Leu Glu Ala Pro
                405                 410                 415

Ala His Asp Pro Ala Asn Gly Gln Tyr Gly Tyr Ser Val Trp Ser Tyr
                420                 425                 430

Cys Gly Val Gly
        435

<210> SEQ ID NO 25
<211> LENGTH: 436
<212> TYPE: PRT
<213> ORGANISM: Artificial Sequence
<220> FEATURE:
<223> OTHER INFORMATION: Synthetic protein

<400> SEQUENCE: 25

Met Ala Lys Tyr Leu Glu Leu Glu Glu Gly Gly Val Ile Met Gln Ala
1               5                   10                  15

Phe Tyr Trp Asp Val Pro Ser Gly Gly Ile Trp Asp Thr Ile Arg
            20                  25                  30

Gln Lys Ile Pro Glu Trp Tyr Asp Ala Gly Ile Ser Ala Ile Trp Ile
        35                  40                  45

Pro Pro Ala Ser Lys Gly Met Gly Gly Ala Tyr Ser Met Gly Tyr Asp
    50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Met Lys Val Ile Ala Asp Ile Val Ile Asn His
            100                 105                 110

Arg Ala Gly Gly Asp Leu Glu Trp Asn Pro Phe Val Asn Asp Tyr Thr
        115                 120                 125

Trp Thr Asp Phe Ser Lys Val Ala Ser Gly Lys Tyr Thr Ala Asn Tyr
    130                 135                 140

Leu Asp Phe His Pro Asn Glu Val Lys Cys Cys Asp Glu Gly Thr Phe
145                 150                 155                 160

Gly Gly Phe Pro Asp Ile Ala His Glu Lys Ser Trp Asp Gln His Trp
                165                 170                 175

Leu Trp Ala Ser Asp Glu Ser Tyr Ala Ala Tyr Leu Arg Ser Ile Gly
            180                 185                 190

Val Asp Ala Trp Arg Phe Asp Tyr Val Lys Gly Tyr Gly Ala Trp Val
        195                 200                 205

Val Lys Asp Trp Leu Asn Trp Trp Gly Gly Trp Ala Val Gly Glu Tyr
    210                 215                 220

Trp Asp Thr Asn Val Asp Ala Leu Leu Asn Trp Ala Tyr Ser Ser Gly
225                 230                 235                 240

Ala Lys Val Phe Asp Phe Pro Leu Tyr Tyr Lys Met Asp Glu Ala Phe
                245                 250                 255

Asp Asn Lys Asn Ile Pro Ala Leu Val Ser Ala Leu Gln Asn Gly Gln
            260                 265                 270

Thr Val Val Ser Arg Asp Pro Phe Lys Ala Val Thr Phe Val Ala Asn
        275                 280                 285
```

```
His Asp Thr Asp Ile Ile Trp Asn Lys Tyr Pro Ala Tyr Ala Phe Ile
    290                 295                 300
Leu Thr Tyr Glu Gly Gln Pro Thr Ile Phe Tyr Arg Asp Tyr Glu Glu
305                 310                 315                 320
Trp Leu Asn Lys Asp Lys Leu Lys Asn Leu Ile Trp Ile His Asp Asn
                325                 330                 335
Leu Ala Gly Gly Ser Thr Asp Ile Val Tyr Asp Asn Asp Glu Leu
                340                 345                 350
Ile Phe Val Arg Asn Gly Tyr Gly Ser Lys Pro Gly Leu Ile Thr Tyr
            355                 360                 365
Ile Asn Leu Ala Ser Ser Lys Ala Gly Arg Trp Val Tyr Val Pro Lys
370                 375                 380
Phe Ala Gly Ser Cys Ile His Glu Tyr Thr Gly Asn Leu Gly Gly Trp
385                 390                 395                 400
Val Asp Lys Trp Val Asp Ser Ser Gly Trp Val Tyr Leu Glu Ala Pro
                405                 410                 415
Ala His Asp Pro Ala Asn Gly Gln Tyr Gly Tyr Ser Val Trp Ser Tyr
                420                 425                 430
Cys Gly Val Gly
        435

<210> SEQ ID NO 26
<211> LENGTH: 436
<212> TYPE: PRT
<213> ORGANISM: Artificial Sequence
<220> FEATURE:
<223> OTHER INFORMATION: Synthetic protein

<400> SEQUENCE: 26

Met Ala Lys Tyr Ser Glu Leu Glu Glu Gly Gly Val Ile Met Gln Ala
1               5                   10                  15
Phe Tyr Trp Asp Val Pro Gly Gly Ile Trp Trp Asp Thr Ile Arg
                20                  25                  30
Ser Lys Ile Pro Glu Trp Tyr Glu Ala Gly Ile Ser Ala Ile Trp Ile
            35                  40                  45
Pro Pro Ala Ser Lys Gly Met Gly Gly Ala Tyr Ser Met Gly Tyr Asp
50                  55                  60
Pro Tyr Asp Phe Phe Asp Leu Gly Glu Tyr Asp Gln Lys Gly Thr Val
65                  70                  75                  80
Glu Thr Arg Phe Gly Ser Lys Gln Glu Leu Val Asn Met Ile Asn Thr
                85                  90                  95
Ala His Ala Tyr Gly Ile Lys Val Ile Ala Asp Ile Val Ile Asn His
                100                 105                 110
Arg Thr Gly Gly Asp Leu Glu Trp Asn Pro Phe Val Gly Asp Tyr Thr
            115                 120                 125
Trp Thr Asp Phe Ser Lys Val Ala Ser Gly Lys Tyr Thr Ala Asn Tyr
130                 135                 140
Leu Asp Phe His Pro Asn Glu Val Lys Cys Cys Asp Glu Gly Thr Phe
145                 150                 155                 160
Gly Gly Phe Pro Asp Ile Ala His Glu Lys Ser Trp Asp Gln His Trp
                165                 170                 175
Leu Trp Ala Ser Asp Glu Ser Tyr Ala Ala Tyr Leu Arg Ser Ile Gly
            180                 185                 190
Val Asp Ala Trp Arg Phe Asp Tyr Val Lys Gly Tyr Gly Ala Trp Val
        195                 200                 205
```

```
Val Lys Asp Trp Leu Asp Trp Trp Gly Gly Trp Ala Val Gly Glu Tyr
210                 215                 220

Trp Asp Thr Asn Val Asp Ala Leu Leu Asn Trp Ala Tyr Ser Ser Asp
225                 230                 235                 240

Ala Lys Val Phe Asp Phe Pro Leu Tyr Tyr Lys Met Asp Glu Ala Phe
                245                 250                 255

Asp Asn Lys Asn Ile Pro Ala Leu Val Ser Ala Leu Gln Asn Gly Gln
                260                 265                 270

Thr Val Val Ser Arg Asp Pro Phe Lys Ala Val Thr Phe Val Ala Asn
            275                 280                 285

His Asp Thr Asp Ile Ile Trp Asn Lys Tyr Pro Ala Tyr Ala Phe Ile
290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
                325                 330                 335

Leu Ala Gly Gly Ser Thr Asp Ile Val Tyr Tyr Asp Asn Asp Glu Leu
                340                 345                 350

Ile Phe Val Arg Asn Gly Tyr Gly Ser Lys Pro Gly Leu Ile Thr Tyr
            355                 360                 365

Ile Asn Leu Ala Ser Ser Lys Ala Gly Arg Trp Val Tyr Val Pro Lys
370                 375                 380

Phe Ala Gly Ala Cys Ile His Glu Tyr Thr Gly Asn Leu Gly Gly Trp
385                 390                 395                 400

Val Asp Lys Trp Val Asp Ser Ser Gly Trp Val Tyr Leu Glu Ala Pro
                405                 410                 415

Ala His Asp Pro Ala Asn Gly Tyr Tyr Gly Tyr Ser Val Trp Ser Tyr
                420                 425                 430

Cys Gly Val Gly
            435

<210> SEQ ID NO 27
<211> LENGTH: 436
<212> TYPE: PRT
<213> ORGANISM: Artificial Sequence
<220> FEATURE:
<223> OTHER INFORMATION: Synthetic protein

<400> SEQUENCE: 27

Met Ala Lys Tyr Leu Glu Leu Glu Glu Gly Gly Val Ile Met Gln Ala
1               5                   10                  15

Phe Tyr Trp Asp Val Pro Ser Gly Gly Ile Trp Trp Asp Thr Ile Arg
                20                  25                  30

Gln Lys Ile Pro Glu Trp Tyr Asp Ala Gly Ile Ser Ala Ile Trp Ile
            35                  40                  45

Pro Pro Ala Ser Lys Gly Met Gly Gly Ala Tyr Ser Met Gly Tyr Asp
50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Met Lys Val Ile Ala Asp Ile Val Ile Asn His
                100                 105                 110

Arg Ala Gly Gly Asp Leu Glu Trp Asn Pro Phe Val Asn Asp Tyr Thr
            115                 120                 125
```

```
Trp Thr Asp Phe Ser Lys Val Ala Ser Gly Lys Tyr Thr Ala Asn Tyr
    130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Gly Ala Trp Val
        195                 200                 205

Val Lys Asp Trp Leu Asn Trp Trp Gly Gly Trp Ala Val Gly Glu Tyr
210                 215                 220

Trp Asp Thr Asn Val Asp Ala Leu Leu Asn Trp Ala Tyr Ser Ser Gly
225                 230                 235                 240

Ala Lys Val Phe Asp Phe Pro Leu Tyr Tyr Lys Met Asp Glu Ala Phe
                245                 250                 255

Asp Asn Lys Asn Ile Pro Ala Leu Val Ser Ala Leu Gln Asn Gly Gln
                260                 265                 270

Thr Val Val Ser Arg Asp Pro Phe Lys Ala Val Thr Phe Val Ala Asn
            275                 280                 285

His Asp Thr Asp Ile Ile Trp Asn Lys Tyr Leu Ala Tyr Ala Phe Ile
        290                 295                 300

Leu Thr Tyr Glu Gly Gln Pro Val Ile Phe Tyr Arg Asp Tyr Glu Glu
305                 310                 315                 320

Trp Leu Asn Lys Asp Arg Leu Asn Asn Leu Ile Trp Ile His Asp His
                325                 330                 335

Leu Ala Gly Gly Ser Thr Ser Ile Val Tyr Tyr Asp Ser Asp Glu Met
            340                 345                 350

Ile Phe Val Arg Asn Gly Tyr Gly Ser Lys Pro Gly Leu Ile Thr Tyr
        355                 360                 365

Ile Asn Leu Gly Ser Ser Lys Val Gly Arg Trp Val Tyr Val Pro Lys
370                 375                 380

Phe Ala Gly Ser Cys Ile His Glu Tyr Thr Gly Asn Leu Gly Gly Trp
385                 390                 395                 400

Val Asp Lys Trp Val Asp Ser Ser Gly Trp Val Tyr Leu Glu Ala Pro
                405                 410                 415

Ala His Asp Pro Ala Asn Gly Gln Tyr Gly Tyr Ser Val Trp Ser Tyr
            420                 425                 430

Cys Gly Val Gly
        435

<210> SEQ ID NO 28
<211> LENGTH: 436
<212> TYPE: PRT
<213> ORGANISM: Artificial Sequence
<220> FEATURE:
<223> OTHER INFORMATION: Synthetic protein

<400> SEQUENCE: 28

Met Ala Lys Tyr Leu Glu Leu Glu Glu Ser Gly Val Ile Met Gln Ala
1               5                   10                  15

Phe Tyr Trp Asp Val Pro Ser Gly Gly Ile Trp Trp Asp Thr Ile Arg
            20                  25                  30

Gln Lys Ile Pro Glu Trp Tyr Asp Ala Gly Ile Ser Ala Ile Trp Ile
        35                  40                  45
```

Pro Pro Ala Ser Lys Gly Met Ser Gly Gly Tyr Ser Met Gly Tyr Asp
    50                  55                  60

Pro Tyr Asp Tyr Phe Asp Leu Gly Glu Tyr Tyr Gln Lys Gly Thr Val
65                  70                  75                  80

Glu Thr Arg Phe Gly Ser Lys Gln Glu Leu Ile Asn Met Ile Asn Thr
                85                  90                  95

Ala His Ala Tyr Gly Ile Lys Val Ile Ala Asp Ile Val Ile Asn His
            100                 105                 110

Arg Ala Gly Gly Asp Leu Glu Trp Asn Pro Phe Val Asn Asp Tyr Thr
        115                 120                 125

Trp Thr Asp Phe Ser Lys Val Ala Ser Gly Lys Tyr Thr Ala Asn Tyr
130                 135                 140

Leu Asp Phe His Pro Asn Glu Val Lys Cys Cys Asp Glu Gly Thr Phe
145                 150                 155                 160

Gly Gly Phe Pro Asp Ile Ala His Glu Lys Ser Trp Asp Gln His Trp
                165                 170                 175

Leu Trp Ala Ser Asp Glu Ser Tyr Ala Ala Tyr Leu Arg Ser Ile Gly
            180                 185                 190

Val Asp Ala Trp Arg Phe Asp Tyr Val Lys Gly Tyr Gly Ala Trp Val
        195                 200                 205

Val Lys Asp Trp Leu Asn Trp Trp Gly Gly Trp Ala Val Gly Glu Tyr
210                 215                 220

Trp Asp Thr Asn Val Asp Ala Leu Leu Asn Trp Ala Tyr Ser Ser Asp
225                 230                 235                 240

Ala Lys Val Phe Asp Phe Pro Leu Tyr Tyr Lys Met Asp Glu Ala Phe
                245                 250                 255

Asp Asn Asn Asn Ile Pro Ala Leu Val Asp Ala Leu Arg Tyr Gly Gln
            260                 265                 270

Thr Val Val Ser Arg Asp Pro Phe Lys Ala Val Thr Phe Val Ala Asn
        275                 280                 285

His Asp Thr Asp Ile Ile Trp Asn Lys Tyr Leu Ala Tyr Ala Phe Ile
290                 295                 300

Leu Thr Tyr Glu Gly Gln Pro Val Ile Phe Tyr Arg Asp Tyr Glu Glu
305                 310                 315                 320

Trp Leu Asn Lys Asp Arg Leu Asn Asn Leu Ile Trp Ile His Asp His
                325                 330                 335

Leu Ala Gly Gly Ser Thr Asp Ile Val Tyr Tyr Asp Asn Asp Glu Leu
            340                 345                 350

Ile Phe Val Arg Asn Gly Tyr Gly Ser Lys Pro Gly Leu Ile Thr Tyr
        355                 360                 365

Ile Asn Leu Ala Ser Ser Lys Ala Gly Arg Trp Val Tyr Val Pro Lys
370                 375                 380

Phe Ala Gly Ala Cys Ile His Glu Tyr Thr Gly Asn Leu Gly Gly Trp
385                 390                 395                 400

Val Asp Lys Trp Val Asp Ser Ser Gly Trp Val Tyr Leu Glu Ala Pro
                405                 410                 415

Ala His Asp Pro Ala Asn Gly Tyr Tyr Gly Tyr Ser Val Trp Ser Tyr
            420                 425                 430

Cys Gly Val Gly
        435

<210> SEQ ID NO 29
<211> LENGTH: 436
<212> TYPE: PRT

<213> ORGANISM: Artificial Sequence
<220> FEATURE:
<223> OTHER INFORMATION: Synthetic protein

<400> SEQUENCE: 29

```
Met Ala Lys Tyr Leu Glu Leu Glu Glu Gly Val Ile Met Gln Ala
1               5                   10                  15

Phe Tyr Trp Asp Val Pro Ser Gly Gly Ile Trp Trp Asp Thr Ile Arg
            20                  25                  30

Gln Lys Ile Pro Glu Trp Tyr Asp Ala Gly Ile Ser Ala Ile Trp Ile
        35                  40                  45

Pro Pro Ala Ser Lys Gly Met Ser Gly Gly Tyr Ser Met Gly Tyr Asp
50                  55                  60

Pro Tyr Asp Tyr Phe Asp Leu Gly Glu Tyr Tyr Gln Lys Gly Thr Val
65                  70                  75                  80

Glu Thr Arg Phe Gly Ser Lys Gln Glu Leu Ile Asn Met Ile Asn Thr
                85                  90                  95

Ala His Ala Tyr Gly Ile Lys Val Ile Ala Asp Ile Val Ile Asn His
            100                 105                 110

Arg Ala Gly Gly Asp Leu Glu Trp Asn Pro Phe Val Asn Asp Tyr Thr
            115                 120                 125

Trp Thr Asp Phe Ser Lys Val Ala Ser Gly Lys Tyr Thr Ala Asn Tyr
130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Ala Pro Trp Val
            195                 200                 205

Val Lys Asp Trp Leu Asn Trp Trp Gly Gly Trp Ala Val Gly Glu Tyr
            210                 215                 220

Trp Asp Thr Asn Val Asp Ala Val Leu Asn Trp Ala Tyr Ser Ser Gly
225                 230                 235                 240

Ala Lys Val Phe Asp Phe Ala Leu Tyr Tyr Lys Met Asp Glu Ala Phe
                245                 250                 255

Asp Asn Asn Asn Ile Pro Ala Leu Val Asp Ala Leu Arg Tyr Gly Gln
            260                 265                 270

Thr Val Val Ser Arg Asp Pro Phe Lys Ala Val Thr Phe Val Ala Asn
            275                 280                 285

His Asp Thr Asp Ile Ile Trp Asn Lys Tyr Pro Ala Tyr Ala Phe Ile
290                 295                 300

Leu Thr Tyr Glu Gly Gln Pro Thr Ile Phe Tyr Arg Asp Tyr Glu Glu
305                 310                 315                 320

Trp Leu Asn Lys Asp Arg Leu Lys Asn Leu Ile Trp Ile His Asp His
                325                 330                 335

Leu Ala Gly Gly Ser Thr Asp Ile Val Tyr Tyr Asp Asn Asp Glu Leu
            340                 345                 350

Ile Phe Val Arg Asn Gly Tyr Gly Ser Lys Pro Gly Leu Ile Thr Tyr
            355                 360                 365

Ile Asn Leu Ala Ser Ser Lys Ala Gly Arg Trp Val Tyr Val Pro Lys
370                 375                 380

Phe Ala Gly Ala Cys Ile His Glu Tyr Thr Gly Asn Leu Gly Gly Trp
```

```
                385                 390                 395                 400
Val Asp Lys Tyr Val Tyr Ser Ser Gly Trp Val Tyr Leu Glu Ala Pro
                    405                 410                 415

Ala Tyr Asp Pro Ala Asn Gly Gln Tyr Gly Tyr Ser Val Trp Ser Tyr
                420                 425                 430

Cys Gly Val Gly
        435

<210> SEQ ID NO 30
<211> LENGTH: 436
<212> TYPE: PRT
<213> ORGANISM: Artificial Sequence
<220> FEATURE:
<223> OTHER INFORMATION: Synthetic protein

<400> SEQUENCE: 30

Met Ala Lys Tyr Ser Glu Leu Lys Lys Gly Gly Val Ile Met Gln Ala
1               5                   10                  15

Phe Tyr Trp Asp Val Pro Ser Gly Gly Ile Trp Asp Thr Ile Arg
            20                  25                  30

Gln Lys Ile Pro Glu Trp Tyr Glu Ala Gly Ile Ser Ala Ile Trp Ile
                35                  40                  45

Pro Pro Ala Ser Lys Gly Met Ser Gly Gly Tyr Ser Met Gly Tyr Asp
    50                  55                  60

Pro Tyr Asp Tyr Phe Asp Leu Gly Glu Tyr Tyr Gln Lys Gly Thr Val
65                  70                  75                  80

Glu Thr Arg Phe Gly Ser Lys Gln Glu Leu Ile Asn Met Ile Asn Thr
                85                  90                  95

Ala His Ala Tyr Gly Ile Lys Val Ile Ala Asp Ile Val Ile Asn His
                100                 105                 110

Arg Ala Gly Gly Asp Leu Glu Trp Asn Pro Phe Val Asn Asp Tyr Thr
            115                 120                 125

Trp Thr Asp Phe Ser Lys Val Ala Ser Gly Lys Tyr Thr Ala Asn Tyr
            130                 135                 140

Leu Asn Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Gly Ala Trp Val
            195                 200                 205

Val Lys Asp Trp Leu Asp Trp Trp Gly Gly Trp Ala Val Gly Glu Tyr
        210                 215                 220

Trp Asp Thr Asn Val Asp Ala Leu Leu Asn Trp Ala Tyr Ser Ser Asp
225                 230                 235                 240

Ala Lys Val Phe Asp Phe Pro Leu Tyr Tyr Lys Met Asp Glu Ala Phe
                245                 250                 255

Asp Asn Lys Asn Ile Pro Ala Leu Val Ser Ala Leu Gln Asn Gly Gln
            260                 265                 270

Thr Val Val Ser Arg Asp Pro Phe Lys Ala Val Thr Phe Val Ala Asn
        275                 280                 285

His Asp Thr Asp Ile Ile Trp Asn Lys Tyr Pro Ala Tyr Ala Phe Ile
    290                 295                 300

Leu Thr Tyr Glu Gly Gln Pro Thr Ile Phe Tyr Arg Asp Tyr Glu Glu
```

```
                305                 310                 315                 320
Trp Leu Asn Lys Asp Lys Leu Lys Asn Leu Ile Trp Ile His Asp Asn
                325                 330                 335
Leu Ala Gly Gly Ser Thr Asp Ile Val Tyr Tyr Asp Asn Asp Glu Leu
                340                 345                 350
Ile Phe Val Arg Asn Gly Tyr Gly Asp Lys Pro Gly Leu Ile Thr Tyr
                355                 360                 365
Ile Asn Leu Gly Ser Ser Lys Ala Gly Arg Trp Val Tyr Val Pro Lys
                370                 375                 380
Phe Ala Gly Ala Cys Ile His Glu Tyr Thr Gly Asn Leu Gly Gly Trp
385                 390                 395                 400
Val Asp Lys Trp Val Asp Ser Ser Gly Trp Val Tyr Leu Glu Ala Pro
                405                 410                 415
Ala His Asp Pro Ala Asn Gly Tyr Tyr Gly Tyr Ser Val Trp Ser Tyr
                420                 425                 430
Cys Gly Val Gly
                435

<210> SEQ ID NO 31
<211> LENGTH: 436
<212> TYPE: PRT
<213> ORGANISM: Artificial Sequence
<220> FEATURE:
<223> OTHER INFORMATION: Synthetic protein

<400> SEQUENCE: 31

Met Ala Lys Tyr Leu Glu Leu Glu Glu Gly Gly Val Ile Met Gln Ala
1               5                   10                  15
Phe Tyr Trp Asp Val Pro Ser Gly Gly Ile Trp Trp Asp Thr Ile Arg
                20                  25                  30
Gln Lys Ile Pro Glu Trp Tyr Asp Ala Gly Ile Ser Ala Ile Trp Ile
                35                  40                  45
Pro Pro Ala Ser Lys Gly Met Gly Gly Ala Tyr Ser Met Gly Tyr Asp
                50                  55                  60
Pro Tyr Asp Phe Phe Asp Leu Gly Glu Tyr Asp Gln Lys Gly Thr Val
65                  70                  75                  80
Glu Thr Arg Phe Gly Ser Lys Gln Glu Leu Val Asn Met Ile Asn Thr
                85                  90                  95
Ala His Ala Tyr Gly Ile Lys Ala Ile Ala Asp Ile Val Ile Asn His
                100                 105                 110
Arg Ala Gly Gly Asp Leu Glu Trp Asn Pro Phe Val Gly Asp Tyr Thr
                115                 120                 125
Trp Thr Asp Phe Ser Lys Val Ala Ser Gly Lys Tyr Thr Ala Asn Tyr
                130                 135                 140
Leu Asp Phe His Pro Asn Glu Val Lys Cys Cys Asp Glu Gly Thr Phe
145                 150                 155                 160
Gly Gly Phe Pro Asp Ile Ala His Glu Lys Ser Trp Asp Gln His Trp
                165                 170                 175
Leu Trp Ala Ser Asp Glu Ser Tyr Ala Ala Tyr Leu Arg Ser Ile Gly
                180                 185                 190
Val Asp Ala Trp Arg Phe Asp Tyr Val Lys Gly Tyr Gly Ala Trp Val
                195                 200                 205
Val Lys Asp Trp Leu Asn Trp Trp Gly Gly Trp Ala Val Gly Glu Tyr
                210                 215                 220
Trp Asp Thr Asn Val Asp Ala Leu Leu Asn Trp Ala Tyr Ser Ser Gly
```

```
                225                 230                 235                 240
Ala Lys Val Phe Asp Phe Pro Leu Tyr Tyr Lys Met Asp Ala Ala Phe
                        245                 250                 255

Asp Asn Lys Asn Ile Pro Ala Leu Val Glu Ala Leu Lys Asn Gly Gly
                        260                 265                 270

Thr Val Val Ser Arg Asp Pro Phe Lys Ala Val Thr Phe Val Ala Asn
                275                 280                 285

His Asp Thr Asp Ile Ile Trp Asn Lys Tyr Pro Ala Tyr Ala Phe Ile
            290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
                325                 330                 335

Leu Ala Gly Gly Ser Thr Asp Ile Val Tyr Tyr Asp Asn Asp Glu Leu
                340                 345                 350

Ile Phe Val Arg Asn Gly Tyr Gly Asp Lys Pro Gly Leu Ile Thr Tyr
                355                 360                 365

Ile Asn Leu Gly Trp Ser Lys Ala Gly Arg Trp Val Tyr Val Pro Lys
    370                 375                 380

Phe Ala Gly Ala Cys Ile His Glu Tyr Thr Gly Asn Leu Gly Gly Trp
385                 390                 395                 400

Val Asp Lys Tyr Val Tyr Ser Ser Gly Trp Val Tyr Leu Glu Ala Pro
                405                 410                 415

Ala Tyr Asp Pro Ala Asn Gly Gln Tyr Gly Tyr Ser Val Trp Ser Tyr
                420                 425                 430

Cys Gly Val Gly
        435

<210> SEQ ID NO 32
<211> LENGTH: 436
<212> TYPE: PRT
<213> ORGANISM: Artificial Sequence
<220> FEATURE:
<223> OTHER INFORMATION: Synthetic protein

<400> SEQUENCE: 32

Met Ala Lys Tyr Ser Glu Leu Glu Glu Gly Gly Val Ile Met Gln Ala
1               5                   10                  15

Phe Tyr Trp Asp Val Pro Gly Gly Gly Ile Trp Trp Gly Thr Ile Arg
                20                  25                  30

Ser Lys Ile Pro Glu Trp Tyr Glu Ala Gly Ile Ser Ala Ile Trp Ile
            35                  40                  45

Pro Pro Ala Ser Lys Gly Met Ser Gly Gly Tyr Ser Met Gly Tyr Asp
        50                  55                  60

Pro Tyr Asp Tyr Phe Asp Leu Gly Glu Tyr Tyr Gln Lys Gly Thr Val
65                  70                  75                  80

Glu Thr Arg Phe Gly Ser Lys Gln Glu Leu Ile Asn Met Ile Asn Thr
                85                  90                  95

Ala His Ala Tyr Gly Met Lys Val Ile Ala Asp Ile Val Ile Asn His
            100                 105                 110

Arg Ala Gly Gly Asp Leu Glu Trp Asn Pro Phe Val Asn Asp Tyr Thr
        115                 120                 125

Trp Thr Asp Phe Ser Lys Val Ala Ser Gly Lys Tyr Thr Ala Asn Tyr
    130                 135                 140

Leu Asp Phe His Pro Asn Glu Leu His Ala Gly Asp Ser Gly Thr Phe
```

```
                145                 150                 155                 160
        Gly Gly Tyr Pro Asp Ile Cys His Asp Lys Ser Trp Asp Gln Tyr Trp
                    165                 170                 175

Leu Trp Ala Ser Gln Glu Ser Tyr Ala Ala Tyr Leu Arg Ser Ile Gly
                    180                 185                 190

Ile Asp Ala Trp Arg Phe Asp Tyr Val Lys Gly Tyr Ala Pro Trp Val
                    195                 200                 205

Val Lys Asp Trp Leu Asn Trp Trp Gly Gly Trp Ala Val Gly Glu Tyr
                    210                 215                 220

Trp Asp Thr Asn Val Asp Ala Val Leu Asn Trp Ala Tyr Ser Ser Gly
        225                 230                 235                 240

Ala Lys Val Phe Asp Phe Ala Leu Tyr Tyr Lys Met Asp Glu Ala Phe
                    245                 250                 255

Asp Asn Asn Asn Ile Pro Ala Leu Val Asp Ala Leu Arg Tyr Gly Gln
                    260                 265                 270

Thr Val Val Ser Arg Asp Pro Phe Lys Ala Val Thr Phe Val Ala Asn
                    275                 280                 285

His Asp Thr Asp Ile Ile Trp Asn Lys Tyr Pro Ala Tyr Ala Phe Ile
                    290                 295                 300

Leu Thr Tyr Glu Gly Gln Pro Thr Ile Phe Tyr Arg Asp Tyr Glu Glu
        305                 310                 315                 320

Trp Leu Asn Lys Asp Arg Leu Lys Asn Leu Ile Trp Ile His Asp His
                    325                 330                 335

Leu Ala Gly Gly Ser Thr Ser Ile Val Tyr Tyr Asp Ser Asp Glu Met
                    340                 345                 350

Ile Phe Val Arg Asn Gly Tyr Gly Ser Lys Pro Gly Leu Ile Thr Tyr
                    355                 360                 365

Ile Asn Leu Gly Ser Ser Lys Val Gly Arg Trp Val Tyr Val Pro Lys
                    370                 375                 380

Phe Ala Gly Ser Cys Ile His Glu Tyr Thr Gly Asn Leu Gly Gly Trp
        385                 390                 395                 400

Val Asp Lys Trp Val Asp Ser Ser Gly Trp Val Tyr Leu Glu Ala Pro
                    405                 410                 415

Ala His Asp Pro Ala Asn Gly Gln Tyr Gly Tyr Ser Val Trp Ser Tyr
                    420                 425                 430

Cys Gly Val Gly
                    435

<210> SEQ ID NO 33
<211> LENGTH: 436
<212> TYPE: PRT
<213> ORGANISM: Artificial Sequence
<220> FEATURE:
<223> OTHER INFORMATION: Synthetic protein

<400> SEQUENCE: 33

Met Ala Lys Tyr Leu Glu Leu Glu Glu Gly Gly Val Ile Met Gln Ala
1               5                   10                  15

Phe Tyr Trp Asp Val Pro Ser Gly Gly Ile Trp Trp Asp Thr Ile Arg
                20                  25                  30

Gln Lys Ile Pro Glu Trp Tyr Asp Ala Gly Ile Ser Ala Ile Trp Ile
            35                  40                  45

Pro Pro Ala Ser Lys Gly Met Ser Gly Gly Tyr Ser Met Gly Tyr Asp
        50                  55                  60

Pro Tyr Asp Tyr Phe Asp Leu Gly Glu Tyr Tyr Gln Lys Gly Thr Val
```

Glu Thr Arg Phe Gly Ser Lys Gln Glu Leu Ile Asn Met Ile Asn Thr
65                  70                  75                  80

Ala His Ala Tyr Gly Ile Lys Val Ile Ala Asp Ile Val Ile Asn His
            85                  90                  95

Arg Ala Gly Gly Asp Leu Glu Trp Asn Pro Phe Val Gly Asp Tyr Thr
        100                 105                 110

Trp Thr Asp Phe Ser Lys Val Ala Ser Gly Lys Tyr Thr Ala Asn Tyr
    115                 120                 125

Leu Asp Phe His Pro Asn Glu Val Lys Cys Cys Asp Glu Gly Thr Phe
130                 135                 140

Gly Gly Phe Pro Asp Ile Ala His Glu Lys Ser Trp Asp Gln His Trp
            145                 150                 155                 160

Leu Trp Ala Ser Asp Glu Ser Tyr Ala Ala Tyr Leu Arg Ser Ile Gly
        165                 170                 175

Val Asp Ala Trp Arg Phe Asp Tyr Val Lys Gly Tyr Gly Ala Trp Val
    180                 185                 190

Val Lys Asp Trp Leu Asp Trp Trp Gly Gly Trp Ala Val Gly Glu Tyr
195                 200                 205

Trp Asp Thr Asn Val Asp Ala Leu Leu Asn Trp Ala Tyr Ser Ser Asp
225                 210                 215                 220

Ala Lys Val Phe Asp Phe Pro Leu Tyr Tyr Lys Met Asp Glu Ala Phe
        230                 235                 240

Asp Asn Asn Asn Ile Pro Ala Leu Val Asp Ala Leu Arg Tyr Gly Gln
    245                 250                 255

Thr Val Val Ser Arg Asp Pro Phe Lys Ala Val Thr Phe Val Ala Asn
260                 265                 270

His Asp Thr Asp Ile Ile Trp Asn Lys Tyr Pro Ala Tyr Ala Phe Ile
        275                 280                 285

Leu Thr Tyr Glu Gly Gln Pro Thr Ile Phe Tyr Arg Asp Tyr Glu Glu
    290                 295                 300

Trp Leu Asn Lys Asp Lys Leu Lys Asn Leu Ile Trp Ile His Asp Asn
305                 310                 315                 320

Leu Ala Gly Gly Ser Thr Ser Ile Val Tyr Tyr Asp Ser Asp Glu Met
        325                 330                 335

Ile Phe Val Arg Asn Gly Tyr Gly Ser Lys Pro Gly Leu Ile Thr Tyr
    340                 345                 350

Ile Asn Leu Gly Ser Ser Lys Val Gly Arg Trp Val Tyr Val Pro Lys
355                 360                 365

Phe Ala Gly Ala Cys Ile His Glu Tyr Thr Gly Asn Leu Gly Gly Trp
385                 370                 375                 380

Val Asp Lys Trp Val Asp Ser Ser Gly Trp Val Tyr Leu Glu Ala Pro
        390                 395                 400

Ala His Asp Pro Ala Asn Gly Tyr Tyr Gly Tyr Ser Val Trp Ser Tyr
    405                 410                 415

Cys Val Val Gly
        420                 425                 430

435

<210> SEQ ID NO 34
<211> LENGTH: 436
<212> TYPE: PRT
<213> ORGANISM: Artificial Sequence
<220> FEATURE:
<223> OTHER INFORMATION: Synthetic protein

```
<400> SEQUENCE: 34

Met Ala Lys Tyr Leu Glu Leu Glu Glu Gly Val Ile Met Gln Ala
1               5                   10                  15

Phe Tyr Trp Asp Val Pro Ser Gly Gly Ile Trp Asp Thr Ile Arg
                20                  25                  30

Gln Lys Ile Pro Glu Trp Tyr Asp Ala Gly Ile Ser Ala Ile Trp Ile
            35                  40                  45

Pro Pro Ala Ser Lys Gly Met Gly Gly Ala Tyr Ser Met Gly Tyr Asp
50                      55                      60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Ile Lys Val Ile Ala Asp Ile Val Ile Asn His
                100                 105                 110

Arg Ala Gly Gly Asp Leu Glu Trp Asn Pro Phe Val Gly Asp Tyr Thr
                115                 120                 125

Trp Thr Asp Phe Ser Lys Val Ala Ser Gly Lys Tyr Thr Ala Asn Tyr
130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
                180                 185                 190

Ile Asp Ala Trp Arg Phe Asp Tyr Val Lys Gly Tyr Ala Pro Trp Val
            195                 200                 205

Val Lys Asp Trp Leu Asn Trp Trp Gly Gly Trp Ala Val Gly Glu Tyr
210                 215                 220

Trp Asp Thr Asn Val Asp Ala Val Leu Asn Trp Ala Tyr Ser Ser Gly
225                 230                 235                 240

Ala Lys Val Phe Asp Phe Ala Leu Tyr Tyr Lys Met Asp Glu Ala Phe
                245                 250                 255

Asp Asn Lys Asn Ile Pro Ala Leu Val Ser Ala Leu Gln Asn Gly Gln
                260                 265                 270

Thr Val Val Ser Arg Asp Pro Phe Lys Ala Val Thr Phe Val Ala Asn
                275                 280                 285

His Asp Thr Asp Ile Ile Trp Asn Lys Tyr Pro Ala Tyr Ala Phe Ile
290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
                325                 330                 335

Leu Ala Gly Gly Ser Thr Asp Ile Val Tyr Tyr Asp Asn Asp Glu Leu
                340                 345                 350

Ile Phe Val Arg Asn Gly Tyr Gly Ser Lys Pro Gly Leu Ile Thr Tyr
                355                 360                 365

Ile Asn Leu Ala Ser Ser Lys Ala Gly Arg Trp Val Tyr Val Pro Lys
370                 375                 380

Phe Ala Gly Ala Cys Ile His Glu Tyr Thr Gly Asn Leu Gly Gly Trp
385                 390                 395                 400

Val Asp Lys Tyr Val Tyr Ser Ser Gly Trp Val Tyr Leu Glu Ala Pro
                405                 410                 415
```

Ala Tyr Asp Pro Ala Asn Gly Gln Tyr Gly Tyr Ser Val Trp Ser Tyr
            420                 425                 430

Cys Gly Val Gly
        435

<210> SEQ ID NO 35
<211> LENGTH: 432
<212> TYPE: PRT
<213> ORGANISM: Artificial Sequence
<220> FEATURE:
<223> OTHER INFORMATION: Synthetic protein

<400> SEQUENCE: 35

Met Ala Leu Glu Glu Gly Gly Leu Ile Met Gln Ala Phe Tyr Trp Asp
1               5                   10                  15

Val Pro Gly Gly Gly Ile Trp Trp Asp Thr Ile Ala Gln Lys Ile Pro
            20                  25                  30

Asp Trp Ala Ser Ala Gly Ile Ser Ala Ile Trp Ile Pro Pro Ala Ser
        35                  40                  45

Lys Gly Met Ser Gly Gly Tyr Ser Met Gly Tyr Asp Pro Tyr Asp Phe
    50                  55                  60

Phe Asp Leu Gly Glu Tyr Tyr Gln Lys Gly Ser Val Glu Thr Arg Phe
65                  70                  75                  80

Gly Ser Lys Glu Glu Leu Val Asn Met Ile Asn Thr Ala His Ala His
                85                  90                  95

Asn Met Lys Val Ile Ala Asp Ile Val Ile Asn His Arg Ala Gly Gly
            100                 105                 110

Asp Leu Glu Trp Asn Pro Phe Thr Asn Ser Tyr Thr Trp Thr Asp Phe
        115                 120                 125

Ser Lys Val Ala Ser Gly Lys Tyr Thr Ala Asn Tyr Leu Asp Phe His
    130                 135                 140

Pro Asn Glu Leu His Ala Gly Asp Ser Gly Thr Phe Gly Gly Tyr Pro
145                 150                 155                 160

Asp Ile Cys His Asp Lys Ser Trp Asp Gln His Trp Leu Trp Ala Ser
                165                 170                 175

Asn Glu Ser Tyr Ala Ala Tyr Leu Arg Ser Ile Gly Ile Asp Ala Trp
            180                 185                 190

Arg Phe Asp Tyr Val Lys Gly Tyr Ala Pro Trp Val Val Lys Asn Trp
        195                 200                 205

Leu Asn Arg Trp Gly Gly Trp Ala Val Gly Glu Tyr Trp Asp Thr Asn
    210                 215                 220

Val Asp Ala Leu Leu Ser Trp Ala Tyr Asp Ser Gly Ala Lys Val Phe
225                 230                 235                 240

Asp Phe Pro Leu Tyr Tyr Lys Met Asp Glu Ala Phe Asp Asn Asn Asn
                245                 250                 255

Ile Pro Ala Leu Val Asp Ala Leu Lys Asn Gly Gly Thr Val Val Ser
            260                 265                 270

Arg Asp Pro Phe Lys Ala Val Thr Phe Val Ala Asn His Asp Thr Asn
        275                 280                 285

Ile Ile Trp Asn Lys Tyr Pro Ala Tyr Ala Phe Ile Leu Thr Tyr Glu
    290                 295                 300

Gly Gln Pro Ala Ile Phe Tyr Arg Asp Tyr Glu Glu Trp Leu Asn Lys
305                 310                 315                 320

Asp Arg Leu Arg Asn Leu Ile Trp Ile His Asp His Leu Ala Gly Gly
                325                 330                 335

```
Ser Thr Asp Ile Ile Tyr Tyr Asp Ser Asp Glu Leu Ile Phe Val Arg
            340                 345                 350

Asn Gly Tyr Gly Asp Lys Pro Gly Leu Ile Thr Tyr Ile Asn Leu Gly
            355                 360                 365

Ser Ser Lys Ala Gly Arg Trp Val Tyr Val Pro Lys Phe Ala Gly Ser
        370                 375                 380

Cys Ile His Glu Tyr Thr Gly Asn Leu Gly Gly Trp Ile Asp Lys Trp
385                 390                 395                 400

Val Asp Ser Ser Gly Arg Val Tyr Leu Glu Ala Pro Ala His Asp Pro
                405                 410                 415

Ala Asn Gly Gln Tyr Gly Tyr Ser Val Trp Ser Tyr Cys Gly Val Gly
            420                 425                 430

<210> SEQ ID NO 36
<211> LENGTH: 432
<212> TYPE: PRT
<213> ORGANISM: Artificial Sequence
<220> FEATURE:
<223> OTHER INFORMATION: Synthetic protein

<400> SEQUENCE: 36

Met Ala Leu Glu Glu Gly Gly Leu Ile Met Gln Ala Phe Tyr Trp Asp
1               5                   10                  15

Val Pro Met Gly Gly Ile Trp Trp Asp Thr Ile Ala Gln Lys Ile Pro
            20                  25                  30

Asp Trp Ala Ser Ala Gly Ile Ser Ala Ile Trp Ile Pro Pro Ala Ser
        35                  40                  45

Lys Gly Met Ser Gly Gly Tyr Ser Met Gly Tyr Asp Pro Tyr Asp Tyr
50                  55                  60

Phe Asp Leu Gly Glu Tyr Tyr Gln Lys Gly Thr Val Glu Thr Arg Phe
65                  70                  75                  80

Gly Ser Lys Gln Glu Leu Ile Asn Met Ile Asn Thr Ala His Ala Tyr
                85                  90                  95

Gly Met Lys Val Ile Ala Asp Ile Val Ile Asn His Arg Ala Gly Gly
            100                 105                 110

Asp Leu Glu Trp Asn Pro Phe Val Asn Asp Tyr Thr Trp Thr Asp Phe
        115                 120                 125

Ser Lys Val Ala Ser Gly Lys Tyr Thr Ala Asn Tyr Leu Asp Phe His
130                 135                 140

Pro Asn Glu Leu His Ala Gly Asp Ser Gly Thr Phe Gly Gly Tyr Pro
145                 150                 155                 160

Asp Ile Cys His Asp Lys Ser Trp Asp Gln Tyr Trp Leu Trp Ala Ser
                165                 170                 175

Gln Glu Ser Tyr Ala Ala Tyr Leu Arg Ser Ile Gly Ile Asp Ala Trp
            180                 185                 190

Arg Phe Asp Tyr Val Lys Gly Tyr Ala Pro Trp Val Val Arg Asp Trp
        195                 200                 205

Leu Asn Trp Trp Gly Gly Trp Ala Val Gly Glu Tyr Trp Asp Thr Asn
    210                 215                 220

Val Asp Ala Val Leu Asn Trp Ala Tyr Ser Ser Gly Ala Lys Val Phe
225                 230                 235                 240

Asp Phe Ala Leu Tyr Tyr Lys Met Asp Glu Ala Phe Asp Asn Asn Asn
                245                 250                 255

Ile Pro Ala Leu Val Asp Ala Leu Arg Tyr Gly Gln Thr Val Val Ser
            260                 265                 270
```

-continued

```
Arg Asp Pro Phe Lys Ala Val Thr Phe Val Ala Asn His Asp Thr Asp
        275                 280                 285

Ile Ile Trp Asn Lys Tyr Pro Ala Tyr Ala Phe Ile Leu Thr Tyr Glu
    290                 295                 300

Gly Gln Pro Thr Ile Phe Tyr Arg Asp Tyr Glu Glu Trp Leu Asn Lys
305                 310                 315                 320

Asp Lys Leu Lys Asn Leu Ile Trp Ile His Asp Asn Leu Ala Gly Gly
                325                 330                 335

Ser Thr Asp Ile Val Tyr Tyr Asp Asn Asp Glu Leu Ile Phe Val Arg
            340                 345                 350

Asn Gly Tyr Gly Ser Lys Pro Gly Leu Ile Thr Tyr Ile Asn Leu Gly
        355                 360                 365

Ser Ser Lys Ala Gly Arg Trp Val Tyr Val Pro Lys Phe Ala Gly Ser
370                 375                 380

Cys Ile His Glu Tyr Thr Gly Asn Leu Gly Gly Trp Val Asp Lys Trp
385                 390                 395                 400

Val Asp Ser Ser Gly Trp Val Tyr Leu Glu Ala Pro Ala His Asp Pro
                405                 410                 415

Ala Asn Gly Gln Tyr Gly Tyr Ser Val Trp Ser Tyr Cys Gly Val Gly
            420                 425                 430

<210> SEQ ID NO 37
<211> LENGTH: 432
<212> TYPE: PRT
<213> ORGANISM: Artificial Sequence
<220> FEATURE:
<223> OTHER INFORMATION: Synthetic protein

<400> SEQUENCE: 37

Met Ala Leu Glu Glu Gly Gly Leu Ile Met Gln Ala Phe Tyr Trp Asp
1               5                   10                  15

Val Pro Met Gly Gly Ile Trp Trp Asp Thr Ile Ala Gln Lys Ile Pro
            20                  25                  30

Asp Trp Ala Ser Ala Gly Ile Ser Ala Ile Trp Ile Pro Pro Ala Ser
        35                  40                  45

Lys Gly Met Ser Gly Gly Tyr Ser Met Gly Tyr Asp Pro Tyr Asp Tyr
    50                  55                  60

Phe Asp Leu Gly Glu Tyr Tyr Gln Lys Gly Thr Val Glu Thr Arg Phe
65                  70                  75                  80

Gly Ser Lys Gln Glu Leu Ile Asn Met Ile Asn Thr Ala His Ala Tyr
                85                  90                  95

Gly Met Lys Val Ile Ala Asp Ile Val Ile Asn His Arg Ala Gly Gly
            100                 105                 110

Asp Leu Glu Trp Asn Pro Phe Val Asn Asp Tyr Thr Trp Thr Asp Phe
        115                 120                 125

Ser Lys Val Ala Ser Gly Lys Tyr Thr Ala Asn Tyr Leu Asp Phe His
    130                 135                 140

Pro Asn Glu Leu His Ala Gly Asp Ser Gly Thr Phe Gly Gly Tyr Pro
145                 150                 155                 160

Asp Ile Cys His Asp Lys Ser Trp Asp Gln Tyr Trp Leu Trp Ala Ser
                165                 170                 175

Gln Glu Ser Tyr Ala Ala Tyr Leu Arg Ser Ile Gly Ile Asp Ala Trp
            180                 185                 190

Arg Phe Asp Tyr Val Lys Gly Tyr Ala Pro Trp Val Val Lys Asp Trp
        195                 200                 205
```

```
Leu Asn Trp Trp Gly Gly Trp Ala Val Gly Glu Tyr Trp Asp Thr Asn
    210                 215                 220

Val Asp Ala Val Leu Asn Trp Ala Tyr Ser Ser Gly Ala Lys Val Phe
225                 230                 235                 240

Asp Phe Ala Leu Tyr Tyr Lys Met Asp Glu Ala Phe Asp Asn Asn Asn
                245                 250                 255

Ile Pro Ala Leu Val Asp Ala Leu Arg Tyr Gly Gln Thr Val Val Ser
                260                 265                 270

Arg Asp Pro Phe Lys Ala Val Thr Phe Val Ala Asn His Asp Thr Asp
            275                 280                 285

Ile Ile Trp Asn Lys Tyr Pro Ala Tyr Ala Phe Ile Leu Thr Tyr Glu
        290                 295                 300

Gly Gln Pro Thr Ile Phe Tyr Arg Asp Tyr Glu Glu Trp Leu Asn Lys
305                 310                 315                 320

Asp Lys Leu Lys Asn Leu Ile Trp Ile His Asp Asn Leu Ala Gly Gly
                325                 330                 335

Ser Thr Asp Ile Val Tyr Tyr Asp Asn Asp Glu Leu Ile Phe Val Arg
                340                 345                 350

Asn Gly Tyr Gly Ser Lys Pro Gly Leu Ile Thr Tyr Ile Asn Leu Ala
            355                 360                 365

Ser Ser Lys Ala Gly Arg Trp Val Tyr Val Pro Lys Phe Ala Gly Ser
370                 375                 380

Cys Ile His Glu Tyr Thr Gly Asn Leu Gly Gly Trp Val Asp Lys Trp
385                 390                 395                 400

Val Asp Ser Ser Gly Trp Val Tyr Leu Glu Ala Pro Ala His Asp Pro
                405                 410                 415

Ala Asn Gly Gln Tyr Gly Tyr Ser Val Trp Ser Tyr Cys Gly Val Gly
            420                 425                 430
```

<210> SEQ ID NO 38
<211> LENGTH: 461
<212> TYPE: PRT
<213> ORGANISM: Artificial Sequence
<220> FEATURE:
<223> OTHER INFORMATION: Synthetic protein

<400> SEQUENCE: 38

```
Met Lys Pro Ala Lys Leu Leu Val Phe Val Leu Val Val Ser Ile Leu
1               5                   10                  15

Ala Gly Leu Tyr Ala Gln Pro Ala Gly Ala Ala Lys Tyr Leu Glu Leu
                20                  25                  30

Glu Glu Gly Gly Val Ile Met Gln Ala Phe Tyr Trp Asp Val Pro Ser
            35                  40                  45

Gly Gly Ile Trp Trp Asp Thr Ile Arg Gln Lys Ile Pro Glu Trp Tyr
        50                  55                  60

Asp Ala Gly Ile Ser Ala Ile Trp Ile Pro Pro Ala Ser Lys Gly Met
65                  70                  75                  80

Gly Gly Ala Tyr Ser Met Gly Tyr Asp Pro Tyr Asp Phe Phe Asp Leu
                85                  90                  95

Gly Glu Tyr Asp Gln Lys Gly Thr Val Glu Thr Arg Phe Gly Ser Lys
                100                 105                 110

Gln Glu Leu Val Asn Met Ile Asn Thr Ala His Ala Tyr Gly Ile Lys
            115                 120                 125

Val Ile Ala Asp Ile Val Ile Asn His Arg Ala Gly Gly Asp Leu Glu
        130                 135                 140
```

Trp Asn Pro Phe Val Asn Asp Tyr Thr Trp Thr Asp Phe Ser Lys Val
145                 150                 155                 160

Ala Ser Gly Lys Tyr Thr Ala Asn Tyr Leu Asp Phe His Pro Asn Glu
            165                 170                 175

Val Lys Cys Cys Asp Glu Gly Thr Phe Gly Gly Phe Pro Asp Ile Ala
        180                 185                 190

His Glu Lys Ser Trp Asp Gln Tyr Trp Leu Trp Ala Ser Asn Glu Ser
    195                 200                 205

Tyr Ala Ala Tyr Leu Arg Ser Ile Gly Val Asp Ala Trp Arg Phe Asp
210                 215                 220

Tyr Val Lys Gly Tyr Gly Ala Trp Val Val Lys Asp Trp Leu Asp Trp
225                 230                 235                 240

Trp Gly Gly Trp Ala Val Gly Glu Tyr Trp Asp Thr Asn Val Asp Ala
                245                 250                 255

Leu Leu Asn Trp Ala Tyr Ser Ser Asp Ala Lys Val Phe Asp Phe Pro
            260                 265                 270

Leu Tyr Tyr Lys Met Asp Ala Ala Phe Asp Asn Lys Asn Ile Pro Ala
        275                 280                 285

Leu Val Glu Ala Leu Lys Asn Gly Gly Thr Val Val Ser Arg Asp Pro
    290                 295                 300

Phe Lys Ala Val Thr Phe Val Ala Asn His Asp Thr Asp Ile Ile Trp
305                 310                 315                 320

Asn Lys Tyr Pro Ala Tyr Ala Phe Ile Leu Thr Tyr Glu Gly Gln Pro
                325                 330                 335

Thr Ile Phe Tyr Arg Asp Tyr Glu Glu Trp Leu Asn Lys Asp Arg Leu
            340                 345                 350

Lys Asn Leu Ile Trp Ile His Asp His Leu Ala Gly Gly Ser Thr Asp
        355                 360                 365

Ile Val Tyr Tyr Asp Asn Asp Glu Leu Ile Phe Val Arg Asn Gly Tyr
    370                 375                 380

Gly Asp Lys Pro Gly Leu Ile Thr Tyr Ile Asn Leu Gly Ser Ser Lys
385                 390                 395                 400

Ala Gly Arg Trp Val Tyr Val Pro Lys Phe Ala Gly Ala Cys Ile His
                405                 410                 415

Glu Tyr Thr Gly Asn Leu Gly Gly Trp Val Asp Lys Trp Val Asp Ser
            420                 425                 430

Ser Gly Trp Val Tyr Leu Glu Ala Pro Ala His Asp Pro Ala Asn Gly
        435                 440                 445

Tyr Tyr Gly Tyr Ser Val Trp Ser Tyr Cys Gly Val Gly
    450                 455                 460

<210> SEQ ID NO 39
<211> LENGTH: 461
<212> TYPE: PRT
<213> ORGANISM: Artificial Sequence
<220> FEATURE:
<223> OTHER INFORMATION: Synthetic protein

<400> SEQUENCE: 39

Met Lys Lys Phe Val Ala Leu Phe Ile Thr Met Phe Phe Val Val Ser
1               5                   10                  15

Met Ala Val Val Ala Gln Pro Ala Ser Ala Ala Lys Tyr Ser Glu Leu
            20                  25                  30

Glu Glu Gly Gly Val Ile Met Gln Ala Phe Tyr Trp Asp Val Pro Gly
        35                  40                  45

```
Gly Gly Ile Trp Trp Asp Thr Ile Arg Ser Lys Ile Pro Glu Trp Tyr
 50                  55                  60
Glu Ala Gly Ile Ser Ala Ile Trp Ile Pro Pro Ala Ser Lys Gly Met
 65                  70                  75                  80
Ser Gly Gly Tyr Ser Met Gly Tyr Asp Pro Tyr Asp Phe Phe Asp Leu
                 85                  90                  95
Gly Glu Tyr Asn Gln Lys Gly Thr Ile Glu Thr Arg Phe Gly Ser Lys
             100                 105                 110
Gln Glu Leu Ile Asn Met Ile Asn Thr Ala His Ala Tyr Gly Ile Lys
         115                 120                 125
Val Ile Ala Asp Ile Val Ile Asn His Arg Ala Gly Gly Asp Leu Glu
     130                 135                 140
Trp Asn Pro Phe Val Gly Asp Tyr Thr Trp Thr Asp Phe Ser Lys Val
145                 150                 155                 160
Ala Ser Gly Lys Tyr Thr Ala Asn Tyr Leu Asp Phe His Pro Asn Glu
                 165                 170                 175
Val Lys Cys Cys Asp Glu Gly Thr Phe Gly Gly Phe Pro Asp Ile Ala
             180                 185                 190
His Glu Lys Ser Trp Asp Gln His Trp Leu Trp Ala Ser Asp Glu Ser
         195                 200                 205
Tyr Ala Ala Tyr Leu Arg Ser Ile Gly Val Asp Ala Trp Arg Phe Asp
     210                 215                 220
Tyr Val Lys Gly Tyr Gly Ala Trp Val Val Lys Asp Trp Leu Asn Trp
225                 230                 235                 240
Trp Gly Gly Trp Ala Val Gly Glu Tyr Trp Asp Thr Asn Val Asp Ala
                 245                 250                 255
Leu Leu Asn Trp Ala Tyr Ser Ser Gly Ala Lys Val Phe Asp Phe Pro
             260                 265                 270
Leu Tyr Tyr Lys Met Asp Glu Ala Phe Asp Asn Lys Asn Ile Pro Ala
     275                 280                 285
Leu Val Ser Ala Leu Gln Asn Gly Gln Thr Val Val Ser Arg Asp Pro
290                 295                 300
Phe Lys Ala Val Thr Phe Val Ala Asn His Asp Thr Asp Ile Ile Trp
305                 310                 315                 320
Asn Lys Tyr Leu Ala Tyr Ala Phe Ile Leu Thr Tyr Glu Gly Gln Pro
                 325                 330                 335
Val Ile Phe Tyr Arg Asp Tyr Glu Glu Trp Leu Asn Lys Asp Arg Leu
             340                 345                 350
Asn Asn Leu Ile Trp Ile His Asp His Leu Ala Gly Gly Ser Thr Ser
         355                 360                 365
Ile Val Tyr Tyr Asp Ser Asp Glu Met Ile Phe Val Arg Asn Gly Tyr
     370                 375                 380
Gly Ser Lys Pro Gly Leu Ile Thr Tyr Ile Asn Leu Gly Ser Ser Lys
385                 390                 395                 400
Val Gly Arg Trp Val Tyr Val Pro Lys Phe Ala Gly Ala Cys Ile His
                 405                 410                 415
Glu Tyr Thr Gly Asn Leu Gly Gly Trp Val Asp Lys Tyr Val Tyr Ser
             420                 425                 430
Ser Gly Trp Val Tyr Leu Glu Ala Pro Ala Tyr Asp Pro Ala Asn Gly
         435                 440                 445
Gln Tyr Gly Tyr Ser Val Trp Ser Tyr Cys Gly Val Gly
     450                 455                 460
```

```
<210> SEQ ID NO 40
<211> LENGTH: 432
<212> TYPE: PRT
<213> ORGANISM: Artificial Sequence
<220> FEATURE:
<223> OTHER INFORMATION: Synthetic protein

<400> SEQUENCE: 40
```

| | | | | | | | | | | | | | | | |
|---|---|---|---|---|---|---|---|---|---|---|---|---|---|---|---|
| Met | Ala | Leu | Glu | Asp | Gly | Gly | Leu | Ile | Met | Gln | Ala | Phe | Tyr | Trp | Asp |
| 1 | | | | 5 | | | | | 10 | | | | | 15 | |
| Val | Pro | Gly | Gly | Gly | Ile | Trp | Trp | Asp | Thr | Ile | Ala | Gln | Lys | Ile | Pro |
| | | | 20 | | | | | 25 | | | | | 30 | | |
| Glu | Trp | Ala | Ser | Ala | Gly | Ile | Ser | Ala | Ile | Trp | Ile | Pro | Pro | Ala | Ser |
| | | | | 35 | | | | | 40 | | | | | 45 | |
| Lys | Gly | Met | Ser | Gly | Gly | Tyr | Ser | Met | Gly | Tyr | Asp | Pro | Tyr | Asp | Phe |
| | | | 50 | | | | | 55 | | | | | 60 | | |
| Phe | Asp | Leu | Gly | Glu | Tyr | Tyr | Gln | Lys | Gly | Thr | Val | Glu | Thr | Arg | Phe |
| 65 | | | | | 70 | | | | | 75 | | | | | 80 |
| Gly | Ser | Lys | Glu | Glu | Leu | Val | Asn | Met | Ile | Asn | Thr | Ala | His | Ser | Tyr |
| | | | | 85 | | | | | 90 | | | | | 95 | |
| Gly | Ile | Lys | Val | Ile | Ala | Asp | Ile | Val | Ile | Asn | His | Arg | Ala | Gly | Gly |
| | | | 100 | | | | | 105 | | | | | 110 | | |
| Asp | Leu | Glu | Trp | Asn | Pro | Phe | Val | Asn | Asp | Tyr | Thr | Trp | Thr | Asp | Phe |
| | | | | 115 | | | | | 120 | | | | | 125 | |
| Ser | Lys | Val | Ala | Ser | Gly | Lys | Tyr | Thr | Ala | Asn | Tyr | Leu | Asp | Phe | His |
| | 130 | | | | | 135 | | | | | 140 | | | | |
| Pro | Asn | Glu | Leu | His | Cys | Cys | Asp | Glu | Gly | Thr | Phe | Gly | Gly | Tyr | Pro |
| 145 | | | | | 150 | | | | | 155 | | | | | 160 |
| Asp | Ile | Cys | His | Asp | Lys | Ser | Trp | Asp | Gln | Tyr | Trp | Leu | Trp | Ala | Ser |
| | | | | 165 | | | | | 170 | | | | | 175 | |
| Ser | Glu | Ser | Tyr | Ala | Ala | Tyr | Leu | Arg | Ser | Ile | Gly | Val | Asp | Ala | Trp |
| | | | 180 | | | | | 185 | | | | | 190 | | |
| Arg | Phe | Asp | Tyr | Val | Lys | Gly | Tyr | Gly | Ala | Trp | Val | Val | Asn | Asp | Trp |
| | | | | 195 | | | | | 200 | | | | | 205 | |
| Leu | Ser | Trp | Trp | Gly | Gly | Trp | Ala | Val | Gly | Glu | Tyr | Trp | Asp | Thr | Asn |
| | 210 | | | | | 215 | | | | | 220 | | | | |
| Val | Asp | Ala | Leu | Leu | Asn | Trp | Ala | Tyr | Ser | Ser | Gly | Ala | Lys | Val | Phe |
| 225 | | | | | 230 | | | | | 235 | | | | | 240 |
| Asp | Phe | Pro | Leu | Tyr | Tyr | Lys | Met | Asp | Glu | Ala | Phe | Asp | Asn | Thr | Asn |
| | | | | 245 | | | | | 250 | | | | | 255 | |
| Ile | Pro | Ala | Leu | Val | Asp | Ala | Leu | Arg | Tyr | Gly | Gln | Thr | Val | Val | Ser |
| | | | 260 | | | | | 265 | | | | | 270 | | |
| Arg | Asp | Pro | Phe | Lys | Ala | Val | Thr | Phe | Val | Ala | Asn | His | Asp | Thr | Asp |
| | | | | 275 | | | | | 280 | | | | | 285 | |
| Ile | Ile | Trp | Asn | Lys | Tyr | Pro | Ala | Tyr | Ala | Phe | Ile | Leu | Thr | Tyr | Glu |
| | 290 | | | | | 295 | | | | | 300 | | | | |
| Gly | Gln | Pro | Val | Ile | Phe | Tyr | Arg | Asp | Tyr | Glu | Glu | Trp | Leu | Asn | Lys |
| 305 | | | | | 310 | | | | | 315 | | | | | 320 |
| Asp | Lys | Leu | Asn | Asn | Leu | Ile | Trp | Ile | His | Asp | His | Leu | Ala | Gly | Gly |
| | | | | 325 | | | | | 330 | | | | | 335 | |
| Ser | Thr | Asp | Ile | Val | Tyr | Tyr | Asp | Ser | Asp | Glu | Leu | Ile | Phe | Val | Arg |
| | | | 340 | | | | | 345 | | | | | 350 | | |
| Asn | Gly | Tyr | Gly | Thr | Lys | Pro | Gly | Leu | Ile | Thr | Tyr | Ile | Asn | Leu | Gly |
| | | | | 355 | | | | | 360 | | | | | 365 | |

```
Ser Ser Lys Val Gly Arg Trp Val Tyr Val Pro Lys Phe Ala Gly Ser
    370                 375                 380

Cys Ile His Glu Tyr Thr Gly Asn Leu Gly Gly Trp Ile Asp Lys Tyr
385                 390                 395                 400

Val Ser Ser Gly Trp Val Tyr Leu Glu Ala Pro Ala His Asp Pro
            405                 410                 415

Ala Asn Gly Tyr Tyr Gly Tyr Ser Val Trp Ser Tyr Cys Gly Val Gly
            420                 425                 430
```

<210> SEQ ID NO 41
<211> LENGTH: 432
<212> TYPE: PRT
<213> ORGANISM: Artificial Sequence
<220> FEATURE:
<223> OTHER INFORMATION: Synthetic protein

<400> SEQUENCE: 41

```
Met Ala Leu Glu Glu Gly Gly Leu Ile Met Gln Ala Phe Tyr Trp Asp
1               5                   10                  15

Val Pro Gly Gly Gly Ile Trp Trp Asp Thr Ile Ala Gln Lys Ile Pro
            20                  25                  30

Glu Trp Ala Ser Ala Gly Ile Ser Ala Ile Trp Ile Pro Pro Ala Ser
        35                  40                  45

Lys Gly Met Ser Gly Gly Tyr Ser Met Gly Tyr Asp Pro Tyr Asp Phe
50                  55                  60

Phe Asp Leu Gly Glu Tyr Tyr Gln Lys Gly Thr Val Glu Thr Arg Phe
65                  70                  75                  80

Gly Ser Lys Glu Glu Leu Val Asn Met Ile Asn Thr Ala His Ser Tyr
                85                  90                  95

Gly Ile Lys Val Ile Ala Asp Ile Val Ile Asn His Arg Ala Gly Gly
            100                 105                 110

Gly Leu Glu Trp Asn Pro Phe Val Asn Asp Tyr Thr Trp Thr Asp Phe
        115                 120                 125

Ser Lys Val Ala Ser Gly Lys Tyr Thr Ala Asn Tyr Leu Asp Phe His
130                 135                 140

Pro Asn Glu Leu His Cys Cys Asp Glu Gly Thr Phe Gly Gly Tyr Pro
145                 150                 155                 160

Asp Ile Cys His Asp Lys Ser Trp Asp Gln Tyr Trp Leu Trp Ala Ser
                165                 170                 175

Ser Glu Ser Tyr Ala Ala Tyr Leu Arg Ser Ile Gly Val Asp Ala Trp
            180                 185                 190

Cys Phe Asp Tyr Val Lys Gly Tyr Gly Ala Trp Val Val Asn Asp Trp
        195                 200                 205

Leu Ser Trp Trp Gly Gly Trp Ala Val Gly Glu Tyr Trp Asp Thr Asn
210                 215                 220

Val Asp Ala Leu Leu Asn Trp Ala Tyr Asn Ser Gly Ala Lys Val Phe
225                 230                 235                 240

Asp Phe Pro Leu Tyr Tyr Lys Met Asp Glu Ala Phe Asp Asn Thr Asn
                245                 250                 255

Ile Pro Ala Leu Val Tyr Ala Leu Lys Asn Gly Gly Thr Val Val Ser
            260                 265                 270

Arg Asp Pro Phe Lys Ala Val Thr Phe Val Ala Asn His Asp Thr Asp
        275                 280                 285

Ile Ile Trp Asn Lys Tyr Pro Ala Tyr Ala Phe Ile Leu Thr Tyr Glu
290                 295                 300
```

Gly Gln Pro Val Ile Phe Tyr Arg Asp Tyr Glu Trp Leu Asn Lys
305                 310                 315                 320

Asp Lys Leu Asn Asn Leu Ile Trp Ile His Asp His Leu Ala Gly Gly
            325                 330                 335

Ser Thr Asp Ile Val Tyr Tyr Asp Ser Asp Glu Leu Ile Phe Val Arg
            340                 345                 350

Asn Gly Tyr Gly Thr Lys Pro Gly Leu Ile Thr Tyr Ile Asn Leu Gly
            355                 360                 365

Ser Ser Lys Ala Gly Arg Trp Val Tyr Val Pro Lys Phe Ala Gly Ser
370                 375                 380

Cys Ile His Glu Tyr Thr Gly Ser Leu Gly Gly Trp Ile Asp Lys Tyr
385                 390                 395                 400

Val Ser Ser Ser Gly Trp Val Tyr Leu Glu Ala Pro Ala His Asp Pro
                405                 410                 415

Ala Asn Gly Gln Tyr Gly Tyr Ser Val Trp Ser Tyr Cys Gly Val Gly
            420                 425                 430

<210> SEQ ID NO 42
<211> LENGTH: 457
<212> TYPE: PRT
<213> ORGANISM: Artificial Sequence
<220> FEATURE:
<223> OTHER INFORMATION: Synthetic protein

<400> SEQUENCE: 42

Met Ala Arg Lys Thr Leu Ala Ile Phe Phe Val Leu Val Leu Leu
1               5                   10                  15

Ser Leu Ser Ala Val Pro Ala Lys Ala Glu Thr Leu Glu Asn Gly Gly
            20                  25                  30

Val Ile Met Gln Ala Phe Tyr Trp Asp Val Pro Gly Gly Gly Ile Trp
        35                  40                  45

Trp Asp Thr Ile Ala Gln Lys Ile Pro Glu Trp Ala Ser Ala Gly Ile
    50                  55                  60

Ser Ala Ile Trp Ile Pro Pro Ala Ser Lys Gly Met Ser Gly Gly Tyr
65                  70                  75                  80

Ser Met Gly Tyr Asp Pro Tyr Asp Phe Phe Asp Leu Gly Glu Tyr Tyr
                85                  90                  95

Gln Lys Gly Thr Val Glu Thr Arg Phe Gly Ser Lys Glu Glu Leu Val
            100                 105                 110

Asn Met Ile Asn Thr Ala His Ser Tyr Gly Ile Lys Val Ile Ala Asp
        115                 120                 125

Ile Val Ile Asn His Arg Ala Gly Gly Asp Leu Glu Trp Asn Pro Phe
    130                 135                 140

Val Asn Asp Tyr Thr Trp Thr Asp Phe Ser Lys Val Ala Ser Gly Lys
145                 150                 155                 160

Tyr Thr Ala Asn Tyr Leu Asp Phe His Pro Asn Glu Leu His Cys Cys
                165                 170                 175

Asp Glu Gly Thr Phe Gly Gly Tyr Pro Asp Ile Cys His Asp Lys Ser
            180                 185                 190

Trp Asp Gln Tyr Trp Leu Trp Ala Ser Ser Glu Ser Tyr Ala Ala Tyr
        195                 200                 205

Leu Arg Ser Ile Gly Val Asp Ala Trp Arg Phe Asp Tyr Val Lys Gly
    210                 215                 220

Tyr Gly Ala Trp Val Val Asn Asp Trp Leu Ser Trp Trp Gly Gly Trp
225                 230                 235                 240

```
Ala Val Gly Glu Tyr Trp Asp Thr Asn Val Asp Ala Leu Leu Asn Trp
            245                 250                 255

Ala Tyr Ser Ser Gly Ala Lys Val Phe Asp Phe Pro Leu Tyr Tyr Lys
            260                 265                 270

Met Asp Glu Ala Phe Asp Asn Thr Asn Ile Pro Ala Leu Val Asp Ala
            275                 280                 285

Leu Arg Tyr Gly Gln Thr Val Val Ser Arg Asp Pro Phe Lys Ala Val
            290                 295                 300

Thr Phe Val Ala Asn His Asp Thr Asp Ile Ile Trp Asn Lys Tyr Pro
305                 310                 315                 320

Ala Tyr Ala Phe Ile Leu Thr Tyr Glu Gly Gln Pro Val Ile Phe Tyr
            325                 330                 335

Arg Asp Tyr Glu Glu Trp Leu Asn Lys Asp Lys Leu Asn Asn Leu Ile
            340                 345                 350

Trp Ile His Asp His Leu Ala Gly Gly Ser Thr Asp Ile Val Tyr Tyr
            355                 360                 365

Asp Ser Asp Glu Leu Ile Phe Val Arg Asn Gly Tyr Gly Thr Lys Pro
            370                 375                 380

Gly Leu Ile Thr Tyr Ile Asn Leu Gly Ser Ser Lys Val Gly Arg Trp
385                 390                 395                 400

Val Tyr Val Pro Lys Phe Ala Gly Ser Cys Ile His Glu Tyr Thr Gly
            405                 410                 415

Asn Leu Gly Gly Trp Ile Asp Lys Tyr Val Ser Ser Gly Trp Val
            420                 425                 430

Tyr Leu Glu Ala Pro Ala His Asp Pro Ala Asn Gly Tyr Tyr Gly Tyr
            435                 440                 445

Ser Val Trp Ser Tyr Cys Gly Val Gly
    450                 455

<210> SEQ ID NO 43
<211> LENGTH: 471
<212> TYPE: PRT
<213> ORGANISM: Artificial Sequence
<220> FEATURE:
<223> OTHER INFORMATION: Synthetic protein

<400> SEQUENCE: 43

Met Pro Ala Phe Lys Ser Lys Val Met His Met Lys Leu Lys Tyr Leu
1               5                   10                  15

Ala Leu Val Leu Leu Ala Val Ala Ser Ile Gly Leu Leu Ser Thr Pro
            20                  25                  30

Val Gly Ala Ala Lys Tyr Ser Glu Leu Glu Glu Gly Val Ile Met
            35                  40                  45

Gln Ala Phe Tyr Trp Asp Val Pro Thr Gly Gly Ile Trp Trp Asp Thr
50                  55                  60

Ile Arg Gln Lys Ile Pro Glu Trp Tyr Asp Ala Gly Ile Ser Ala Ile
65                  70                  75                  80

Trp Ile Pro Pro Ala Ser Lys Gly Met Gly Ala Tyr Ser Met Gly
            85                  90                  95

Tyr Asp Pro Tyr Asp Phe Phe Asp Leu Gly Glu Tyr Tyr Gln Lys Gly
            100                 105                 110

Thr Val Glu Thr Arg Phe Gly Ser Lys Glu Glu Leu Val Asn Met Ile
            115                 120                 125

Asn Thr Ala His Ser Tyr Gly Ile Lys Val Ile Ala Asp Ile Val Ile
            130                 135                 140
```

Asn His Arg Ala Gly Gly Asp Leu Glu Trp Asn Pro Phe Val Asn Asn
145                 150                 155                 160

Tyr Thr Trp Thr Asp Phe Ser Lys Val Ala Ser Gly Lys Tyr Thr Ala
            165                 170                 175

Asn Tyr Leu Asp Phe His Pro Asn Glu Val Lys Cys Cys Asp Glu Gly
        180                 185                 190

Thr Phe Gly Asp Phe Pro Asp Ile Ala His Glu Lys Ser Trp Asp Gln
    195                 200                 205

Tyr Trp Leu Trp Ala Ser Asn Glu Ser Tyr Ala Ala Tyr Leu Arg Ser
210                 215                 220

Ile Gly Ile Asp Ala Trp Arg Phe Asp Tyr Val Lys Gly Tyr Gly Ala
225                 230                 235                 240

Trp Val Val Asn Asp Trp Leu Ser Trp Trp Gly Gly Trp Ala Val Gly
            245                 250                 255

Glu Tyr Trp Asp Thr Asn Val Asp Ala Leu Leu Asn Trp Ala Tyr Asn
        260                 265                 270

Ser Gly Ala Lys Val Phe Asp Phe Pro Leu Tyr Tyr Lys Met Asp Glu
    275                 280                 285

Ala Phe Asp Asn Thr Asn Ile Pro Ala Leu Val Tyr Ala Leu Gln Asn
290                 295                 300

Gly Gly Thr Val Val Ser Arg Asp Pro Phe Lys Ala Val Thr Phe Val
305                 310                 315                 320

Ala Asn His Asp Thr Asp Ile Ile Trp Asn Lys Tyr Pro Ala Tyr Ala
            325                 330                 335

Phe Ile Leu Thr Tyr Glu Gly Gln Pro Val Ile Phe Tyr Arg Asp Tyr
        340                 345                 350

Glu Glu Trp Leu Asn Lys Asp Lys Leu Asn Asn Leu Ile Trp Ile His
    355                 360                 365

Glu His Leu Ala Gly Gly Ser Thr Lys Ile Leu Tyr Tyr Asp Asn Asp
370                 375                 380

Glu Leu Ile Phe Met Arg Glu Gly Tyr Gly Ser Lys Pro Gly Leu Ile
385                 390                 395                 400

Thr Tyr Ile Asn Leu Gly Asn Asp Trp Ala Glu Arg Trp Val Asn Val
            405                 410                 415

Gly Ser Lys Phe Ala Gly Tyr Thr Ile His Glu Tyr Thr Gly Asn Leu
        420                 425                 430

Gly Gly Trp Val Asp Arg Trp Val Gln Tyr Asp Gly Trp Val Lys Leu
    435                 440                 445

Thr Ala Pro Pro His Asp Pro Ala Asn Gly Tyr Tyr Gly Tyr Ser Val
450                 455                 460

Trp Ser Tyr Ala Gly Val Gly
465                 470

<210> SEQ ID NO 44
<211> LENGTH: 445
<212> TYPE: PRT
<213> ORGANISM: Artificial Sequence
<220> FEATURE:
<223> OTHER INFORMATION: Synthetic protein

<400> SEQUENCE: 44

Met Ala Lys Tyr Ser Glu Leu Glu Gln Gly Gly Val Ile Met Gln Ala
1               5                   10                  15

Phe Tyr Trp Asp Val Pro Glu Gly Gly Ile Trp Trp Asp Thr Ile Arg
            20                  25                  30

Gln Lys Ile Pro Glu Trp Tyr Asp Ala Gly Ile Ser Ala Ile Trp Ile
                35                  40                  45

Pro Pro Ala Ser Lys Gly Met Gly Gly Ala Tyr Ser Met Gly Tyr Asp
 50                  55                  60

Pro Tyr Asp Tyr Phe Asp Leu Gly Glu Phe Tyr Gln Lys Gly Thr Val
 65                  70                  75                  80

Glu Thr Arg Phe Gly Ser Lys Glu Glu Leu Val Asn Met Ile Ser Thr
                85                  90                  95

Ala His Gln Tyr Gly Ile Lys Val Ile Ala Asp Ile Val Ile Asn His
                100                 105                 110

Arg Ala Gly Gly Asp Leu Glu Trp Asn Pro Tyr Val Gly Asp Tyr Thr
                115                 120                 125

Trp Thr Asp Phe Ser Lys Val Ala Ser Gly Lys Tyr Lys Ala His Tyr
                130                 135                 140

Met Asp Phe His Pro Asn Asn Tyr Ser Thr Ser Asp Glu Gly Thr Phe
145                 150                 155                 160

Gly Gly Phe Pro Asp Ile Asp His Leu Val Pro Phe Asn Gln Tyr Trp
                165                 170                 175

Leu Trp Ala Ser Asn Glu Ser Tyr Ala Ala Tyr Leu Arg Ser Ile Gly
                180                 185                 190

Ile Asp Ala Trp Arg Phe Asp Tyr Val Lys Gly Tyr Gly Ala Trp Val
                195                 200                 205

Val Lys Asp Trp Leu Ser Gln Trp Gly Trp Ala Val Gly Glu Tyr
                210                 215                 220

Trp Asp Thr Asn Val Asp Ala Leu Leu Asn Trp Ala Tyr Ser Ser Gly
225                 230                 235                 240

Ala Lys Val Phe Asp Phe Pro Leu Tyr Tyr Lys Met Asp Glu Ala Phe
                245                 250                 255

Asp Asn Lys Asn Ile Pro Ala Leu Val Tyr Ala Ile Gln Asn Gly Glu
                260                 265                 270

Thr Val Val Ser Arg Asp Pro Phe Lys Ala Val Thr Phe Val Ala Asn
                275                 280                 285

His Asp Thr Asn Ile Ile Trp Asn Lys Tyr Pro Ala Tyr Ala Phe Ile
290                 295                 300

Leu Thr Tyr Glu Gly Gln Pro Val Ile Phe Tyr Arg Asp Tyr Glu Glu
305                 310                 315                 320

Trp Leu Asn Lys Asp Lys Leu Asn Asn Leu Ile Trp Ile His Glu His
                325                 330                 335

Leu Ala Gly Gly Ser Thr Lys Ile Leu Tyr Tyr Asp Asp Glu Leu
                340                 345                 350

Ile Phe Met Arg Glu Gly Tyr Gly Asp Arg Pro Gly Leu Ile Thr Tyr
                355                 360                 365

Ile Asn Leu Gly Ser Asp Trp Ala Glu Arg Trp Val Asn Val Gly Ser
370                 375                 380

Lys Phe Ala Gly Tyr Thr Ile His Glu Tyr Thr Gly Asn Leu Gly Gly
385                 390                 395                 400

Trp Val Asp Arg Tyr Val Gln Tyr Asp Gly Trp Val Lys Leu Thr Ala
                405                 410                 415

Pro Pro His Asp Pro Ala Asn Gly Tyr Tyr Gly Tyr Ser Val Trp Ser
                420                 425                 430

Tyr Ala Gly Val Gly Arg Ser His His His His His
                435                 440                 445

```
<210> SEQ ID NO 45
<211> LENGTH: 464
<212> TYPE: PRT
<213> ORGANISM: Artificial Sequence
<220> FEATURE:
<223> OTHER INFORMATION: Synthetic protein

<400> SEQUENCE: 45

Val Val His Met Lys Leu Lys Tyr Leu Ala Leu Val Leu Leu Ala Val
1               5                   10                  15

Ala Ser Ile Gly Leu Leu Ser Thr Pro Val Gly Ala Ala Lys Tyr Ser
            20                  25                  30

Glu Leu Glu Glu Gly Gly Val Ile Met Gln Ala Phe Tyr Trp Asp Val
        35                  40                  45

Pro Gly Gly Gly Ile Trp Trp Asp Thr Ile Arg Gln Lys Ile Pro Glu
    50                  55                  60

Trp Tyr Asp Ala Gly Ile Ser Ala Ile Trp Ile Pro Pro Ala Ser Lys
65                  70                  75                  80

Gly Met Gly Gly Gly Tyr Ser Met Gly Tyr Asp Pro Tyr Asp Phe Phe
                85                  90                  95

Asp Leu Gly Glu Tyr Tyr Gln Lys Gly Thr Val Glu Thr Arg Phe Gly
            100                 105                 110

Ser Lys Glu Glu Leu Val Asn Met Ile Asn Thr Ala His Ser Tyr Gly
        115                 120                 125

Ile Lys Val Ile Ala Asp Ile Val Asn His Arg Ala Gly Gly Asp
        130                 135                 140

Leu Glu Trp Asn Pro Phe Val Asn Asn Tyr Thr Trp Thr Asp Phe Ser
145                 150                 155                 160

Lys Val Ala Ser Gly Lys Tyr Thr Ala Asn Tyr Leu Asp Phe His Pro
                165                 170                 175

Asn Glu Val Lys Cys Cys Asp Glu Gly Thr Phe Gly Asp Phe Pro Asp
            180                 185                 190

Ile Ala His Glu Lys Ser Trp Asp Gln Tyr Trp Leu Trp Ala Ser Asn
        195                 200                 205

Glu Ser Tyr Ala Ala Tyr Leu Arg Ser Ile Gly Ile Asp Ala Trp Arg
    210                 215                 220

Phe Asp Tyr Val Lys Gly Tyr Gly Ala Trp Val Val Asn Asp Trp Leu
225                 230                 235                 240

Ser Trp Trp Gly Gly Trp Ala Val Gly Glu Tyr Trp Asp Thr Asn Val
                245                 250                 255

Asp Ala Leu Leu Asn Trp Ala Tyr Asp Ser Gly Ala Lys Val Phe Asp
            260                 265                 270

Phe Pro Leu Tyr Tyr Lys Met Asp Glu Ala Phe Asp Asn Thr Asn Ile
        275                 280                 285

Pro Ala Leu Val Tyr Ala Leu Gln Asn Gly Gly Thr Val Val Ser Arg
    290                 295                 300

Asp Pro Phe Lys Ala Val Thr Phe Val Ala Asn His Asp Thr Asp Ile
305                 310                 315                 320

Ile Trp Asn Lys Tyr Pro Ala Tyr Ala Phe Ile Leu Thr Tyr Glu Gly
                325                 330                 335

Gln Pro Val Ile Phe Tyr Arg Asp Tyr Glu Glu Trp Leu Asn Lys Asp
            340                 345                 350

Lys Leu Asn Asn Leu Ile Trp Ile His Glu His Leu Ala Gly Gly Ser
        355                 360                 365

Thr Lys Ile Leu Tyr Tyr Asp Asn Asp Glu Leu Ile Phe Met Arg Glu
```

```
                    370                 375                 380
Gly Tyr Gly Ser Lys Pro Gly Leu Ile Thr Tyr Ile Asn Leu Gly Asn
385                 390                 395                 400

Asp Trp Ala Glu Arg Trp Val Asn Val Gly Ser Lys Phe Ala Gly Tyr
                405                 410                 415

Thr Ile His Glu Tyr Thr Gly Asn Leu Gly Gly Trp Val Asp Arg Trp
                420                 425                 430

Val Gln Tyr Asp Gly Trp Val Lys Leu Thr Ala Pro Pro His Asp Pro
                435                 440                 445

Ala Asn Gly Tyr Tyr Gly Tyr Ser Val Trp Ser Tyr Ala Gly Val Gly
                450                 455                 460

<210> SEQ ID NO 46
<211> LENGTH: 461
<212> TYPE: PRT
<213> ORGANISM: Artificial Sequence
<220> FEATURE:
<223> OTHER INFORMATION: Synthetic protein

<400> SEQUENCE: 46

Met Lys Lys Phe Val Ala Leu Leu Ile Thr Met Phe Phe Val Val Ser
1               5                   10                  15

Met Ala Ala Val Ala Gln Pro Ala Ser Ala Ala Lys Tyr Ser Glu Leu
                20                  25                  30

Glu Glu Gly Gly Val Ile Met Gln Ala Phe Tyr Trp Asp Val Pro Ala
            35                  40                  45

Gly Gly Ile Trp Trp Asp Thr Ile Arg Ser Lys Ile Pro Glu Trp Tyr
        50                  55                  60

Glu Ala Gly Ile Ser Ala Ile Trp Ile Pro Pro Ala Ser Lys Gly Met
65                  70                  75                  80

Gly Gly Ala Tyr Ser Met Gly Tyr Asp Pro Tyr Asp Phe Phe Asp Leu
                85                  90                  95

Gly Glu Tyr Asn Gln Lys Gly Thr Val Glu Thr Arg Phe Gly Ser Lys
            100                 105                 110

Gln Glu Leu Ile Asn Met Ile Asn Thr Ala His Ala Tyr Gly Ile Lys
        115                 120                 125

Val Ile Ala Asp Ile Val Ile Asn His Arg Ala Gly Gly Asp Leu Glu
130                 135                 140

Trp Asn Pro Phe Val Gly Asp Tyr Thr Trp Thr Asp Phe Ser Lys Val
145                 150                 155                 160

Ala Ser Gly Lys Tyr Thr Ala Asn Tyr Leu Asp Phe His Pro Asn Glu
                165                 170                 175

Val Lys Cys Cys Asp Glu Gly Thr Phe Gly Gly Phe Pro Asp Ile Ala
            180                 185                 190

His Glu Lys Glu Trp Asp Gln His Trp Leu Trp Ala Ser Asp Glu Ser
        195                 200                 205

Tyr Ala Ala Tyr Leu Arg Ser Ile Gly Val Asp Ala Trp Arg Phe Asp
210                 215                 220

Tyr Val Lys Gly Tyr Gly Ala Trp Val Val Lys Asp Trp Leu Asn Trp
225                 230                 235                 240

Trp Gly Gly Trp Ala Val Gly Glu Tyr Trp Asp Thr Asn Val Asp Ala
                245                 250                 255

Leu Leu Asn Trp Ala Tyr Ser Ser Gly Ala Lys Val Phe Asp Phe Pro
            260                 265                 270

Leu Tyr Tyr Lys Met Asp Glu Ala Phe Asp Asn Thr Asn Ile Pro Ala
```

```
            275                 280                 285
Leu Val Asp Ala Leu Gln Asn Gly Gly Thr Val Val Ser Arg Asp Pro
    290                 295                 300

Phe Lys Ala Val Thr Phe Val Ala Asn His Asp Thr Asp Ile Ile Trp
305                 310                 315                 320

Asn Lys Tyr Pro Ala Tyr Ala Phe Ile Leu Thr Tyr Glu Gly Gln Pro
                325                 330                 335

Val Ile Phe Tyr Arg Asp Tyr Glu Glu Trp Leu Asn Lys Asp Lys Leu
                340                 345                 350

Asn Asn Leu Ile Trp Ile His Asp His Leu Ala Gly Gly Ser Thr Ser
                355                 360                 365

Ile Val Tyr Tyr Asp Ser Asp Glu Leu Ile Phe Val Arg Asn Gly Asp
        370                 375                 380

Ser Lys Arg Pro Gly Leu Ile Thr Tyr Ile Asn Leu Gly Ser Ser Lys
385                 390                 395                 400

Val Gly Arg Trp Val Tyr Val Pro Lys Phe Ala Gly Ala Cys Ile His
                405                 410                 415

Glu Tyr Thr Gly Asn Leu Gly Gly Trp Val Asp Lys Tyr Val Glu Ser
            420                 425                 430

Ser Gly Trp Val Tyr Leu Glu Ala Pro Ala Tyr Asp Pro Ala Ser Gly
            435                 440                 445

Gln Tyr Gly Tyr Thr Val Trp Ser Tyr Cys Gly Val Gly
            450                 455                 460

<210> SEQ ID NO 47
<211> LENGTH: 460
<212> TYPE: PRT
<213> ORGANISM: Artificial Sequence
<220> FEATURE:
<223> OTHER INFORMATION: Synthetic protein

<400> SEQUENCE: 47

Val Asn Ile Lys Lys Leu Thr Pro Leu Leu Thr Leu Leu Leu Phe Phe
1               5                   10                  15

Ile Val Leu Ala Ser Pro Val Ser Ala Ala Lys Tyr Leu Glu Leu Glu
                20                  25                  30

Glu Gly Gly Val Ile Met Gln Ala Phe Tyr Trp Asp Val Pro Gly Gly
            35                  40                  45

Gly Ile Trp Trp Asp His Ile Arg Ser Lys Ile Pro Glu Trp Tyr Glu
        50                  55                  60

Ala Gly Ile Ser Ala Ile Trp Leu Pro Pro Ser Lys Gly Met Ser
65                  70                  75                  80

Gly Gly Tyr Ser Met Gly Tyr Asp Pro Tyr Asp Tyr Phe Asp Leu Gly
                85                  90                  95

Glu Tyr Tyr Gln Lys Gly Thr Val Glu Thr Arg Phe Gly Ser Lys Glu
                100                 105                 110

Glu Leu Val Arg Leu Ile Gln Thr Ala His Ala Tyr Gly Ile Lys Val
            115                 120                 125

Ile Ala Asp Val Val Ile Asn His Arg Ala Gly Gly Asp Leu Glu Trp
        130                 135                 140

Asn Pro Phe Val Gly Asp Tyr Thr Trp Thr Asp Phe Ser Lys Val Ala
145                 150                 155                 160

Ser Gly Lys Tyr Thr Ala Asn Tyr Leu Asp Phe His Pro Asn Glu Leu
                165                 170                 175

His Cys Cys Asp Glu Gly Thr Phe Gly Gly Phe Pro Asp Ile Cys His
```

```
                180             185             190
His Lys Glu Trp Asp Gln Tyr Trp Leu Trp Lys Ser Asn Glu Ser Tyr
            195                 200                 205

Ala Ala Tyr Leu Arg Ser Ile Gly Phe Asp Gly Trp Arg Phe Asp Tyr
            210                 215                 220

Val Lys Gly Tyr Gly Ala Trp Val Val Arg Asp Trp Leu Asn Trp Trp
225                 230                 235                 240

Gly Gly Trp Ala Val Gly Glu Tyr Trp Asp Thr Asn Val Asp Ala Leu
                245                 250                 255

Leu Ser Trp Ala Tyr Glu Ser Gly Ala Lys Val Phe Asp Phe Pro Leu
            260                 265                 270

Tyr Tyr Lys Met Asp Glu Ala Phe Asp Asn Asn Ile Pro Ala Leu
            275                 280                 285

Val Tyr Ala Leu Gln Asn Gly Gln Thr Val Val Ser Arg Asp Pro Phe
            290                 295                 300

Lys Ala Val Thr Phe Val Ala Asn His Asp Thr Asp Ile Ile Trp Asn
305                 310                 315                 320

Lys Tyr Pro Ala Tyr Ala Phe Ile Leu Thr Tyr Glu Gly Gln Pro Val
                325                 330                 335

Ile Phe Tyr Arg Asp Phe Glu Glu Trp Leu Asn Lys Asp Lys Leu Ile
                340                 345                 350

Asn Leu Ile Trp Ile His Asp His Leu Ala Gly Gly Ser Thr Thr Ile
            355                 360                 365

Val Tyr Tyr Asp Asn Asp Glu Leu Ile Phe Val Arg Asn Gly Asp Ser
370                 375                 380

Arg Arg Pro Gly Leu Ile Thr Tyr Ile Asn Leu Ser Pro Asn Trp Val
385                 390                 395                 400

Gly Arg Trp Val Tyr Val Pro Lys Phe Ala Gly Ala Cys Ile His Glu
                405                 410                 415

Tyr Thr Gly Asn Leu Gly Gly Trp Val Asp Lys Arg Val Asp Ser Ser
            420                 425                 430

Gly Trp Val Tyr Leu Glu Ala Pro Pro His Asp Pro Ala Asn Gly Tyr
            435                 440                 445

Tyr Gly Tyr Ser Val Trp Ser Tyr Cys Gly Val Gly
            450                 455                 460

<210> SEQ ID NO 48
<211> LENGTH: 484
<212> TYPE: PRT
<213> ORGANISM: Artificial Sequence
<220> FEATURE:
<223> OTHER INFORMATION: Synthetic protein

<400> SEQUENCE: 48

Ser Glu Ser Gln Cys Thr Ala Thr Cys Thr Trp Arg Val Val Tyr Met
1               5                   10                  15

Ser Ala Lys Lys Leu Leu Ala Leu Leu Phe Val Leu Ala Val Leu Val
                20                  25                  30

Gly Val Ala Val Ile Pro Ala Arg Val Gly Ile Ala Pro Val Ser Ala
            35                  40                  45

Gly Ala Thr Ser Arg Pro Ser Leu Glu Glu Gly Val Ile Met Gln
            50                  55                  60

Ala Phe Tyr Trp Asp Val Pro Ala Gly Gly Ile Trp Trp Asp Thr Ile
65                  70                  75                  80

Arg Ser Lys Ile Pro Asp Trp Ala Ser Ala Gly Ile Ser Ala Ile Trp
```

```
                 85                  90                  95
Ile Pro Pro Ala Ser Lys Gly Met Ser Gly Ala Tyr Ser Met Gly Tyr
            100                 105                 110

Asp Pro Tyr Asp Phe Asp Leu Gly Glu Tyr Tyr Gln Lys Gly Thr
            115                 120                 125

Val Glu Thr Arg Phe Gly Ser Lys Gln Glu Leu Ile Asn Met Ile Asn
130                 135                 140

Thr Ala His Ser Tyr Gly Ile Lys Val Ile Ala Asp Ile Val Ile Asn
145                 150                 155                 160

His Arg Ala Gly Gly Asp Leu Glu Trp Asn Pro Phe Thr Asn Ser Tyr
            165                 170                 175

Thr Trp Thr Asp Phe Ser Lys Val Ala Ser Gly Lys Tyr Thr Ala Asn
            180                 185                 190

Tyr Leu Asp Phe His Pro Asn Glu Val Lys Cys Cys Asp Glu Gly Thr
            195                 200                 205

Phe Gly Gly Phe Pro Asp Ile Ala His Glu Lys Ser Trp Asp Gln Tyr
            210                 215                 220

Trp Leu Trp Ala Ser Gln Lys Ser Tyr Ala Ala Tyr Leu Arg Ser Ile
225                 230                 235                 240

Gly Ile Asp Ala Trp Arg Phe Asp Tyr Val Lys Gly Tyr Gly Ala Trp
            245                 250                 255

Val Val Lys Asp Trp Leu Lys Trp Trp Ala Leu Ala Val Gly Glu Tyr
            260                 265                 270

Trp Asp Thr Asn Val Asp Ala Leu Leu Asn Trp Ala Tyr Ser Ser Gly
            275                 280                 285

Ala Lys Val Phe Asp Phe Pro Leu Tyr Tyr Lys Met Asp Glu Ala Phe
            290                 295                 300

Asp Asn Lys Asn Ile Pro Ala Leu Val Ser Ala Leu Gln Asn Gly Gln
305                 310                 315                 320

Thr Val Val Ser Arg Asp Pro Phe Lys Ala Val Thr Phe Val Ala Asn
            325                 330                 335

His Asp Thr Asp Ile Ile Trp Asn Lys Tyr Pro Ala Tyr Ala Phe Ile
            340                 345                 350

Leu Thr Tyr Glu Gly Gln Pro Val Ile Phe Tyr Arg Asp Tyr Glu Glu
            355                 360                 365

Trp Leu Asn Lys Asp Arg Leu Lys Asn Leu Ile Trp Ile His Asn Asn
            370                 375                 380

Leu Ala Gly Gly Ser Thr Ser Ile Val Tyr Tyr Asp Asn Asp Glu Leu
385                 390                 395                 400

Ile Phe Val Arg Asn Gly Tyr Gly Asn Lys Pro Gly Leu Ile Thr Tyr
            405                 410                 415

Ile Asn Leu Gly Ser Ser Lys Val Gly Arg Trp Val Tyr Val Pro Lys
            420                 425                 430

Phe Ala Gly Ser Cys Ile His Glu Tyr Thr Gly Asn Leu Gly Gly Trp
            435                 440                 445

Val Asp Lys Tyr Val Gly Ser Asn Gly Trp Val Tyr Leu Glu Ala Pro
            450                 455                 460

Ala His Asp Pro Ala Lys Gly Gln Tyr Gly Tyr Ser Val Trp Ser Tyr
465                 470                 475                 480

Cys Gly Val Gly

<210> SEQ ID NO 49
<211> LENGTH: 457
```

```
<212> TYPE: PRT
<213> ORGANISM: Artificial Sequence
<220> FEATURE:
<223> OTHER INFORMATION: Synthetic protein

<400> SEQUENCE: 49
```

| | | | | | | | | | | | | | | | |
|---|---|---|---|---|---|---|---|---|---|---|---|---|---|---|---|
| Met | Ala | Arg | Lys | Val | Leu | Val | Ala | Leu | Leu | Val | Phe | Leu | Val | Val | Leu |
| 1 | | | | 5 | | | | | 10 | | | | | 15 | |
| Ser | Val | Ser | Ala | Val | Pro | Ala | Lys | Ala | Glu | Thr | Leu | Glu | Asn | Gly | Gly |
| | | | 20 | | | | | 25 | | | | | 30 | | |
| Val | Ile | Met | Gln | Ala | Phe | Tyr | Trp | Asp | Val | Pro | Gly | Gly | Gly | Ile | Trp |
| | | | | 35 | | | | | 40 | | | | | 45 | |
| Trp | Asp | Thr | Ile | Ala | Gln | Lys | Ile | Pro | Asp | Trp | Ala | Ser | Ala | Gly | Ile |
| | 50 | | | | | 55 | | | | | 60 | | | | |
| Ser | Ala | Ile | Trp | Ile | Pro | Pro | Ala | Ser | Lys | Gly | Met | Ser | Gly | Gly | Tyr |
| 65 | | | | | 70 | | | | | 75 | | | | | 80 |
| Ser | Met | Gly | Tyr | Asp | Pro | Tyr | Asp | Phe | Phe | Asp | Leu | Gly | Glu | Tyr | Tyr |
| | | | | 85 | | | | | 90 | | | | | 95 | |
| Gln | Lys | Gly | Ser | Val | Glu | Thr | Arg | Phe | Gly | Ser | Lys | Glu | Glu | Leu | Val |
| | | | 100 | | | | | 105 | | | | | 110 | | |
| Asn | Met | Ile | Asn | Thr | Ala | His | Ala | His | Asn | Met | Lys | Val | Ile | Ala | Asp |
| | | | | 115 | | | | | 120 | | | | | 125 | |
| Ile | Val | Ile | Asn | His | Arg | Ala | Gly | Gly | Asp | Leu | Glu | Trp | Asn | Pro | Phe |
| | 130 | | | | | 135 | | | | | 140 | | | | |
| Thr | Asn | Ser | Tyr | Thr | Trp | Thr | Asp | Phe | Ser | Lys | Val | Ala | Ser | Gly | Lys |
| 145 | | | | | 150 | | | | | 155 | | | | | 160 |
| Tyr | Thr | Ala | Asn | Tyr | Leu | Asp | Phe | His | Pro | Asn | Glu | Leu | His | Ala | Gly |
| | | | | 165 | | | | | 170 | | | | | 175 | |
| Asp | Ser | Gly | Thr | Phe | Gly | Gly | Tyr | Pro | Asp | Ile | Cys | His | Asp | Lys | Ser |
| | | | 180 | | | | | 185 | | | | | 190 | | |
| Trp | Asp | Gln | His | Trp | Leu | Trp | Ala | Ser | Asn | Glu | Ser | Tyr | Ala | Ala | Tyr |
| | | | | 195 | | | | | 200 | | | | | 205 | |
| Leu | Arg | Ser | Ile | Gly | Ile | Asp | Ala | Trp | Arg | Phe | Asp | Tyr | Val | Lys | Gly |
| | 210 | | | | | 215 | | | | | 220 | | | | |
| Tyr | Ala | Pro | Trp | Val | Val | Lys | Asn | Trp | Leu | Asn | Arg | Trp | Gly | Gly | Trp |
| 225 | | | | | 230 | | | | | 235 | | | | | 240 |
| Ala | Val | Gly | Glu | Tyr | Trp | Asp | Thr | Asn | Val | Asp | Ala | Leu | Leu | Ser | Trp |
| | | | | 245 | | | | | 250 | | | | | 255 | |
| Ala | Tyr | Asp | Ser | Gly | Ala | Lys | Val | Phe | Asp | Phe | Pro | Leu | Tyr | Tyr | Lys |
| | | | 260 | | | | | 265 | | | | | 270 | | |
| Met | Asp | Glu | Ala | Phe | Asp | Asn | Asn | Ile | Pro | Ala | Leu | Val | Asp | Ala | |
| | | | 275 | | | | | 280 | | | | | 285 | | |
| Leu | Lys | Asn | Gly | Gly | Thr | Val | Val | Ser | Arg | Asp | Pro | Phe | Lys | Ala | Val |
| | 290 | | | | | 295 | | | | | 300 | | | | |
| Thr | Phe | Val | Ala | Asn | His | Asp | Thr | Asn | Ile | Ile | Trp | Asn | Lys | Tyr | Pro |
| 305 | | | | | 310 | | | | | 315 | | | | | 320 |
| Ala | Tyr | Ala | Phe | Ile | Leu | Thr | Tyr | Glu | Gly | Gln | Pro | Ala | Ile | Phe | Tyr |
| | | | | 325 | | | | | 330 | | | | | 335 | |
| Arg | Asp | Tyr | Glu | Glu | Trp | Leu | Asn | Lys | Asp | Arg | Leu | Arg | Asn | Leu | Ile |
| | | | 340 | | | | | 345 | | | | | 350 | | |
| Trp | Ile | His | Asp | His | Leu | Ala | Gly | Gly | Ser | Thr | Asp | Ile | Ile | Tyr | Tyr |
| | | | | 355 | | | | | 360 | | | | | 365 | |
| Asp | Ser | Asp | Glu | Leu | Ile | Phe | Val | Arg | Asn | Gly | Tyr | Gly | Asp | Lys | Pro |
| | 370 | | | | | 375 | | | | | 380 | | | | |

```
Gly Leu Ile Thr Tyr Ile Asn Leu Gly Ser Ser Lys Ala Gly Arg Trp
385                 390                 395                 400

Val Tyr Val Pro Lys Phe Ala Gly Ser Cys Ile His Glu Tyr Thr Gly
            405                 410                 415

Asn Leu Gly Gly Trp Ile Asp Lys Trp Val Asp Ser Ser Gly Arg Val
        420                 425                 430

Tyr Leu Glu Ala Pro Ala His Asp Pro Ala Asn Gly Gln Tyr Gly Tyr
    435                 440                 445

Ser Val Trp Ser Tyr Cys Gly Val Gly
    450                 455
```

<210> SEQ ID NO 50
<211> LENGTH: 463
<212> TYPE: PRT
<213> ORGANISM: Artificial Sequence
<220> FEATURE:
<223> OTHER INFORMATION: Synthetic protein

<400> SEQUENCE: 50

```
Met Arg Arg Ser Ala Arg Val Leu Val Leu Ile Ile Ala Phe Phe Leu
1               5                   10                  15

Leu Ala Gly Ile Tyr Tyr Pro Ser Thr Ser Ala Ala Lys Tyr Ser Glu
            20                  25                  30

Leu Glu Gln Gly Gly Val Ile Met Gln Ala Phe Tyr Trp Asp Val Pro
        35                  40                  45

Glu Gly Gly Ile Trp Trp Asp Thr Ile Arg Gln Lys Ile Pro Glu Trp
    50                  55                  60

Tyr Asp Ala Gly Ile Ser Ala Ile Trp Ile Pro Ala Ser Lys Gly
65                  70                  75                  80

Met Gly Gly Ala Tyr Ser Met Gly Tyr Asp Pro Tyr Asp Tyr Phe Asp
                85                  90                  95

Leu Gly Glu Phe Tyr Gln Lys Gly Thr Val Glu Thr Arg Phe Gly Ser
            100                 105                 110

Lys Glu Glu Leu Val Asn Met Ile Ser Thr Ala His Gln Tyr Gly Ile
        115                 120                 125

Lys Val Ile Ala Asp Ile Val Ile Asn His Arg Ala Gly Gly Asp Leu
    130                 135                 140

Glu Trp Asn Pro Tyr Val Gly Asp Tyr Thr Trp Thr Asp Phe Ser Lys
145                 150                 155                 160

Val Ala Ser Gly Lys Tyr Lys Ala His Tyr Met Asp Phe His Pro Asn
                165                 170                 175

Asn Tyr Ser Thr Ser Asp Glu Gly Thr Phe Gly Gly Phe Pro Asp Ile
            180                 185                 190

Asp His Leu Val Pro Phe Asn Gln Tyr Trp Leu Trp Ala Ser Asn Glu
        195                 200                 205

Ser Tyr Ala Ala Tyr Leu Arg Ser Ile Gly Ile Asp Ala Trp Arg Phe
    210                 215                 220

Asp Tyr Val Lys Gly Tyr Gly Ala Trp Val Val Lys Asp Trp Leu Ser
225                 230                 235                 240

Gln Trp Gly Gly Trp Ala Val Gly Glu Tyr Trp Asp Thr Asn Val Asp
                245                 250                 255

Ala Leu Leu Asn Trp Ala Tyr Ser Ser Gly Ala Lys Val Phe Asp Phe
            260                 265                 270

Pro Leu Tyr Tyr Lys Met Asp Glu Ala Phe Asp Asn Lys Asn Ile Pro
        275                 280                 285
```

```
Ala Leu Val Tyr Ala Ile Gln Asn Gly Glu Thr Val Val Ser Arg Asp
        290                 295                 300

Pro Phe Lys Ala Val Thr Phe Val Ala Asn His Asp Thr Asn Ile Ile
305                 310                 315                 320

Trp Asn Lys Tyr Pro Ala Tyr Ala Phe Ile Leu Thr Tyr Glu Gly Gln
                325                 330                 335

Pro Val Ile Phe Tyr Arg Asp Tyr Glu Glu Trp Leu Asn Lys Asp Lys
                340                 345                 350

Leu Asn Asn Leu Ile Trp Ile His Glu His Leu Ala Gly Gly Ser Thr
            355                 360                 365

Lys Ile Leu Tyr Tyr Asp Asp Asp Glu Leu Ile Phe Met Arg Glu Gly
370                 375                 380

Tyr Gly Asp Arg Pro Gly Leu Ile Thr Tyr Ile Asn Leu Gly Ser Asp
385                 390                 395                 400

Trp Ala Glu Arg Trp Val Asn Val Gly Ser Lys Phe Ala Gly Tyr Thr
                405                 410                 415

Ile His Glu Tyr Thr Gly Asn Leu Gly Gly Trp Val Asp Arg Tyr Val
                420                 425                 430

Gln Tyr Asp Gly Trp Val Lys Leu Thr Ala Pro Pro His Asp Pro Ala
            435                 440                 445

Asn Gly Tyr Tyr Gly Tyr Ser Val Trp Ser Tyr Ala Gly Val Gly
        450                 455                 460

<210> SEQ ID NO 51
<211> LENGTH: 463
<212> TYPE: PRT
<213> ORGANISM: Artificial Sequence
<220> FEATURE:
<223> OTHER INFORMATION: Synthetic protein

<400> SEQUENCE: 51

Met Arg Arg Ser Ala Arg Val Leu Val Leu Ile Ile Ala Phe Phe Leu
1               5                   10                  15

Leu Ala Gly Ile Tyr Tyr Pro Ser Thr Ser Ala Ala Lys Tyr Ser Glu
            20                  25                  30

Leu Glu Gln Gly Gly Val Ile Met Gln Ala Phe Tyr Trp Asp Val Pro
        35                  40                  45

Glu Gly Gly Ile Trp Trp Asp Thr Ile Arg Gln Lys Ile Pro Glu Trp
50                  55                  60

Tyr Asp Ala Gly Ile Ser Ala Ile Trp Ile Pro Pro Ala Ser Lys Gly
65                  70                  75                  80

Met Gly Gly Ala Tyr Ser Met Gly Tyr Asp Pro Tyr Asp Tyr Phe Asp
                85                  90                  95

Leu Gly Glu Phe Tyr Gln Lys Gly Thr Val Glu Thr Arg Phe Gly Ser
            100                 105                 110

Lys Glu Glu Leu Val Asn Met Ile Ser Thr Ala His Gln Tyr Gly Ile
        115                 120                 125

Lys Val Ile Ala Asp Ile Val Ile Asn His Arg Ala Gly Gly Asp Leu
130                 135                 140

Glu Trp Asn Pro Tyr Val Gly Asp Tyr Thr Trp Thr Asp Phe Ser Lys
145                 150                 155                 160

Val Ala Ser Gly Lys Tyr Lys Ala His Tyr Met Asp Phe His Pro Asn
                165                 170                 175

Asn Tyr Ser Thr Ser Asp Glu Gly Thr Phe Gly Gly Phe Pro Asp Ile
            180                 185                 190
```

```
                    -continued

Asp His Leu Val Pro Phe Asn Gln Tyr Trp Leu Trp Ala Ser Asn Glu
    195                 200                 205

Ser Tyr Ala Ala Tyr Leu Arg Ser Ile Gly Ile Asp Ala Trp Arg Phe
    210                 215                 220

Asp Tyr Val Lys Gly Tyr Gly Ala Trp Val Val Lys Asp Trp Leu Ser
225                 230                 235                 240

Gln Trp Gly Gly Trp Ala Val Gly Glu Tyr Trp Asp Thr Asn Val Asp
                245                 250                 255

Ala Leu Leu Asn Trp Ala Tyr Ser Ser Gly Ala Lys Val Phe Asp Phe
            260                 265                 270

Pro Leu Tyr Tyr Lys Met Asp Glu Ala Phe Asp Asn Lys Asn Ile Pro
        275                 280                 285

Ala Leu Val Tyr Ala Ile Gln Asn Gly Glu Thr Val Val Ser Arg Asp
    290                 295                 300

Pro Phe Lys Ala Val Thr Phe Val Ala Asn His Asp Thr Asn Ile Ile
305                 310                 315                 320

Trp Asn Lys Tyr Pro Ala Tyr Ala Phe Ile Leu Thr Tyr Glu Gly Gln
                325                 330                 335

Pro Val Ile Phe Tyr Arg Asp Tyr Glu Glu Trp Leu Asn Lys Asp Lys
            340                 345                 350

Leu Asn Asn Leu Ile Trp Ile His Glu His Leu Ala Gly Gly Ser Thr
        355                 360                 365

Lys Ile Leu Tyr Tyr Asp Asp Asp Glu Leu Ile Phe Met Arg Glu Gly
    370                 375                 380

Tyr Gly Asp Arg Pro Gly Leu Ile Thr Tyr Ile Asn Leu Gly Ser Asp
385                 390                 395                 400

Trp Ala Glu Arg Trp Val Asn Val Gly Ser Lys Phe Ala Gly Tyr Thr
                405                 410                 415

Ile His Glu Tyr Thr Gly Asn Leu Gly Gly Trp Val Asp Arg Tyr Val
            420                 425                 430

Gln Tyr Asp Gly Trp Val Lys Leu Thr Ala Pro Pro His Asp Pro Ala
        435                 440                 445

Asn Gly Tyr Tyr Gly Tyr Ser Val Trp Ser Tyr Ala Gly Val Gly
    450                 455                 460
```

USES OF SURFACTANTS IN STARCH PROCESSING

CROSS-REFERENCE TO RELATED APPLICATIONS

The present application claims the benefit of priority to U.S. Application No. 62/676,477, filed on May 25, 2018, the contents of which are incorporated herein in their entirety.

REFERENCE TO SEQUENCE LISTING

The present application is being filed along with a Sequence Listing in electronic format. The Sequence Listing is provided as a file entitled Sequence-Listing-BASF-063PR.txt, created May 25, 2018, which is 188 Kb in size. The information in the electronic format of the Sequence Listing is incorporated herein by reference in its entirety.

BACKGROUND

Field

The present application relates to processes of producing fermentation products, such as ethanol from starch-containing material using a fermenting organism. One aspect relates to the reduction of slurry viscosity by the addition of one or more surfactants and one or more amylases.

Description of Related Art

Production of fermentation products, such as ethanol, from starch-containing materials is well-known in the art. Liquefaction methods often involve a starch gelatinization process, wherein aqueous starch slurry is heated so that the granular starch in the slurry swells and bursts, dispersing starch molecules into the solution. During the gelatinization process, there is a dramatic increase in viscosity. To enable handling during the remaining process steps, the starch must be thinned or "liquefied".

Various strategies for reducing slurry viscosity during starch processing are currently available depending upon the processing system, starch type, and desired end product. There is still a need for effective methods for reducing the viscosity of the slurry in the slurry tanks and liquefaction tanks to enhance mash formation, preliquefaction, gelatinization, liquefaction, saccharification, fermentation, and end product recovery.

SUMMARY

In several embodiments, methods of starch production are provided. Methods of reducing the viscosity of a slurry are also provided herein in some embodiments. In some embodiments, the method comprises (a) providing an amylase, (b) providing a surfactant, and (c) adding the amylase of (a) and the surfactant of (b) to a slurry and/or liquefaction tank comprising a starch. In some embodiments, the amylase and/or surfactant are added to slurry tank and/or liquefaction tank during a preliquefying stage; a gelatinizing stage; and/or a liquefying stage. In some embodiments, the surfactant comprises two or more surfactants. In some embodiments, the amylase comprises two or more amylases. In some embodiments of the methods provided herein, the peak viscosity and/or final viscosity of the slurry tank and/or liquefaction tank is reduced by at least 3% (e.g., 3%, 4%, 5%, 10%, 15%, 20%, 25%, 30%, 40%, 50%, 60%, 70%, 80%, 90%, 100%, and overlapping ranges) compared to a slurry not treated with the one or more surfactants. In some embodiments, the surfactant is present in an amount of at least 0.01 wt % (e.g., 0.01, 0.02, 0.03, 0.04, 0.05, 0.06, 0.07, 0.08, 0.09, 0.1, 0.15, 0.2, 0.25, 0.3, 0.35, 0.4, 0.45, 0.5 or higher, and ranges in between any two of these values). In some embodiments, the surfactant comprises an amphoteric surfactant (e.g., cocamidopropyl betaine and/or cocamidopropylamine oxide) and/or an anionic surfactant (e.g., alkyl sulfates, alkyl ether sulfates, alkylphenol ether sulfates, and/or phosphate esters). In some embodiments, the one or more surfactants comprises a nonionic surfactant, such as, for example, alcohol alkoxylates, alkylphenol ethoxylates, block copolymers of EO/PO, block copolymers of ethylene diamine, alkyl polyglycosides, glycerol esters, polyethylene glycol esters, functionalized polyols, sorbitan esters, ethoxylated sorbitan esters, alkoxylated sorbitan esters, natural oil alkoxylates, polyoxyalkylene glycols, and any combination thereof. In several embodiments, the surfactant has an hydrophilic-lipophilic balance (HLB) value that is greater than 2 (e.g., 2, 3, 4, 5, 6, 7, 8, 9, 10, 11, 12, 13, 14, 15, 16, 17, 18, 19, 20, 25, 30, or higher and overlapping ranges therein). In some embodiments, the one or more surfactants comprises one or more of Lutensol A65N, Lutensol XP 90, Lutensol AO 8, Pluronic P 104, Agnique CSO-30, Lutensol A03, Pluronic L61, Tetronic 1304, and Agnique SBO 30.

In some embodiments, preliequfaction is performed at a temperature between about 45° C. to 70° C., (e.g., 45° C., 50° C., 55° C., 60° C., 65° C., 70° C., and ranges in between any two of these values). In some embodiments, preliequfaction is performed for a period of about 20-240 minutes (e.g., 20 min, 30 min, 50 min, 70 min, 90 min, 110 min, 130 min, 150 min, 170 min, 190 min, 210 min, 230 min, 240 min, and ranges in between any two of these values). In some embodiments, gelatinization is by jet-cooking at appropriate conditions, such as, e.g. at a temperature between 95-140° C., (e.g., 85° C., 95° C., 105° C., 115° C., 125° C., 135° C., 140° C., and ranges in between any two of these values) to complete gelatinization of the starch. In some embodiments, the gelatinization step is performed for a period of about 1-15 minutes (e.g., 1, 2, 3, 4, 5, 6, 7, 8, 9, 10, 11, 12, 13, 14, 15, and ranges in between any two of these values). In some embodiments, the liquefaction step is performed at a temperature between about 60-95° C., (e.g., 60° C., 65° C., 70° C., 75° C., 80° C., 85° C., 90° C., 95° C., and ranges in between any two of these values). In some embodiments, the liquefaction step is performed for a period of about 20-240 minutes (e.g., 20 min, 30 min, 50 min, 70 min, 90 min, 110 min, 130 min, 150 min, 170 min, 190 min, 210 min, 230 min, 240 min, and ranges in between any two of these values). In some embodiments, the liquefaction is performed at a pH in the range of 3.5-7.0 (e.g., 3.5, 4.0, 4.5, 5.0, 5.5, 6.0, 6.5, 7.0 and ranges in between any two of these values).

In some embodiments, the methods herein further comprise adding a surfactant to a stillage (e.g., a whole stillage, a thin stillage, a wet cake, and/or a syrup), a separator, a corn oil extraction, or any combination thereof. In some embodiments, the methods provided herein further comprise fermentation in the presence of a microorganism (e.g., a bacterial species, a yeast species, and/or a fungal species). In some such embodiments, the fermentation rate is increased by at least 5% (e.g., 5%, 10%, 15%, 20%, 25%, 30%, 40%, 50%, 60%, 70%, 80%, 90%, 100%, and overlapping ranges) compared to a slurry not treated with the one or more surfactants. In some embodiments, the methods provided herein further comprise recovering a fermentation product, such as, for example, alcohols, acids, ketones, amino acids, antibiotics, enzymes, vitamins, hormones, and any combination thereof. In further embodiments, the fermentation product is ethanol. In some such embodiments, the yield and/or rate of ethanol production is increased, the rate of ethanol production is increased. In some embodiments of the methods provided herein, components of the slurry are not separated and reconstituted. In some embodiments, the methods do not comprise adjusting the pH of the slurry. In some embodiments, the methods do not comprise adding an acid (e.g., methanesulfonic acid, sulfuric acid, hydrochloric acid, acetic acid, tartaric acid, lactic acid, citric acid, an alkanesulfonic acid) to a slurry.

In some embodiments, the methods further comprise distilling a beer to produce ethanol and whole stillage. In some such embodiments, the whole stillage may be processed to produce one or more of wet distiller's grains with solubles (WDGS), dried distiller's grains with solubles (DDGS), and corn oil. In some embodiments, the corn oil yield is increased by at least about 5% (e.g., 5%, 10%, 15%, 20%, 25%, 30%, 40%, 50%, 60%, 70%, 80%, 90%, 100%, and overlapping ranges) as compared to a comparable method performed in the absence of said one or more surfactants in the slurry. In some embodiments, the amount of residual starch is reduced by at least about 5% (e.g., 5%, 10%, 15%, 20%, 25%, 30%, 40%, 50%, 60%, 70%, 80%, 90%, 100%, and overlapping ranges) as compared to a comparable method performed in the absence of said one or more surfactants in the slurry.

In some embodiments, the amylase (e.g., an alpha amylase, a beta amylase, and/or a gamma amylase) is present in an amount of from about 0.001 to about 0.2 wt % (e.g., 0.001%, 0.005%, 0.01%, 0.03%, 0.05%, 0.07%, 0.09%, 0.1%, 0.11%, 0.13%, 0.15%, 0.17%, 0.19%, 0.2% and ranges in between). In some embodiments, the alpha amylase is a polypeptide comprising an amino acid sequence at least 85% (e.g., 85%, 87%, 90%, 93%, 95%, 97%, 99%, 100%, and overlapping ranges) identical to any one of the amino acid sequences of SEQ ID NO:1 to SEQ ID NO:51. In several embodiments, one or more additional enzymes are added the process stream (e.g. the mash, the slurry, or the liquefact) in an amount ranging from about 0.001% to about 0.2 wt % (e.g., 0.001%, 0.005%, 0.01%, 0.03%, 0.05%, 0.07%, 0.09%, 0.1%, 0.11%, 0.13%, 0.15%, 0.17%, 0.19%, 0.2% and ranges in between) based on a total weight of the starch-containing material. Additional enzymes include, but are not limited to, a phytase, cellulase, protease, aminopeptidase, amylase, beta-amylase, carbohydrase, carboxypeptidase, catalase, chitinase, cutinase, cyclodextrin glucanotransferase, deoxyribonuclease, esterase, α-galactosidase, β-galactosidase, glucoamylase, α-glucosidase, β-glucosidase, haloperoxidase, invertase, isomerase, laccase, lipase, mannosidase, oxidase, pectinase, peptidoglutaminase, peroxidase, polyphenoloxidase, nuclease, ribonuclease, transglutaminase, xylanase, pullulanase, isoamylase, carrageenase, and/or protease.

DETAILED DESCRIPTION

Figure 1:
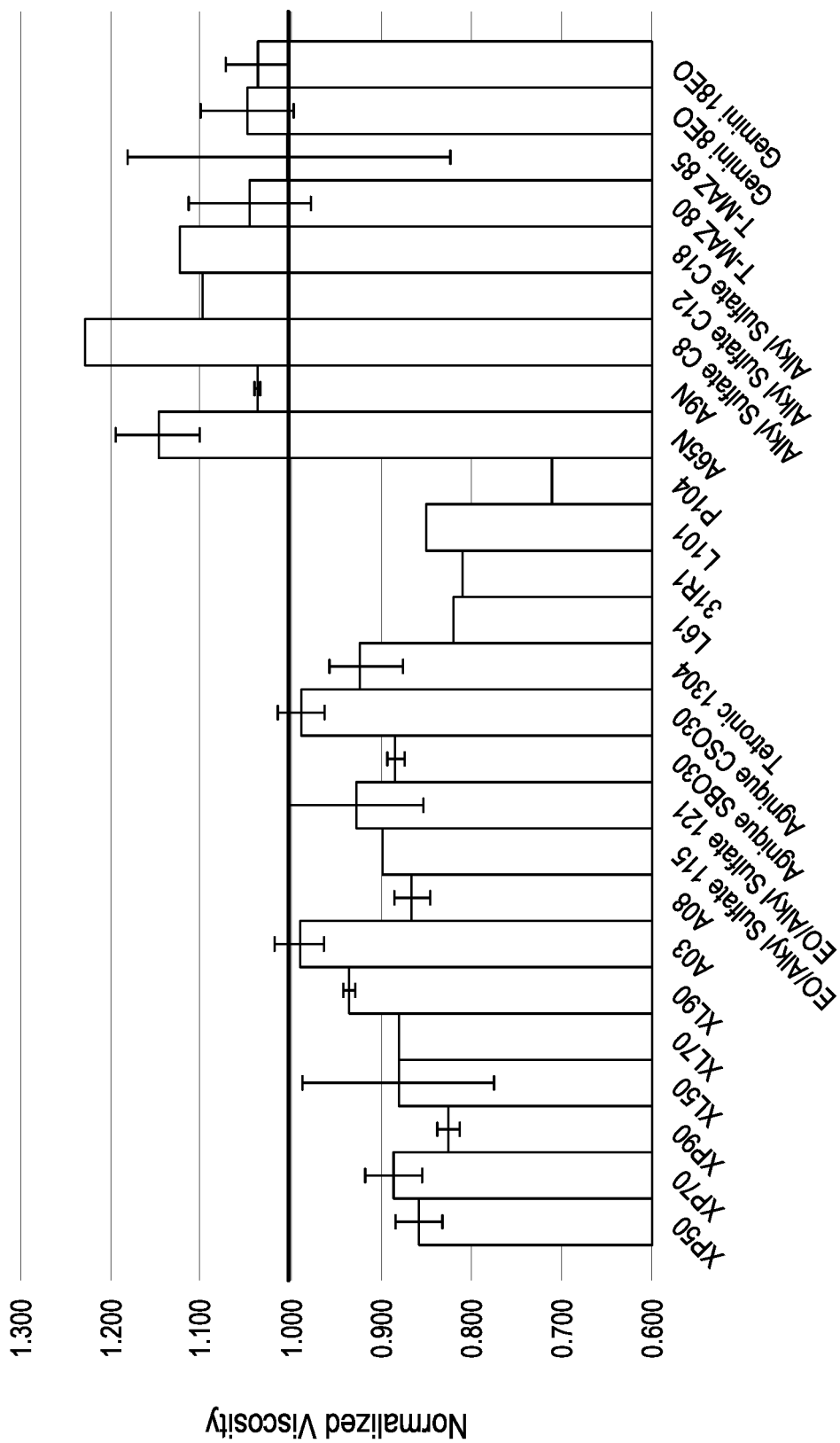
FIG. 1 depicts the normalized viscosity of samples containing the indicated surfactants.

In the following detailed description, reference is made to the accompanying drawings, which form a part hereof. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, can be arranged, substituted, combined, and designed in a wide variety of different configurations, all of which are explicitly contemplated and make part of this disclosure.

Starch-Containing Materials

The present disclosure provides improved methods of starch processing ("the process"). Plants are often used as a source for starch, which can be used to produce ethanol and other products. Plant starches are generally in a granular form, which is insoluble in water. A variety of different starch-containing plant material can be employed in the starch processing methods disclosed herein. As used herein, the phrase "starch-containing material" refers to any materials comprising starch. For example, a "starch-containing plant material" refers to all or part of any plant material that includes starch. In some embodiments, starch-containing material can be a grain, fruit, seed, stalk, wood, vegetable, or root. For example, the starch-containing material can be obtained from any plant including, but not limited to, sorghum (milo), oats, barley, wheat, berry, grape, rye, maize (corn), rice, potato, sugar beet, sugarcane, pineapple, yarns, plantain, banana, grasses or trees. Non-limiting examples of starch-containing material include grains such as maize (corn, e.g., whole ground corn), sorghum (milo), barley, wheat, rye, rice, and millet; and starchy root crops, tubers, or roots such as potato, sweet potato, and cassava. The starch-containing plant material can, for example, be obtained as a previously treated plant product such as soy cake generated during the processing of soybeans. In some embodiments, the plant material is a mixture of such materials and by-products of such materials, e.g., corn fiber, corn cobs, stover, or other cellulose- and hemicellulose-containing materials, such as wood or plant residues. In some embodiments, the starch-containing plant material is corn, including standard corn and/or waxy corn.

In some embodiments, the starch-containing material, such as whole grains, may be reduced in particle size, e.g., by milling, in order to open up the structure and allowing for further processing. In some embodiments, the particle size is reduced to between 0.05 to 3.0 mm, (e.g., 0.05, 0.1, 0.2, 0.3, 0.4, 0.5, 0.6, 0.7, 0.8, 0.9, 1.0, 1.3, 1.5, 1.8, 2.0, 2.3, 2.5, 2.7, 3.0, and ranges in between). In some embodiments, the particle size is reduced so that at least 30% (e.g., 30%, 40%, 50%, 60%, 70%, 80%, 90%, 100%, and ranges in between) of the starch-containing material fit through a sieve with a 0.05 to 3.0 mm screen, preferably 0.1-0.5 mm screen. It is contemplated that methods disclosed herein can be used in conjunction with any milling technique employed to process the plant material, including, but not limited to, wet milling, dry milling, dry grinding, cracking, coarse grinding, fine grinding, fractionating, mixing, flaking, steam flaking, rolling or chopping. In some embodiments, the process comprises wet-milling or dry-milling. In some embodiments, the process comprises a wet-milling (wet-grind) process including an initial grain treatment step wherein the corn kernels are steeped in water, and then separated for processing. In dry milling, the whole kernel is milled and used in the remaining part of the process. In some embodiments, the process comprises a dry-milling (dry-grind) process including an initial grain treatment step of grinding corn kernels to form a corn flour. In some embodiments, the ground corn flour is then fractionated into bran, germ and grits (starchy fractions). In some embodiments, the step of grinding the corn kernels is further defined as milling the kernels into coarse flour. In some embodiments, the course flour includes corn fiber. In some embodiments, the milled kernels are passed through a fine mesh screen to yield the corn flour. The step of grinding the corn kernels can vary in time because the flour yielded should have a particle size that provides enough surface area to make starch granules available for reaction with water and enzymes and also leaves enough flour to produce wet distillers grains plus solubles (WDGS) that can be dried to produce dried distillers grains plus solubles (DDGS).

There remains a need to optimize the production of ethanol, corn oil, and other co-products produced by starch processing. For example, there remains an opportunity to improve the viscosity of the slurry, given its significant impact on downstream processes and the yield and/or quality of end products. Several embodiments of the present invention relate to unique methods of reducing the viscosity of a starch slurry during starch processing by the addition of one or more surfactants. In some embodiments, the methods described herein provides one or more of the following advantages over conventional processes: (i) increased fermentation rate; (ii) reduction in residual starch; (iii) reduced peak viscosity; (iv) reduced final viscosity; (v) increased ethanol production rate; (vi) reduced process time(s) (e.g., the incubation periods of one or more steps of the process are diminished); (vii) reduced process temperature(s) (e.g., the temperatures of one or more steps of the process are reduced); (viii) improved enzyme activity (e.g., improved access to substrates); (ix) improved ethanol yield; (x) reduced enzyme levels required; (xi) reduced formation of Maillard reaction products, (xii) improved enzyme half-life; (xiii) reduced thickening of the post-liquefaction slurry when cooled to ambient temperature; (xiv) improved DDG and DDGS consistency; (xv) improved DDG and DDGS consistency physical characteristics (e.g. flowability, color, odor); (xvi) improved DDG and DDGS composition (e.g. protein and fiber content); (xvii) increasing the percentage of solids used to create the mash; (xviii) removing the use of a jet cooker; and (xix) decreased mixing. Advantageously, in several embodiments, these improvements are obtained with methods that are cost-effective, with no or little deleterious effects on recovered end products.

Slurry Formation and Liquefaction

In some embodiments, the method disclosed herein includes the step of adding a surfactant to a process stream of the process. The surfactant can be added at one or more points in the process. The point(s) at which the surfactant is added to the process stream is also not limited. In some embodiments of the methods provided herein, one or more surfactants is added to the slurry. In the various embodiments of this disclosure, the process stream changes as the starch processing progresses and reference to the mash, the slurry, the beer, etc. are used to represent the process stream, which is dynamic. For example, the mash can include different components during the various steps of the process but still be referred to as the mash. As another example, the mash can be referred to as the slurry during the various steps of the process. As used herein, the term "slurry" shall be given its ordinary meaning and shall also refer to a mixture of starch or a starch-containing material (e.g., milled corn) and an aqueous component, which can include, for example, water, de-ionized water, or a process water (i.e., backset, steam, condensate), or any combination thereof. The terms slurry and mash and liquefact can be used interchangeably.

Some embodiments disclosed herein relate generally to methods for starch processing that can be described as separated into the following main process stages: (a) mash formation; (b) preliquefaction; (c) gelatinization; (d); liquefaction; (e) saccharification and fermentation, wherein the steps (a), (b), (c), (d) and (e) is performed in the order (a), (b), (c), (d) and (e). Step (e) may be performed as a simultaneous saccharification and fermentation (SSF) or as two separate sub steps. In some embodiments, one or more of steps (a), (b), (c), (d), and/or (e) are optional. In some embodiments, one or more of steps (a), (b), (c), (d), and/or (e) are performed in the presence of a surfactant, said surfactant being present in an amount of at least 0.01 wt % (e.g., 0.01, 0.02, 0.03, 0.04, 0.05, 0.06, 0.07, 0.08, 0.09, 0.1, 0.15, 0.2, 0.25, 0.3, 0.35, 0.4, 0.45, 0.5 or higher, and ranges in between any two of these values). One or more of steps (a), (b), (c), (d), and/or (e) are performed in a slurry tank in some embodiments. One or more of steps (a), (b), (c), (d), and/or (e) are performed in a liquefaction tank in some embodiments. In some embodiments, the surfactant usually need only be added once to the process, e.g. before or during the preliquefaction step (b), in order to be present and/or active during the process steps (b), (c) and/or (d). In some embodiments, steps (a), (b), (c), and (d) do not comprise extracting corn oil.

In some embodiments of the methods provided here, the process further comprises step (f) recovering the fermentation product (end product). As used herein, the terms "end-product" or "desired end-product" refer to a molecule that is enzymatically derived from a substrate, such as starch. In some embodiments, step (f) comprises distilling the beer to produce ethanol and whole stillage. In some embodiments, step (f) further comprises processing the whole stillage to produce one or more of wet distiller's grains with solubles (WDGS), dried distiller's grains with solubles (DDGS), and/or corn oil. In some such embodiments, step (f) comprises the substeps of i) centrifuging the whole stillage to produce wet cake and thin stillage; ii) evaporating water from the thin stillage to form a syrup; and iii) extracting corn oil from the syrup. In some embodiments, step (f) further comprises the sub steps of: iv) combining the wet cake and the syrup having the corn oil removed therefrom to form WDGS; and optionally v) drying the WDGS to produce DDGS. In some embodiments, step (f) is performed in the presence of a surfactant, said surfactant being present in an amount of at least 0.01 wt %. Some embodiments of the methods provided herein further comprise adding a surfactant to a stillage (whole stillage, a think stillage, a wet cake, and/or a syrup), a sperator, a corn oil extraction, or any combination thereof.

In some embodiments, the mash is provided by forming a slurry comprising the milled starch containing material and a liquid. In some embodiments, the liquid comprises or is derived from a water, a stillage, or any combination thereof. In some embodiments, the water comprises or is derived from fresh water, backset, cook water, process water, lutter water, evaporation water, or any combination thereof. In several embodiments, one or more surfactants are added to the slurry before, during, or immediately after the mash formation step. In order to facilitate wetting or mixing the aqueous mash, the step of providing the aqueous mash can comprise holding the mash in a tank (i.e., a pre-slurry tank) for a period of time prior to the heating step. Any suitable mixing method can be used, including any suitable manual or mechanical mixing method that can be used in conjunction with the pre-slurry, slurry and liquefaction tanks. If the mash is prepared in a separate tank or vessel than that in which the heating will take place, the mash can be moved to the heating tank by any suitable approach (e.g., pouring, pumping, or the like). In some embodiments, the mash is formed in a vessel termed a slurry tank. As used herein, the term "slurry tank" shall be given its ordinary meaning and shall also refer to a vessel, unit, or tank used to contain ground plant material combined with a liquid. A slurry tank can be the slurry tank used in a commercial production setting which may be a dry grind ethanol plant, a grain milling plant using a wet or dry milling process to mill corn grain or may be a food production plant that is combining ground plant flour with liquids in order to form a dough. In some embodiments, the liquid is heated to a suitable temperature prior to being combined with the milled starch containing material. In some embodiments, the mash formation is performed at a temperature between about 45° C. to 70° C., (e.g., 45° C., 50° C., 55° C., 60° C., 65° C., 70° C., and ranges in between any two of these values). In some embodiments, the dry solids % (dry solid percentage) in the slurry tank (containing milled whole grain) is in the range from 1-60%, in particular 10-50%, such as 20-40%, such as 25-35%. In some embodiments, the mash formation step is performed for a period of about 20-240 minutes (e.g., 20 min, 30 min, 50 min, 70 min, 90 min, 110 min, 130 min, 150 min, 170 min, 190 min, 210 min, 230 min, 240 min, and ranges in between any two of these values). In some embodiments, the mash formation is performed at a pH in the range of 3.5-7.0 (e.g., 3.5, 4.0, 4.5, 5.0, 5.5, 6.0, 6.5, 7.0, and ranges in between any two of these values). In some embodiments, the pH of the slurry is adjusted. In some embodiments, the pH of the slurry is not adjusted. In some embodiments, the pH of the slurry is adjusted depending on the properties of the enzymes used. Thus, in some embodiments, the pH is adjusted, e.g., about 1 unit upwards, e.g., by adding NH3. In some embodiments, an alpha-amylase is added to the slurry. In some embodiments, the adjusting of pH is done at the time when alpha-amylase is added. In other embodiments, the pH is not adjusted and the alpha-amylase employed has a corresponding suitable pH-activity profile (e.g., activity at a pH about 4). In some embodiments, a corn flour is combined with a liquid and the enzyme to form the mash (e.g., slurry) by mixing the corn flour in a slurry mixer with hot liquid and alpha-amylase and a surfactant in a slurry tank. In some embodiments, only a portion of the enzyme (e.g. alpha-amylase) is added to the slurry tank, and the remaining enzyme is added later in the liquefaction tank. In some embodiments, only a portion of the surfactant is added to the slurry tank, and the remaining surfactant is added later in the liquefaction tank. In various embodiments, the step of combining corn flour with water and an enzyme and a surfactant to form the slurry is conducted at a temperature of from about 60 to about 88° C., for example 60° C., 65° C., 70° C., 75° C., 80° C., 85° C., 88° C., and a range between any two of these values.

In several embodiments, one or more surfactants are added to the slurry before, during, or immediately after the preliquefaction step. In some embodiments, during the preliquefaction step, the starch-containing material (front end mash) is held in the presence of a thermostable beta-glucanase and optionally other thinning enzymes, such as a xylanase, a cellulases, and/or a hemicellulase, at a temperature of 40 to 70° C., more preferably to 45 to 60° C., most preferably to 48 to 55° C., such as 50° C. The duration of the preliquefaction step is preferably 5 to 60 minutes, and more preferably 10 to 30 minutes, such as around 15 minutes. An alpha-amylase may be added before or during the preliquefaction step in some embodiments.

In several embodiments, one or more surfactants are added to the slurry before, during, or immediately after the gelatinization step. During the gelatinization step the starch is gelatinized. In some embodiments, gelatinization is achieved by heating the starch containing slurry to a temperature above the gelatinization temperature of the particular starch used. In some embodiments, gelatinization is by jet-cooking at appropriate conditions, such as, e.g. at a temperature between 95-140° C., (e.g., 85° C., 95° C., 105° C., 115° C., 125° C., 135° C., 140° C., and ranges in between any two of these values) to complete gelatinization of the starch. In some embodiments, gelatinization comprises non-pressure cooking. In some embodiments, gelatinization is performed in a plug flow continuous reactor. In some embodiments, gelatinization comprises jet cooking carried out at a temperature greater than 100° C. (Celsius meant?). In some embodiments, an alpha-amylase is added before or during the gelatinization step. In some embodiments, additional starch-degrading enzyme(s) is(are) added to the gelatinized mash together with the alpha-amylase. In some embodiments, during gelatinization (e.g. during jet cooking) the enzymes added in the preliquefaction step will be subjected to elevated temperatures and may be partly inactivated. Thus, in some embodiments, further starch-degrading enzymes may be added following the gelatinization step. In some embodiments, the gelatinization step is performed at a temperature of about 95-140° C. In some embodiments, the gelatinization step is performed at a temperature of about 105-125° C. In some embodiments, the gelatinization step is performed at a temperature of about 102° C. In some embodiments, the gelatinization step is performed for a period of about 1-15 minutes (e.g., 1, 2, 3, 4, 5, 6, 7, 8, 9, 10, 11, 12, 13, 14, 15, and ranges in between any two of these values). In some embodiments, the gelatinization step is performed for a period of about 3-10 minutes. In some embodiments, the liquefaction step is performed for a period of about 8 minutes.

In some embodiments, the methods provided herein include the addition of one or more acids (e.g. sulfuric acid, methanesulfonic acid, etc.,) to the slurry in an amount sufficient to adjust the pH to a range of from about 3 to about 6.5, alternatively from about 3 to about 5.5, alternatively from about 3.5 to about 5, alternatively from about 4 to about 5, alternatively about 4.5, alternatively from about 5.5 to about 6, alternatively about 5.8. In various embodiments, the acid is added to the slurry in an amount of from about 0.1 to about 1, alternatively from about 0.2 to about 0.8, alternatively from about 0.3 to about 0.6, alternatively from about 0.4 to about 0.5, parts by weight based on 100 parts by weight of the slurry. In some embodiments, addition of an acid to the slurry is conducted prior to and/or during any one of steps (a), (b), (c), (d), (e), and/or (f). However, in some embodiments of the methods provided herein, and acid is not added to the slurry prior to and/or during any one of steps (a), (b), (c). Advantageously, in some embodiments, the addition of one or more surfactants to the mash eliminates the need for addition of any pH adjusting chemicals. In some embodiments, the methods disclosed herein exclude a step where the slurry are not separated and reconstituted. In some embodiments, the methods disclosed herein do not comprise adding an acid (e.g., methanesulfonic acid, sulfuric acid, hydrochloric acid, acetic acid, tartaric acid, lactic acid, citric acid, an alkanesulfonic) to the slurry.

In some embodiments, during the liquefaction step the gelatinized starch (down stream mash) is broken down (hydrolyzed) into maltodextrins (dextrins). In several embodiments, one or more surfactants are added to the slurry before, during, or immediately after the liquefaction step. As used herein, the terms "liquefaction," "liquefy," "liquefact," and variations thereof shall be given its ordinary meaning and shall also refer to the process or product of converting starch to soluble dextrinized substrates (e.g., smaller polysaccharides). Liquefact can also be referred to as "slurry" or "mash." As used herein, the term "liquefaction tank" shall be given its ordinary meaning and shall also refer to a vessel, unit, or tank in which liquefaction is carried out. Liquefaction is a process in which starch is hydrolyzed, for example, by an enzymatic process to obtain oligosaccharides. In embodiments where the feedstock is corn, oligosaccharides are hydrolyzed from the corn starch content during liquefaction. As used herein, the term "secondary liquefaction" shall be given its ordinary meaning and shall also refer to a liquefaction process that takes place after an initial period of liquefaction or after a jet cooking step of a multi-stage liquefaction process. The secondary liquefaction can involve a different temperature than a previous liquefaction step or can involve the addition of additional starch-digesting enzymes (e.g., α-amylase) and/or surfactants. In some embodiments, liquefaction occurs in the slurry tank. In some embodiments, liquefaction occurs in the liquefaction tank. In some embodiments, liquefaction occurs in both the slurry and liquefaction tank. Depending on the embodiment, to achieve starch hydrolysis a suitable enzyme (e.g., an alpha-amylase) may be added. In some embodiments, other starch-degrading enzymes (e.g., beta-glucanase) are present and/or added to the slurry during liquefaction. In some embodiments, the liquefaction step is performed at a temperature between about 60-95° C., (e.g., 60° C., 65° C., 70° C., 75° C., 80° C., 85° C., 90° C., 95° C., and ranges in between any two of these values). In some embodiments, the liquefaction step is performed at a temperature between about 80-90° C. In some embodiments, the liquefaction step is performed at a temperature of about 90° C. In some embodiments, the liquefaction step is performed for a period of about 20-240 minutes (e.g., 20 min, 30 min, 50 min, 70 min, 90 min, 110 min, 130 min, 150 min, 170 min, 190 min, 210 min, 230 min, 240 min, and ranges in between any two of these values). In some embodiments, the liquefaction step is performed for a period of about 60-120 minutes. In some embodiments, the liquefaction step is performed for a period of about 90-150 minutes. In some embodiments, the liquefaction step is performed for a period of about 120 minutes. In some embodiments, the liquefaction is performed at a pH in the range of 3.5-7.0 (e.g., 3.5, 4.0, 4.5, 5.0, 5.5, 6.0, 6.5, 7.0 and ranges in between any two of these values). In some embodiments, the liquefaction is performed at a pH in the range of 4.0-6.5. In some embodiments, the liquefaction is performed at a pH in the range of 4.6-6.0. In some embodiments, the liquefaction is performed at a pH in the range of 4.8-5.1. In some embodiments, the liquefaction is performed at a pH in the range of 4.5-6.0. In some embodiments, the liquefaction is performed at a pH in the range of 4-5. In some embodiments, the pH of the slurry is adjusted. In some embodiments, the pH of the slurry is not adjusted. In some embodiments, the pH of the slurry is adjusted depending on the properties of the enzymes used. Thus, in some embodiments, the pH is adjusted, e.g. about 1 unit upwards, e.g. by adding NH3. In some embodiments, the adjusting of pH is done at the time when alpha-amylase is added. In other embodiments, the pH is not adjusted and the alpha-amylase employed has a corresponding suitable pH-activity profile (e.g., activity at a pH about 4).

In some embodiments of the methods disclosed herein, the starch liquefact is saccharified prior to fermentation. In some embodiments, saccharification includes the addition of one or more additional surfactants to the starch liquefact. As used herein, the terms "saccharification" and "saccharifying" shall be given its ordinary meaning and shall also refer to the process of converting polysaccharides to dextrose monomers using enzymes. Saccharification can specifically refer to the conversion of polysaccharides in a liquefact. Saccharification products are, for example, glucose and other small (low molecular weight) oligosaccharides such as disaccharides (a DP2) and trisaccharides (a DP3). As used herein, the term "degree of polymerization (DP)" refers to the number (n) of anhydroglucopyranose units in a given saccharide. Examples of DP1 saccharides are monosaccharides, such as glucose and fructose. Examples of DP2 saccharides are disaccharides, such as maltose and sucrose. A DP>3 saccharide has a degree of polymerization greater than 3. In some embodiments, the additional starch-digesting enzymes include glucoamylase. In some embodiments, the saccharification process can further include a heating step, wherein the starch liquefact comprising additional starch-digesting enzymes (i.e., the saccharification mixture) is heated to a temperature (e.g., a temperature that allows for optimal activity for the enzymes employed) for a period of time.

In some embodiments, the saccharification step and the fermentation step are performed as separate process steps while in other embodiments a simultaneous saccharification and fermentation (SSF) step is contemplated. In one such embodiment, a SSF process is employed where there is no holding stage for the saccharification, meaning that yeast and saccharification enzyme is added essentially together. In one embodiment, when doing SSF a pre-saccharification step at a temperature above 50° C. is introduced just prior to the fermentation. In some embodiments, the saccharification is carried out in the presence of a saccharifying enzyme, such as, for example, a glucoamylase, a beta-amylase, a beta-glucosidase or a maltogenic amylase. In still further embodiments, a phytase, and/or a protease are added. In some embodiments, one or more surfactants is added during saccharification, fermentation, and/or simultaneous saccharification and fermentation. The glucose produced from a complete simultaneous liquefaction and saccharification process can be recovered by any suitable approach. In addition to glucose, the heated mash can comprise additional materials, such as oil, protein and fiber by-products of the simultaneous liquefaction and saccharification process. These materials can also have economic value and can be recovered, as well. Depending on the embodiment, the saccharification and/or fermentation mixture includes one or more additional ingredients to increase the effectiveness of the process. For example, the mixture can include added nutrients (e.g., yeast micronutrients), antibiotics, salts, added enzymes, and the like. Nutrients can be derived from stillage or backset added to the liquid. Suitable salts can include zinc or magnesium salts, such as zinc sulfate, magnesium sulfate, and the like. Suitable added enzymes include those added to conventional processes, such as protease, phytase, cellulase, hemicellulase, exo- and endo-glucanase, xylanase, pullulanase and the like.

In some embodiments, prior to entering the fermentation tank, the slurry is cooled to about ambient temperature. In some such embodiments, the slurry is typically pumped through a heat exchanger to cool the slurry. It is important that the slurry remain in a relatively fluid form during this process. As the slurry thickens due to cooling, it places added pressure on the heat exchanger. A process improvement that avoids excessive thickening of the post-liquefaction slurry when cooled to ambient temperature is an advantage to the ethanol producer. Advantageous, in some embodiments, the methods disclosed herein reduce the viscosity of the post-liquefaction slurry (before and/or after cooling to ambient temperature), thereby reducing the pressure placed on the heat exchanger.

As used herein, the terms "fermentation" or "fermenting" shall be given its ordinary meaning and shall also refer to the process of transforming sugars from reduced plant material to produce alcohols (e.g., ethanol, methanol, butanol, propanol); organic acids (e.g., citric acid, acetic acid, itaconic acid, lactic acid, gluconic acid, propionate); ketones (e.g., acetone), amino acids (e.g., glutamic acid); gases (e.g., H2 and CO2), antibiotics (e.g., penicillin and tetracycline); enzymes; vitamins (e.g., riboflavin, B12, beta-carotene); and/or hormones. Fermentation can include fermentations used in the consumable alcohol industry (e.g., beer and wine), dairy industry (e.g., fermented dairy products), leather industry, and tobacco industry. Thus, fermentation includes alcohol fermentation. Fermentation also includes anaerobic fermentations. In some embodiments, fermenting comprises simultaneous saccharification and fermentation (SSF).

Depending on the embodiment, a variety of different fermenting organisms can be employed in a desired fermentation step. Non-limiting examples of suitable fermenting organisms include those that can convert DP1-3 sugars, especially glucose and maltose directly or indirectly to the desired fermentation product (e.g., ethanol, propanol, butanol or organic acid). In several embodiments, Fermenting can be effected by fungal organisms (e.g., yeast or filamentous fungi), including strains from a *Pichia* or *Saccharomyces* species. In some embodiments, the fermenting organism is *Saccharomyces cerevisiae*. In other embodiments, bacterial species are used in a fermentation step, such as, for example, species from *Acetobacter*, engineered *E. coli, Clostridium, Acidofilous* or *Lactobacter*. The yeast cells may be added in amounts of $10^5$ to $10^{12}$, preferably from $10^7$ to $10^{10}$, especially $5 \times 10^7$ viable yeast count per ml of fermentation broth. During the ethanol producing phase the yeast cell count should preferably be in the range from $10^7$ to $10^{10}$, especially around $2 \times 10^8$. In some embodiments, the temperature and pH during fermentation are the temperature and pH suitable for the microorganism in question. In some embodiments, the temperature and pH during fermentation is also configured with regard to the intended use of the fermentation product. For example, in some such embodiments, wherein the fermenting organism is yeast and the fermentation product for recovery is ethanol, the preferred temperature is in the range about 26-34° C., e.g. about 32° C., and at a pH e.g. in the range about pH 3-6, e.g. about pH 4-5.

In many embodiments, fermentation is conducted in the presence of a surfactant. In some embodiments, fermentation is conducted in the presence of the enzyme. For example, in some embodiments, fermentation is conducted in the presence of alpha amylase. The alpha amylase is added and/or is present during fermentation in an amount of from about 0.005 to about 0.1, alternatively from about 0.01 to about 0.05 wt %. In other embodiments, fermentation is conducted in the presence of glucoamylase. The glucoamylase is added and/or is present during fermentation in an amount of from about 0.01 to about 0.20, alternatively from about 0.03 to about 0.10, wt. % based on a total weight of the corn. As another example, in some embodiments, fermentation is conducted in the presence of acid protease. The acid protease is added and/or is present during fermentation in an amount of from about 0.001 to about 0.1, alternatively from about 0.002 to about 0.006, wt. % based on a total weight of the corn. At the end of fermentation, the product is called beer and typically includes greater than 12% by weight ethanol.

The method of the invention may further comprise recovering of the fermentation product, e.g. ethanol; hence the ethanol may be separated from the fermented material and purified. In some embodiments, the presently disclosed subject matter provides an end product such as, but not limited to, alcohol, lactic acid, an amino acid, fructose, citric acid, propanediol, dried distiller grain, dried distiller grain and solubles. In some embodiments, the product is an oil, a protein, or a fiber. These products can be primary or co-products (e.g., by-products) provided by the fermentation of a fermentable sugar. The product can also be any product that can be recovered from any stage of a liquefaction or simultaneous liquefaction and saccharification process. Thus, in one embodiment, the method of the invention comprises distillation to obtain the ethanol. The product of the fermentation process can be referred to herein as "beer". For example, fermenting corn produces "corn beer". Ethanol can be recovered from the fermentation mixture (i.e., from the beer) by any of a variety of known processes. For example, ethanol can be recovered by distillation. Thus, in some embodiments, the presently disclosed process further comprises an ethanol recovery step. This step can comprise distillation.

In some embodiments, the process also includes the step of distilling the beer to produce ethanol and whole stillage. In some embodiments, the step of distilling the beer is conducted at a temperature of from about 80 to about 130, alternatively of from about 90 to about 120, ° C. In some embodiments, the beer is distilled in a distillation system consisting of three columns. In some such embodiments, the beer is degassed in a degassing column (a first column). During degassing, carbon dioxide and other gases are removed from the beer. Next, ethanol and water are separated from non-converted solids in a separation column (a second column). The non-converted solids (whole stillage) fall to the bottom and are sent to the centrifuge for separation. The ethanol and water are separated in a rectifier column (a third column). In some embodiments, the presently disclosed methods produce a higher amount of ethanol than a conventional process. In some embodiments, the presently disclosed methods produce ethanol more quickly during fermentation than a conventional process. The yield of ethanol is typically at least 8%, at least 10%, at least 12%, at least 14%, at least 15%, at least 16%, at least 17%, at least 18% (v/v), and is some cases, at least 19%, at least 20%, at least 21%, at least 22%, and even at least 23% (v/v). The ethanol obtained may be used as, for example, fuel ethanol, drinking ethanol, i.e., potable neutral spirits, or industrial ethanol.

In some embodiments, the aqueous by-product (whole stillage) from the distillation process is separated (e.g., for by centrifugation) into two fractions: wet grain (solid phase) and thin stillage (supernatant). In some embodiments, the wet grain is dried, such for example, in a drum dryer. The dried product is referred to as "Distillers Dried Grain", and in some embodiments be used as animal feed. In some embodiments, thin still fraction may be evaporated to produce a syrup fraction, mainly consisting of limit dextrins and non-fermentable sugars. In some embodiments, may further comprise step of extracting corn oil from the syrup. Some embodiments of the methods disclosed herein further contemplate introducing the syrup fraction into a dryer together with the wet grain to provide a product referred to as "Distillers Dried Grain with Solubles" (DDGS). DDG and DDGS are economically important co-products of corn-to-ethanol production and are primarily used as animal feed. Recognized value attributes of dried distiller grain and solubles are: consistency, physical characteristics (e.g. flowability, color, odor), and composition (e.g. protein and fiber content). The quality of DDG and DDGS are negatively impacted by prolonged process time and elevated temperature. Maillard reaction products are formed during high temperature process steps in corn-to-ethanol productions. The presence of Maillard reaction products negatively impacts the quality of dried distiller grain and dried distiller grain and solubles. The presently disclosed processes can result in reduced process time, reduced process temperature, or both. In some embodiments, providing a surfactant during one or more of steps (a), (b), (c), (d), (e), and/or (f) enhances one or more of the consistency, physical characteristics (e.g. flowability, color, odor), and/or composition (e.g. protein and fiber content) of the dried distiller grain and dried distiller grain and solubles. While not being bound by any particular theory, in some embodiments, the reduction in slurry viscosity effected by the added surfactants reduces process time and/or process temperature. Further, in some embodiments, the methods provided herein result in higher protein content in the final dried distiller grain and solubles product. While not being bound by any particular theory, in some embodiments, the reduction in slurry viscosity effected by the added surfactants result in more complete digestion of starch, resulting in higher protein content of the end product.

Slurry Viscosity Reduction

When an aqueous starch slurry is heated, the granules swell and eventually burst, dispersing the starch molecules into the solution. During this "gelatinization" process there is a dramatic increase in viscosity. As the solids level is 30-40% in a typical industrial process, the starch has to be thinned or "liquefied" so that it can be suitably processed. This reduction in viscosity is primarily attained by enzymatic degradation in current commercial practice. Typically alpha amylase is added to minimize the initial rise in the slurry viscosity (i.e., peak viscosity) as well as the viscosity of the final hot slurry produced (i.e., final viscosity). Controlling both of these viscosity values is important in the corn cook process (gelatinization and pasting) for pumpability in the process pipes, slurry mixer as well as the steam pressured jet cooker. Thus, there is a need in the field to develop processes that reduce viscosity during liquefaction of corn starch (and other starches as well). During liquefaction processes, the viscosity of the starch slurry is frequently used as a measure of the conversion of the starch into smaller DP units. Sometimes herein the expression "initial viscosity" is used, which is intended is not literally the initial viscosity, but rather the peak viscosity which occurs for example at around the point of gelatinization of the substrate. Initial viscosity is used to distinguish from the "final viscosity" which is the viscosity of a substrate, e.g., starch slurry, at the conclusion of a liquefaction process. As used herein, the term "comparable liquefaction process" shall be given its ordinary meaning and shall also refer to a controlled process for liquefaction. The liquefaction processes are conducted under controlled conditions, e.g. the liquefaction process comprises specified conditions of temperature, pH, calcium ion concentration, and substrate concentration. Comparable liquefaction processes provide a means to compare different surfactants or surfactants blends in their ability to liquefy a starch by controlling for as much as possible except the differences in surfactants. As used herein, the term "facilitating liquefaction" or "facilitating a liquefaction process" shall be given its ordinary meaning and shall also refer to any degree of improvement in liquefaction of a starch slurry, such as making a liquefaction process more efficient, more effective, more economical, or easier (facile). The term includes reducing the number or amount of enzymes required, reducing the peak or final viscosity of the starch slurry, increasing the rate or extent of starch degradation, or the production of fragments of any particular DP, or of limit dextrins. Facilitating liquefaction also includes reducing the net energy requirements, improving the utilization of substrate, or improving other conditions such as the calcium ion concentration or tolerance of changes in calcium ion, ability to use different starch (i.e., substrate) sources, types, or concentrations, ability to operate at preferred pH levels or ranges, quantity and quality of the resultant product, and the like.

In some embodiments, the viscosity of the slurry tank is less than about 4000 cP, 3500 cP, 3000 cP, 2500 cP, 2000 cP, 1500 cP, 1000 cP, 500 cP, 400 cP, 300 cP, 200 cP, 100 cP, 50 cP, 40 cP, 30 cP, 20 cP, or 10 cP before, during, and/or after one or more of steps (a), (b), (c) and/or (d). In some embodiments, the viscosity of the liquefaction tank is less than about 4000 cP, 3500 cP, 3000 cP, 2500 cP, 2000 cP, 1500 cP, 1000 cP, 500 cP, 400 cP, 300 cP, 200 cP, 100 cP, 50 cP, 40 cP, 30 cP, 20 cP, or 10 cP before, during, and/or after one or more of steps (a), (b), (c) and/or (d). In some embodiments of the methods provided herein, the peak viscosity of the slurry tank and/or liquefaction tank is reduced by at least 5% (e.g., 5%, 10%, 15%, 20%, 25%, 30%, 40%, 50%, 60%, 70%, 80%, 90%, 100%, and overlapping ranges) compared to a slurry not treated with the one or more surfactants. In some embodiments of the methods provided herein, the final viscosity of the slurry tank and/or liquefaction tank is reduced by at least 5% (e.g., 5%, 10%, 15%, 20%, 25%, 30%, 40%, 50%, 60%, 70%, 80%, 90%, 100%, and overlapping ranges) compared to a slurry not treated with the one or more surfactants. Slurry viscosity can be measured by various means know to those of skill in the art. In one embodiment, the viscosity is measured in a viscometer which comprises a water jacketed sample vessel, and a rotational member for insertion into the sample vessel (Viscoklick. IKA Eurostar Labortechnik power control-vise p7 with a Viscokliick VK1 controller (Werke GMBH & Co, Germany) analyzed on a personal computer with Labworldsoft version 2.6. In some embodiments, the viscosity of the slurry in the slurry and/or liquefaction tanks is measured by the funnel test. In some embodiments, the viscosity of the slurry in the slurry and/or liquefaction tanks is measured with a RVA4 Viscometer. In several embodiments, providing a surfactant to the slurry allows for various advantageous adjustments to the starch processing, including, but not limited to, increasing the percentage of solids used to create the mash, removing the addition of pH adjusting chemicals to the mash, decreasing the liquefaction time, and/or removing the use of a jet cooker.

After being subjected to a process of the invention at least 85%, at least 86%, at least 87%, at least 88%, at least 89%, at least 90%, at least 91%, at least 92%, at least 93%, at least 94%, at least 95%, at least 96%, at least 97%, at least 98%, or preferably at least 99% of the dry solids in the starch-containing material are converted into a soluble starch hydrolyzate. As used herein, the term "residual starch" refers to the remaining starch (soluble or insoluble) in a starch composition after fermentation. In some embodiments, the amount of residual starch is reduced by at least about 5% (e.g., 5%, 10%, 15%, 20%, 25%, 30%, 40%, 50%, 60%, 70%, 80%, 90%, 100%, and overlapping ranges) as compared to a comparable method performed in the absence of said one or more surfactants in the slurry. While not being bound by any particular theory, in some embodiments, the surfactant provided herein prevents the starch from forming hydrogen bonds that cause starch agglomeration, thereby allowing enzymes to access their substrate. The more the viscosity is reduced, the further the starch is liquefied, the greater the production of dextrins (or the higher the DE of the resultant liquefied starch). Thus in one embodiment, the peak viscosity is reduced by at least 10, 20, 25, 30, 40, or even 50% or more relative to the peak viscosity of a comparable slurry not treated with a surfactant.

The viscosity of the slurry throughout the ethanol production process is a critical component of ethanol production. The continuous flow process for ethanol production requires that the slurry be low enough in viscosity to move through pumps and pipes at a continuous rate. A slurry that gets too viscous can plug pipes, overflow tanks and cause undue stress on pumping equipment. In addition, a slurry that is not viscous enough can also cause problems as the solids in the slurry can fall out of the slurry and build up in pipes and pumps which also can cause plugging problems or undue stress on equipment. Providing surfactant to the slurry results in a slurry with a lower viscosity than typically observed when using a thinning enzyme alone. In some embodiments, the lowered viscosity of the slurry is observed through-out the ethanol production process, e.g. starting with the viscosity of the mash as it is formed by mixing the meal with liquid, the viscosity of the mash as it enters the slurry tank, viscosity of the effluent from the slurry tank, viscosity after liquefaction is considered complete and/or viscosity after the effluent from liquefaction is cooled prior to entering the fermentation process. In some embodiments, the reduced viscosity results in increased flow rates of the liquefied mash, thereby increasing the capacity of the production plants, especially by improving heat transfer and facilitating passage of the liquefied mash through the mash coolers. Thus, in some embodiments, the methods disclosed herein facilitates the use of higher dry matter percentage in the fermentation while still securing an efficient cooling and a correct and uniform temperature of the mash delivered to the fermentation tanks. In some embodiments, the reduction in the peak viscosity of the slurry tank and/or liquefaction tank results less energy spent for mixing. In some embodiments, a lower average viscosity improves the mixing of the mash/starch in the slurry tank and/or liquefaction tank and its pumping through the liquefaction process. In some embodiments, the methods provided herein save considerable time, effort, and costs associated with heating, cooling and transferring the slurry between tanks.

In some embodiments, due to the reduction in slurry viscosity, the amount of alpha amylase that will be used in a starch hydrolysis process can be decreased. For example under the same conditions the dose of alpha amylase that may be needed at the same pH (e.g. about pH 5.5 to about 6.0) to obtain the same level of viscosity may be about 20%, 30%, 40%, 50%, or 60% less when the alpha amylase is combined with a surfactant of the invention. Generally, liquefaction takes place at temperatures that are too high to allow for optimal activity of all the enzymes needed to fully reduce starch to fermentable sugars, such as glucose. While not being bound by any particular theory, in some embodiments, the surfactants provided herein allow the enzymes to be held in a more active form. In some embodiments, the methods provided herein effectively eliminate the need for a second addition of alpha-amylase, which is typically performed after the jet cooker. In some embodiments, providing a surfactant to the slurry avoids the need for a secondary liquefaction to be performed.

Advantageously, in some embodiments, the methods provided herein allow the mash to have a pH that is the natural pH of the slurry (i.e., the pH of the mixture of starch-containing plant material, water, and/or backset). Thus, in some embodiments, this mash can be used without the addition of any pH adjusting chemicals. In some embodiments, the methods provided herein allow the starch processing to be performed without adjusting the pH of the starch-containing slurry and can be done at relatively low temperatures compared with the liquefaction temperatures of conventional processes. Fermentable sugar can be lost during high temperature, long hold times, and the use of only mildly acidic pH conditions. These losses can be attributed, at least in part, to Maillard reactions between a reducing end on the carbohydrate and an amino compound (e.g., ammonia or a protein). The Maillard reactions are known to be temperature, pH, and time dependent. Thus, reducing pH from the 5.8 typical for liquefaction to a lower pH (e.g., between 5.2 and 3.8) should decrease the amount of Maillard reaction products. Decreasing the time the slurry is held at high temperature should also decrease undesired degradation reactions. In particular, if the jet cooking step is not employed, a greater yield of fermentable sugars after liquefaction is expected. Coupled with the action pattern of the corn-expressed enzyme, these factors can lead to a substantially higher yield of ethanol from the presently disclosed process. In some embodiments, the invention comprises a method for increasing the yield and/or rate of ethanol production from corn or similar grain, comprising: liquifying the corn-like grain slurry at a pH of about 4.0 to about 7.0 at a temperature in the range from about 25° C. to about 65° C. using: an alpha amylase and a surfactant; saccharifying and fermenting the slurry using enzymes, including a glucoamylase and a fermenting organism to produce ethanol, wherein the yield and/or rate of ethanol production is greater than the rate observed without the addition of surfactant. In some embodiments of the methods provided herein, the fermentation rate is increased by at least 5% (e.g., 5%, 10%, 15%, 20%, 25%, 30%, 40%, 50%, 60%, 70%, 80%, 90%, 100%, and overlapping ranges) compared to a slurry not treated with the one or more surfactants.

While not being bound by any particular theory, in some embodiments, the surfactants provided herein maintain the corn oil in a liquid phase and prevent solids from fermentation from associating with and sequestering the oil. In some embodiments, the corn oil yield is increased by at least about 5% (e.g., 5%, 10%, 15%, 20%, 25%, 30%, 40%, 50%, 60%, 70%, 80%, 90%, 100%, and overlapping ranges) as compared to a comparable method performed in the absence of said one or more surfactants in the slurry.

Surfactants

Many embodiments of this invention relate to use of surfactants that decrease the viscosity of the slurry in the liquefaction and/or slurry tanks. In many embodiments, there are provided methods of starch processing, comprising the addition of one or more surfactants. As described herein, embodiments of the methods include addition of one or more surfactants to the mash, slurry, or liquefact at any point in the process stream. In some embodiments, the surfactant is added to the liquefaction tank. In some embodiments, the surfactant is added to the slurry tank. In some embodiments, the surfactant is added to both the slurry tank and to the liquefaction tank. In some embodiments, the surfactant is added to the slurry tank and retains some or all of its activity in the liquefaction tank.

In several embodiments, said one or more surfactants comprises a nonionic surfactants, anionic surfactants (e.g., alkyl sulfates, alkyl ether sulfates, alkylphenol ether sulfates, phosphate esters), and/or amphoteric surfactants (e.g., cocamidopropyl betaine, cocamidopropylamine oxide), or any combination thereof. Nonionic surfactants include, but are not limited to, alcohol alkoxylates, alkylphenol ethoxylates, block copolymers of EO/PO, block copolymers of ethylene diamine, alkyl polyglycosides, glycerol esters, polyethylene glycol esters (e.g., monoesters, diesters, esters derived from a fatty acid, and/or esters derived from carboxylic acid), functionalized polyols (e.g., those based on sorbitol, sorbitan, and/or isosorbide), sorbitan esters (e.g., monoesters, diesters, triesters, esters derived from fatty acids, esters derived from carboxylic acids), ethoxylated sorbitan esters, alkoxylated sorbitan esters, natural oil alkoxylates, and/or polyoxyalkylene glycols. It is to be appreciated that other types of surfactants can also be used. The alcohol alkoxylate can, in some embodiments, comprise or be derived from alcohol ethoxylates, alcohol ethoxylates/propoxylates, and/or alkyl capped alcohol alkoxylates (e.g. methyl capped alcohol alkoxylates). Non-limiting examples of block copolymers of EO/PO are internal EO(x) block/external PO(y) block copolymers and internal PO(y) block/external EO(x) block copolymers. Additionally, various types of block copolymers of ethylene diamine are employed depending on the embodiment, such as, for example, internal EO(x) block/external PO(y) block copolymers and internal PO(y) block/external EO(x) block copolymers. Non-limiting examples of glycerol ester that may be employed too as surfactants include, but are not limited to, polyglycerol fatty acid esters, monoglycerol fatty acid esters (mono glycerides), diglycerides, alkoxylated monoglycerides (e.g., ethoxylated monoglycerides, ethoxylated and propoxylated monoglycerides), and/or alkoxylated diglycerides (e.g., ethoxylated diglycerides, ethoxylated and propoxylated diglycerides). Depending on the embodiment, a variety of different ethoxylated sorbitan esters can be used as surfactants, such as, for example, ethoxylates of monoesters, ethoxylates of diesters, ethoxylates of triesters, esters derived from fatty acids, esters derived from carboxylic acids, or any combination thereof. Non-limiting examples of alkoxylated sorbitan esters that may be employed as surfactants include, but are not limited to, propoxylates of monoesters, propoxylates of diesters, propoxylates of triesters, esters derived from fatty acids, and esters derived from carboxylic acids. Non-limiting examples of natural oil alkoxylates can include, in some embodiments, castor oil ethoxylates, castor oil alkoxylates, soybean oil alkoxylates (alkoxylates of mono- and di-glycerides), soybean oil ethoxylates (ethoxylates of mono- and di-glycerides), natural oil (fat) alkoxylates (alkoxylates of mono- and di-glycerides), and/or natural oil (fat) ethoxylates (ethoxylates of mono- and di-glycerides). In some embodiments, the polyoxyalkylene glycol surfactant comprises or is derived from polyethylene glycol, methoxypolyethylene glycol, polypropylene glycol, and/or polyoxyalkylene glycols (EO/PO random copolymer). Non-limiting examples of suitable non-ionic surfactants, for purposes of the present disclosure, are commercially available from BASF Corporation, under the trade names of PLUIRAFAC®, PLURONIC®, TETRONIC®, LUTROPUR®, and LUTENSOL®.

In some embodiments, the surfactant comprises or is derived from a surfactant that is GRAS (generally recognized as safe). In several embodiments, the surfactant has an HLB that is greater than 2 (e.g., 2, 3, 4, 5, 6, 7, 8, 9, 10, 11, 12, 13, 14, 15, 16, 17, 18, 19, 20, 25, 30, or higher and overlapping ranges therein). In some embodiments, the surfactant has an HLB value of greater than about 10. In some embodiments, the surfactant has an HLB value of greater than about 15.

Non-ionic surfactants, suitable for purposes of the present disclosure, include alcohol alkoxylates. Suitable alcohol alkoxylates include linear alcohol ethoxylates. Additional alcohol alkoxylates include alkylphenol ethoxylates, branched alcohol ethoxylates, secondary alcohol ethoxylates, castor oil ethoxylates, alkylamine ethoxylates (also known as alkoxylated alkyl amines), tallow amine ethoxylates, fatty acid ethoxylates, sorbital oleate ethoxylates, end-capped ethoxylates, or combinations thereof. Further non-ionic surfactants include amides such as fatty alkanolamides, alkyldiethanolamides, coconut diethanol amide, lauramide diethanol amide, cocoamide diethanol amide, polyethylene glycol cocoamide, oleic diethanol amide, or combinations thereof. Yet further non-ionic surfactants include polyalkoxylated aliphatic base, polyalkoxylated amide, glycol esters, glycerol esters, amine oxides, phosphate esters, alcohol phosphate, fatty triglycerides, fatty triglyceride esters, alkyl ether phosphate, alkyl esters, alkyl phenol ethoxylate phosphate esters, alkyl polysaccharides, block copolymers, alkyl polyglycocides, or combinations thereof.

Non-ionic surfactants, also suitable for purposes of the present disclosure, include polyalkylene oxide surfactants (also known as polyoxyalkylene surfactants or polyalkylene glycol surfactants). One such example of a suitable surfactant is described as a natural oil polyol herein. Suitable polyalkylene oxide surfactants include polyoxypropylene surfactants and polyoxyethylene glycol surfactants. Suitable surfactants of this type are synthetic organic polyoxypropylene (PO)-polyoxyethylene (EO) block and random copolymers. These surfactants generally comprise a di-block polymer comprising an EO block and a PO block, a center block of polyoxypropylene units (PO), and having blocks of polyoxyethylene grafted onto the polyoxypropylene unit or a center block of EO with attached PO blocks. Further, this surfactant can have further blocks of either polyoxyethylene or polyoxypropylene in the molecules. The surfactant may also include butylene oxide (BO) blocks, and can include random incorporations of two or three alkylene oxides, e.g. EO/PO/BO, EO/PO/PO, EO/EO/PO, etc. Such surfactants may be referred to in the art as "heteric" block surfactants. Suitable surfactants of this type also include random EO, PO, and/or BO co- and ter-polymers. In some embodiments, the surfactant comprises a block copolymer based on ethylene oxide (EO) and propylene oxide (PO) selected from the group comprising L 92, Pluronic L 62 LF, Pluronic N 3, Pluronic F 38 Pastille, Pluronic F 108 Cast Solid Surfacta, Pluronic L 35, Pluronic F 108 Pastille, Pluronic F 127, Pluronic F 87, Pluronic P 105, Pluronic L 10, Pluronic F 68 LF Pastille, Pluronic P 84, Pluronic P 103, Pluronic P 104, Pluronic F 88, Pluronic P 123 Surfactant, Pluronic 31R1, Pluronic F 68 Pastille, Pluronic P 65, Pluronic F 77, Pluronic F 127 NF Prill Poloxamer 407, Pluronic FT L 61, Pluronic 25R4, or Pluronic L61. In some embodiments, the surfactant is Pluronic P 104. In some embodiments, the surfactant comprises tetra-functional block copolymers based on ethylene oxide and propylene oxide including, but not limited to, Tetronic 1304, Tetronic 1307, and Tetronic 1107, Tetronic 704, Tetronic 709, Tetronic 1104, Tetronic 1304, Tetronic 702, Tetronic 1102, Tetronic 1302, Tetronic 701, Tetronic 901, Tetronic 1101, and Tetronic 1301. In some embodiments, the surfactant comprises Tetronic 1304.

In some embodiments, the surfactant comprises castor oil derivatives ethoxylated with 30 to 40 ethylene oxide units (EO), hydrogenated castor oil derivatives ethoxylated with 7 to 60 EO, ethoxylated derivatives of coconut oil, soybean lecithin, C6 to C22 fatty alcohols polyethoxylated with 8 to 30 EO, polyethoxylated alkylphenols, ethoxylated arylphenols, polyglycol tridecyl alcohol ethers, block polyethers of di- and triblock type, sorbitol derivatives comprising 1 to 3 polyoxyethylene chains and 1 to 3 C12 to C30 fatty chains, C8 to C36 fatty acid esters ethoxylated with 8 to 30 EO, mono- and diglyceride esters of C8 to C36 fatty acids, C8 to C22 fatty amines, or any combination thereof.

In some embodiments, the surfactant comprises polyalkyleneoxides, alkylpolyalkyleneoxides, polyoxyethylene sorbitan monolaurates, alkylpolyglycosides, anionic derivatives of alkylpolyglycosides, fatty alcohols, anionic derivatives of fatty alcohols, phosphate esters, ethoxylated nonylphenols, ethoxylated octylphenols, copolymers of aldehydes and octylphenolpoly(oxyethylene), ethoxylated glycerol-partial fatty acid esters, ethoxylated hydrogenated castor oil, poly(oxyethylene)-hydroxystearate, and poly(oxypropylene)-poly(oxyethylene)-block polymers with a molar mass of <20,000.

In some embodiments, the surfactant comprises a condensation product of one mole of saturated or unsaturated, straight or branched chain carboxylic acid having from about 8 to about 18 carbon atoms with from about 6 to about 50 moles of ethylene oxide; non-limiting examples of such surfactants include, but are not limited to, Disponil NG 1080, Disponil AES 48, Disponil AFX 4070, Disponil FES 32 IS, Disponil OCS 27, Disponil OC 25, Disponil FES 77 IS, Disponil ALS 33, Disponil A 4065, Disponil A 1080, Disponil LDBS 20, Disponil FES 430, Disponil SOS 842, Disponil SDS G, Disponil AES 25, Disponil SLS 2010 Preserved, Disponil SUS 87 Spez., Disponil STO 100, Disponil OC 5, Disponil AFX 4030 US, Disponil AFX 5060, Disponil LDBS 25, Disponil AFX 3070, Disponil FES 27, Disponil SLS 101 Special, Disponil FES 27 A/CALFOAM ES-303, Disponil LS 500, Disponil ODSLS, Disponil BES 20, Disponil SDS 15, Disponil AFX 1080, Disponil LDBS 55, Disponil AFX 2075, Disponil A 3065, Disponil OSS 50 KS, Disponil PGE 110, Disponil AFX 4030, Disponil A 1580, Disponil AFX 9580, Disponil AES 60, Disponil AES 72, Disponil FES 32, Disponil PLS 127, Disponil FES 61, Disponil FES 77, Disponil FES 993, Agnique FOH 898, Agnique AMD 10, Agnique FOH 90C, Agnique AMD 810, Agnique ME 890, Agnique AE 3-2EH, Agnique SBO 10, Agnique SLES-227, Agnique RSO-60, Agnique GPC, Agnique MBL 530 B, Agnique ME 18 RD-F, Agnique PG 8105-G, Agnique CSO-40, Agnique PG 8107-G, Agnique OAS 50 K, Agnique AMD 12, Agnique FOH 90C-3, Agnique MBL 510 H, Agnique ME 181, Agnique SPO 40, Agnique SLES-370, Agnique MBL 520 L, Agnique SLS 90 P, Agnique ESO 81-G, Agnique ME 18 SD-F, Agnique CSO-20, Agnique CSO-35, Agnique PG 9116, Agnique ABS 60 C-EH, Agnique ABS 70 C, Agnique AE 3-2EH, Agnique AMD 10, Agnique AMD 12, Agnique AMD 3 L, Agnique AMD 810, Agnique ANS 3DNP-U, Agnique ANS 3DNPW, Agnique ANS 4DNL, Agnique ANS 4DNP Sulfonate, Agnique BL 2101, Agnique BL 2161, Agnique BL 2244 Blend, Agnique BL 2437, Agnique BL 2707, Agnique BL 2904, Agnique BL 2972, Agnique BL 4524, Agnique BL 4886, Agnique BL 5150, Agnique BL 6816-U, Agnique BL 9753, Agnique BL 9754, Agnique BP NP 1530, Agnique BP NP-4030 BO-PO Poly, Agnique CP 72 L, Agnique CSO 40-U, Agnique CSO-20, Agnique CSO-25, Agnique CSO-30, Agnique CSO-35, Agnique CSO-35, Agnique CSO-36 Ethox Castor Oil, Agnique CSO-36D, Agnique CSO-40, Agnique DDL Dispersant, Agnique DFM 111 S, Agnique ESO 81-G, Agnique FOH 898, Agnique FOH 90C, Agnique FOH 90C-3, Agnique FOH 90C-5, Agnique GPC, Agnique KE 3658, Agnique MBL 150 H, Agnique MBL 510 H, Agnique MBL 520 L, Agnique MBL 530 B, Agnique MBL 530B-F, Agnique ME 1218, Agnique ME 18 RD-F, Agnique ME 18 SD-F, Agnique ME 181, Agnique ME 181 SP, Agnique ME 181-U Methyl Olea, Agnique ME 18R-U, Agnique ME 18S-U Methyl Soyate, Agnique ME 18SD-U Dist Methyl S, Agnique ME 610 U, Agnique ME 890, Agnique NSC 11NL Sulfonate, Agnique NSC 11NP Sulfonate, Agnique NSC 2NP-U Sulfonate, Agnique NSC 3NP, Agnique NSC 4AL Sulfonate, Agnique OPMB 11 Ethox Octylphen, Agnique PE NP-9 Phosphate Ester, Agnique PG 264, Agnique PG 8105, Agnique PG 8105-G, Agnique PG 8107-G, Agnique PG 8107-U Alkylpolygly, Agnique RSO-60, Agnique SBO 10, Agnique SBO 30, Agnique SBO-60, Agnique SLES-227, Agnique SLES-270 Sodium Lauryl, Agnique SLES-370, Agnique SLS 90 P, Agnique SMO-20-U (6900), Agnique SOAP L, Agnique SPO 40, Agnique ST 2434, and Agnique TDA-12. In some embodiments, the surfactant comprises Agnique SBO 30. In some embodiments, the surfactant comprises Agnique CSO-30.

In some embodiments, the surfactant comprises a condensation product of one mole of a saturated or unsaturated, straight or branched chain alcohol having from about 6 to about 24 carbon atoms with from about 3 to about 50 moles of ethylene oxide. Some such embodiments include polyalkoxylated saturated aliphatic alcohols, polyalkoxylated unsaturated aliphatic alcohols, polyethoxylated saturated aliphatic alcohols, polyethoxylated unsaturated and aliphatic alcohols. Non-limiting examples of such surfactants include, but are not limited to, Lutensol A 3 N, Lutensol XL 140, Lutensol XL 70, Lutensol XP 90, Lutensol LA 60, Lutensol OP 10, Lutensol OP 40 70%, Lutensol TDA 9, Lutensol AO 8, Lutensol TDA 6, Lutensol TDA 8 90%, Lutensol TDA 10, Lutensol XP 30, Lutensol XL 79, Lutensol XP 50, Lutensol XP 70, Lutensol XP 89, Lutensol XP 80, Lutensol XP 40, Lutensol A 12 N, Lutensol A 9 N, Lutensol XL 80, Lutensol XL 90, Lutensol XL 100, Lutensol XP 79, Lutensol TDA 3, Lutensol AO 3, and Lutensol A65N. In several embodiments, the surfactant comprises Lutensol XP 90 and Lutensol AO 8. In some embodiments, the one or more surfactants further comprises one or more of Lutensol A65N, Lutensol A03, Pluronic L61, Tetronic 1304, and Agnique SBO.

In some embodiments, the surfactant is added at more than one discrete step in the process. In some embodiments, the same surfactant is added at two or more discrete steps in the process. In other embodiments, the different surfactants are added at two or more discrete steps in the process. In some embodiments, the surfactants comprise a blend of 2, 3, 4, 5, 6, 8, 9, or more different surfactants. In some embodiments, the surfactants of a surfactant blend work synergistically together to reduce slurry viscosity.

In some embodiments of the methods provided herein, a surfactant blend is added to a starch slurry, the blend comprising: at least a first and a second surfactant, the first surfactant having a surface activity that, when used in a liquefaction process, results in a final viscosity lower than, but a peak viscosity higher than, a corresponding surface activity of the second surfactant, when each surfactant is used alone in comparable liquefaction processes, wherein when used in comparable liquefaction processes, the surfactant blend provides surface activity that results in a final viscosity about the same as that resulting from the use of the first surfactant alone, and a peak viscosity substantially less than that resulting from the use of the second surfactant alone; wherein comparable liquefaction processes comprise specified conditions of temperature, pH, calcium ion concentration, and substrate concentration.

In some embodiments of the methods provided herein comprising making a slurry comprising the starch, heating the slurry to an acceptable temperature for liquefaction, adding a surfactant blend comprising said first and second surfactants to the slurry, and incubating the slurry with the surfactant blend for a time and at a temperature sufficient to liquefy the starch slurry. In some embodiments, the final viscosity is about as low as that resultant from the use of the first surfactant alone in a comparable liquefaction process, and the peak viscosity is lower than that resultant from the use of the second surfactant alone in a comparable liquefaction process. In some embodiments, the amount of surfactant blend added results in the addition of less of each of the first and second surfactants than the corresponding amounts of the first and second surfactants, respectively, added when each is used alone in a comparable liquefaction process. In some embodiments, the amount of each of the first and second surfactants, respectively, is about half the corresponding amount added when each is used alone.

As disclosed herein, the use of particular types, ratios, and/or amounts of surfactants in a surfactant blend can result in synergistic effects in reducing viscosity. These synergistic effects can be such that the one or more effects of the surfactant blend are greater than the one or more effects of each surfactant alone at a comparable dosing level, or they can be greater than the predicted sum of the effects of all of the surfactants at a comparable dosing level, assuming that each surfactant acts independently. The synergistic effect can be about, or greater than about, 5, 10, 20, 30, 50, 75, 100, 110, 120, 150, 200, 250, 350, or 500% better than the effect of treating a slurry with one of the surfactants alone, or the additive effects of each of the surfactants when administered individually. The effect can be any of the measurable effects described herein. The surfactant blend comprising a plurality of surfactants can be such that the synergistic effect is a decrease in viscosity and that viscosity is decreased to a greater degree as compared to the sum of the effects of administering each component, determined as if each component exerted its effect independently, also referred to as the predicted additive effect herein. For example, if a blend comprising surfactant (a) yields an effect of a 20% improvement in viscosity, and a composition comprising surfactant (b) yields an effect of 50% improvement in viscosity, then a blend comprising both surfactant (a) and surfactant (b) would have a synergistic effect if the surfactant blend's effect on viscosity was greater than 70%.

A synergistic blend of surfactants can have an effect that is greater than the predicted additive effect of administering each surfactant of the surfactant blend alone as if each surfactant exerted its effect independently. For example, if the predicted additive effect is 70%, an actual effect of 140% is 70% greater than the predicted additive effect or is 1 fold greater than the predicted additive effect. The synergistic effect can be at least about 20, 50, 75, 90, 100, 150, 200 or 300% greater than the predicted additive effect. In some embodiments, the synergistic effect can be at least about 0.2, 0.5, 0.9, 1.1, 1.5, 1.7, 2, or 3 fold greater than the predicted additive effect.

In some embodiments, the synergistic effect of the combination compositions can also allow for reduced amounts of surfactants added during the process, leading to cost savings. Furthermore, the synergistic effect can allow for results that are not achievable through the use of other surfactant combinations. Therefore, proper identification, specification, and use of combinations of surfactants can allow for significant improvements in the reduction of slurry viscosity. The surfactants described herein may be also combined with other modalities to achieve synergic effects. These other modalities include, but are not limited to, additional enzymes, pH modifiers, and others.

Starch-Degrading Enzymes

In some embodiments, the methods disclosed herein comprise the addition of one or more starch-degrading enzymes at one or more of the steps the process. As used herein, term "starch-digesting enzyme" shall be given its ordinary meaning and shall also refer to any enzyme that can catalyze the transformation of a starch molecule or a degradation product of a starch molecule. In several embodiments, the one or more enzymes are added the process stream (e.g. the mash, the slurry, or the liquefact) in an amount ranging from about 0.001% to about 0.2 wt % (e.g., 0.001%, 0.005%, 0.01%, 0.03%, 0.05%, 0.07%, 0.09%, 0.1%, 0.11%, 0.13%, 0.15%, 0.17%, 0.19%, 0.2% and ranges in between) based on a total weight of the starch-containing material. Depending on the embodiment, a variety of different enzyme can be selected, such as, for example, a phytase, a cellulase, a protease, an aminopeptidase, an amylase, a beta-amylase, a carbohydrase, a carboxypeptidase, a catalase, a chitinase, a cutinase, a cyclodextrin glucanotransferase, a deoxyribonuclease, an esterase, an α-galactosidase, a β-galactosidase, a glucoamylase, α-glucosidase, a β-glucosidase, a haloperoxidase, an invertase, isomerase, a laccase, a lipase, a mannosidase, an oxidase, a pectinase, a peptidoglutaminase, a peroxidase, a polyphenoloxidase, a nuclease, a ribonuclease, a transglutaminase, a xylanase, a pullulanase, an isoamylase, a carrageenase, and a protease. Non-limiting examples of commercially available enzymes that may be employed with the methods disclosed herein include, but are not limited to, those sold under the following trade names: SZM™ XC-150, DELTAZYM® APS acid protease, FERMGEN®, FERMGEN® 2.5X, SZM™ AP-1, FUELZYME®, AVANTEC®, AVANTEC® Amp, LIQUOZYME® SCDS, LIQUOZYME®LpH, SPEZYME® RSL, SPEZYME® CL, SPEZYME CL WB, SPEZYME® Alpha, SPEZYME® Alpha PF, SZM XT-20, STARGEN® 002, STARGEN® 002 WB, OPTFMASH™ TBG, OPTFMASH™ BG, DELTAZYM® GA L-E5 glucoamylase, SPIRIZYME® Excel Plus, DISTALLASE® XP, DISTALLASE® CS, DISTILLASE® CS WB, DISTILLASE® SSF, DISTILLASE® SSF+, GLUCOAMYL™ L 209, GLUCOAMYL™ L-209+, GLUCOAMYL™ L-561, SPIRIZYME® Ultra XHS, SPIRIZYME® Achieve, FUELTASE™, OMPTFMASH™, XYLATHIN®, and OPTFMASH™ VR, and are available from BASF, CTE Global, DuPont, Novozymes, and other suppliers.

In several embodiments, the methods comprise the addition of one or more starch-degrading or isomerizing enzymes, such as, for example, α-amylase (EC 3.2.1.1), endo or exo-1,4- or 1,6-α-D-glucoamylase, glucose isomerase, β-amylases (EC 3.2.1.2), α-glucosidases (EC 3.2.1.20), and other exo-amylases; starch debranching enzymes, such as isoamylase (EC 3.2.1.68), pullulanase (EC 3.2.1.41), neo-pullulanase, iso-pullulanase, amylopullulanase and the like; glycosyl transferases such as cyclodextrin glycosyltransferase and the like. In some embodiments, the amylase is present in an amount of from about 0.001 to about 0.2 wt % (e.g., 0.001%, 0.005%, 0.01%, 0.03%, 0.05%, 0.07%, 0.09%, 0.1%, 0.11%, 0.13%, 0.15%, 0.17%, 0.19%, 0.2% and ranges in between). In several embodiments, the methods comprise the addition of one or more enzymes that can facilitate the release of starch from plant tissue, including, but not limited to, cellulases, such as exo-1,4-β-cellobiohydrolase (EC 3.2.1.91), exo-1,313-D-glucanase (EC 3.2.1.39), hemicellulase, β-glucosidase and the like; endo-glucanases such as endo-1,3-β-glucanase (EC 3.2.1.6) and endo-1,4-β-glucanase (EC 3.2.1.4) and the like; L-arabinases, such as endo-1,5-α-L-arabinase (EC EC 3.2.1.99), α-arabinosidases (EC 3.2.1.55) and the like; galactanases such as endo-1,4-β-D-galactanase (EC 3.2.1.89), endo-1,3-β-D-galactanase (EC 3.2.1.90), 1-galactosidase, α-galactosidase and the like; mannanases, such as endo-1,413-D-mannanase (EC 3.2.1.78), β-mannosidase (EC 3.2.1.25), α-mannosidase (EC 3.2.1.24) and the like; xylanases, such as endo-1,4-1-xylanase (EC 3.2.1.8), β-D-xylosidase (EC 3.2.1.37), 1,3-β-D-xylanase, and the like; pectinases and phytases.

In several embodiments, the amylase is an alpha amylase, a beta amylase, a gamma amylase. As used herein, the term "α-amylase" shall be given its ordinary meaning and shall also refer to an enzyme which cleaves or hydrolyzes internal a (1-4) glycosidic bonds in starch, resulting in smaller molecular weight maltodextrins. These smaller molecular weight maltodextrins include, but are not limited to, maltose, which is a disaccharide (i.e., a dextrin with a degree of polymerization of 2 or a DP2), maltotriose (a DP3), maltotetrose (a DP4), and other oligosaccharides. The enzyme α-amylase (EC 3.2.1.1) can also be referred to as 1,4-α-D-glucan glucanohydrolase or glycogenase. A variety of α-amylases are known in the art and are commercially available. An α-amylase can be from a fungal or bacterial origin and can be expressed in transgenic plants. The α-amylase can be thermostable. In some embodiments, the alpha amylase is a polypeptide or comprises a polypeptide having an amino acid sequence that has at least 70% identity to the amino acid sequence shown in SEQ ID NO:1, and in still further embodiments at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or even 100% identity to the amino acid sequence shown in any one of the amino acid sequences selected from: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, and SEQ ID NO:51.

"Sequence Identity," "% sequence identity." "% identity," or "Sequence alignment" means a comparison of a first amino acid sequence to a second amino acid sequence, or a comparison of a first nucleic acid sequence to a second nucleic acid sequence and is calculated as a percentage based on the comparison. The result of this calculation can be described as "percent identical" or "percent ID."

Generally, a sequence alignment can be used to calculate the sequence identity by one of two different approaches. In the first approach, both, mismatches at a single position and gaps at a single position are counted as non-identical positions in final sequence identity calculation. In the second approach, mismatches at a single position are counted as non-identical positions in final sequence identity calculation; however, gaps at a single position are not counted (ignored) as non-identical positions in final sequence identity calculation. In other words, in the second approach gaps are ignored in final sequence identity calculation. The differences between these two approaches, counting gaps as non-identical positions vs ignoring gaps, at a single position can lead to variability in sequence identity value between two sequences.

In an embodiment of this disclosure, sequence identity is determined by a program, which produces an alignment, and calculates identity counting both mismatches at a single position and gaps at a single position as non-identical positions in final sequence identity calculation. For example program Needle (EMBOS), which has implemented the algorithm of Needleman and Wunsch (Needleman and Wunsch, 1970, J. Mol. Biol. 48: 443-453), and which calculates sequence identity by first producing an alignment between a first sequence and a second sequence, then counting the number of identical positions over the length of the alignment, then dividing the number of identical residues by the length of an alignment, then multiplying this number by 100 to generate the % sequence identity [% sequence identity=(# of Identical residues/length of alignment)×100)].

In another embodiment of this disclosure, sequence identity can be calculated from a pairwise alignment showing both sequences over the full length, so showing the first sequence and the second sequence in their full length ("Global sequence identity"). For example, program Needle (EMBOSS) produces such alignments; % sequence identity=(# of identical residues/length of alignment)×100)].

In another embodiment of this disclosure, sequence identity can be calculated from a pairwise alignment showing only a local region of the first sequence or the second sequence ("Local Identity"). For example, program Blast (NCBI) produces such alignments; % sequence identity=(# of Identical residues/length of alignment)×100)].

In another embodiment, a sequence alignment is calculated with mismatches at a single position are counted as non-identical positions in final sequence identity calculation; however, gaps at a single position are not counted (ignored) as non-identical positions in final sequence identity calculation.

In a preferred embodiment the sequence alignment is generated by using the algorithm of Needleman and Wunsch (J. Mol. Biol. (1979) 48, p. 443-453). Preferably, the program "NEEDLE" (The European Molecular Biology Open Software Suite (EMBOSS)) is used for the purposes of the current invention, with using the programs default parameter (gap open=10.0, gap extend=0.5 and matrix=EBLOSUM62). Then, a sequence identity can be calculated from the alignment showing both sequences over the full length, so showing the first sequence and the second sequence in their full length ("Global sequence identity"). For example, % sequence identity=(# of identical residues/length of alignment)×100)].

In another preferred embodiment the preferred alignment program is "NEEDLE" with using the programs default parameter (gap open=10.0, gap extend=0.5 and matrix=EDNAFULL). In several embodiments, the α-amylase is selected from Novozyme Avantec, Syngenta Enogen Corn, Novozyme Liquozyme LpH, DuPont SPEZYME RSL, DuPont HT, DuPont CL, Novozyme Liquozyme SCDS, and Novozyme Avantec Amp. In some embodiments, the alpha amylase is selected from the group consisting of Liquozyme® SC, Termamyl® SC, Fuelzyme® LF, Veretase, Liqozyme® SC4x, Liquozyme® Supra 2.8, Liquozyme® supra 2, Liquozyme® X, Termamyl® 120L, SPEZYME® ALPHA, SPEZYME® CL, Clearflow® AA, Optitherm™ and Takatherm™, Keistase™, an alpha-amylase from *B. subtilis*, an alpha-amylase from *B. stearothermophilus*, an alpha-amylase from *B. lentus*, an alpha-amylase from *B. licheniformis*, an alpha-amylase from *B. coagulans*, an alpha-amylase from *B. amyloliquefaciens*, an alpha-amylase from an *Aspergillus* species, an alpha-amylase from a *Trichoderma* species, an alpha-amylase from *Rhizopus* species, an alpha-amylase from a *Mucor* species, or an alpha-amylase from a *Penicillium* species.

EXAMPLES

Example 1: Investigation of Surfactant Impact on Slurry Viscosity

The impact of the following surfactants on slurry viscosity was assayed in this study: XP50, XP70, XP90, XL50, XL70, XL90, A03, A08, EO/Alkyl Sulfate 115, EO/Alkyl Sulfate 121, Agnique SB030, Agnique CS030, Tetronic 1304, L61, 31R1, L101, P104, A65N, A9N, Alkyl Sulfate C8, Alkyl Sulfate C12, Alkyl Sulfate C18, T-MAZ 80, T-MAZ 85, Gemini 8EO, and Gemini 18EO.

Peak viscosity measurements were conducted as follows. First, corn flour, water, an alpha amylase (SEQ ID NO:1), and diluted surfactant were mixed at 300 rpm at room temperature for 10 minutes (see Table 1). Second, the sample mixture was added to a rheometer for viscosity measurement. The temperature was increased to 75° C. (which took about 9 minutes) and held at that temperature for 30 minutes. The peak viscosity was compared to the control (no surfactant addition). FIG. 1 depicts the impact of the assayed surfactants on viscosity.

TABLE 1

| 0.01% SURFACTANT FORMULATION | |
|---|---|
| Component | Mass (g) |
| 0.1% Surfactant Solution | 0.4750 |
| Water | 13.7742 |
| Corn Flour | 4.7500 |
| Alpha-amylase (SEQ ID: 1) | $7.5 \times 10^{-4}$ (0.755 μl) |

Example 2: Synthetic Media Study of Surfactant Impact

The impact of the surfactants and surfactant blends depicted in Table 2 on ethanol production were assayed.

TABLE 2

| SURFACTANTS AND SURFACTANT BLENDS | | | | |
|---|---|---|---|---|
| | Surfactant 1 | Surfactant 2 | Surfactant 1 dose (w/v %) | Surfactant 2 dose (w/v %) |
| Control | | | | |
| T-MAZ85 | T-MAZ85 | NA | 0.0003% | NA |
| Tetronic 1304 | Tetronic 1304 | NA | 0.0003% | NA |
| Agnique SBO 30 | Agnique SBO 30 | NA | 0.0029% | NA |
| Lutensol A03 | Lutensol A03 | NA | 0.0029% | NA |
| Lutensol A08 | Lutensol A08 | NA | 0.0003% | NA |
| Lutensol A65N-dose 1 | Lutensol A65N-dose 1 | NA | 0.0291% | NA |
| Lutensol A65N-dose 2 | Lutensol A65N-dose 2 | NA | 0.0029% | NA |
| Lutensol A9N-dose 1 | Lutensol A9N-dose 1 | NA | 0.0291% | NA |
| Lutensol A9N-dose 2 | Lutensol A9N-dose 2 | NA | 0.0029% | NA |
| XP 90/L61 | Pluronic L61 | Lutensol XP90 | 0.0029% | 0.00012% |
| XP 90/Tetronic 1304 | Tetronic 1304 | Lutensol XP90 | 0.0029% | 0.00012% |
| XP 90/T-MAZ 85 | T-MAZ 85 | Lutensol XP90 | 0.0003% | 0.00012% |
| XP 90/A03 | Lutensol A03 | Lutensol XP90 | 0.0029% | 0.00012% |
| XP 90/A65N | Lutensol A65N | Lutensol XP90 | 0.0029% | 0.00012% |
| XP 90/A9N | Lutensol A9N | Lutensol XP90 | 0.0029% | 0.00012% |
| XP 90/Agnique SBO 30 | Agnique SBO 30 | Lutensol XP90 | 0.0029% | 0.00012% |

Figure 3:
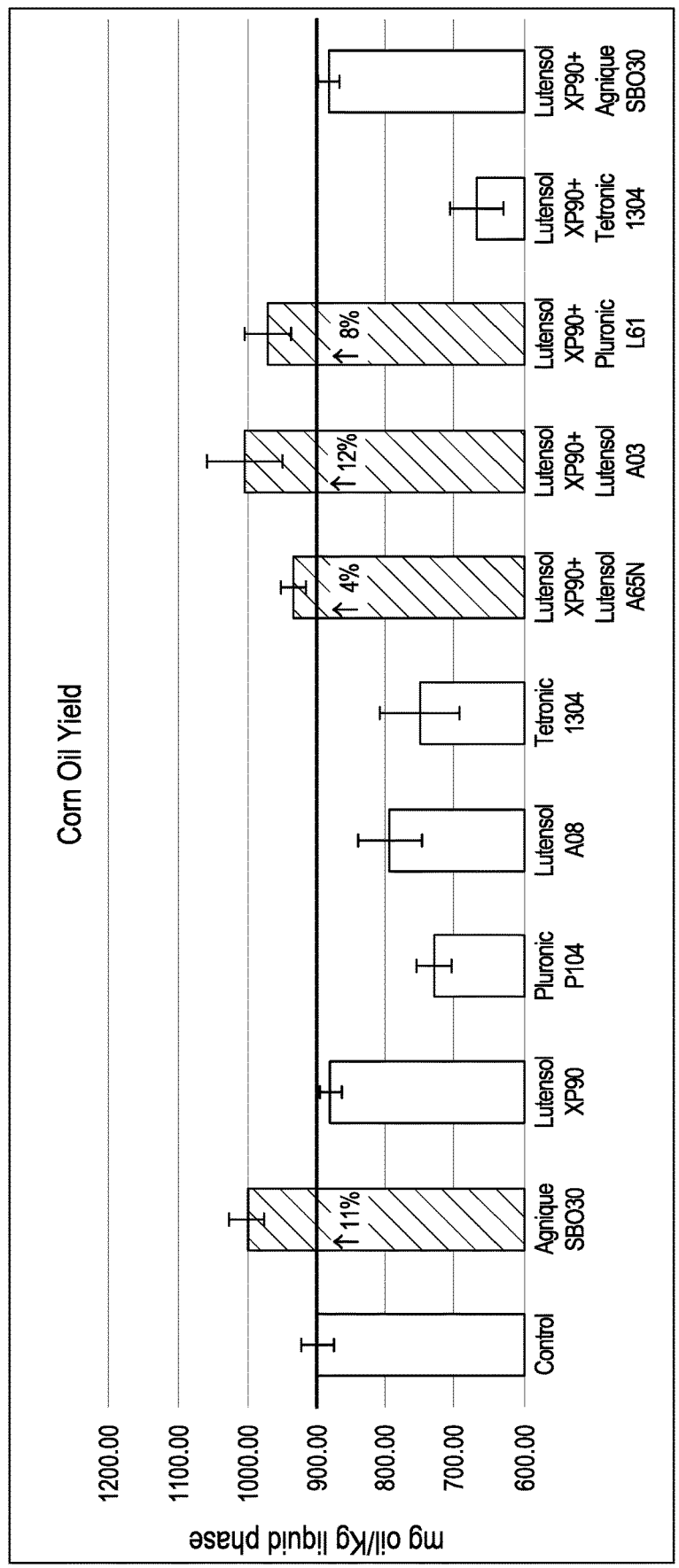
FIG. 3 depicts the impact of the indicated surfactants and surfactant blends on corn oil yield.
Figure 4:
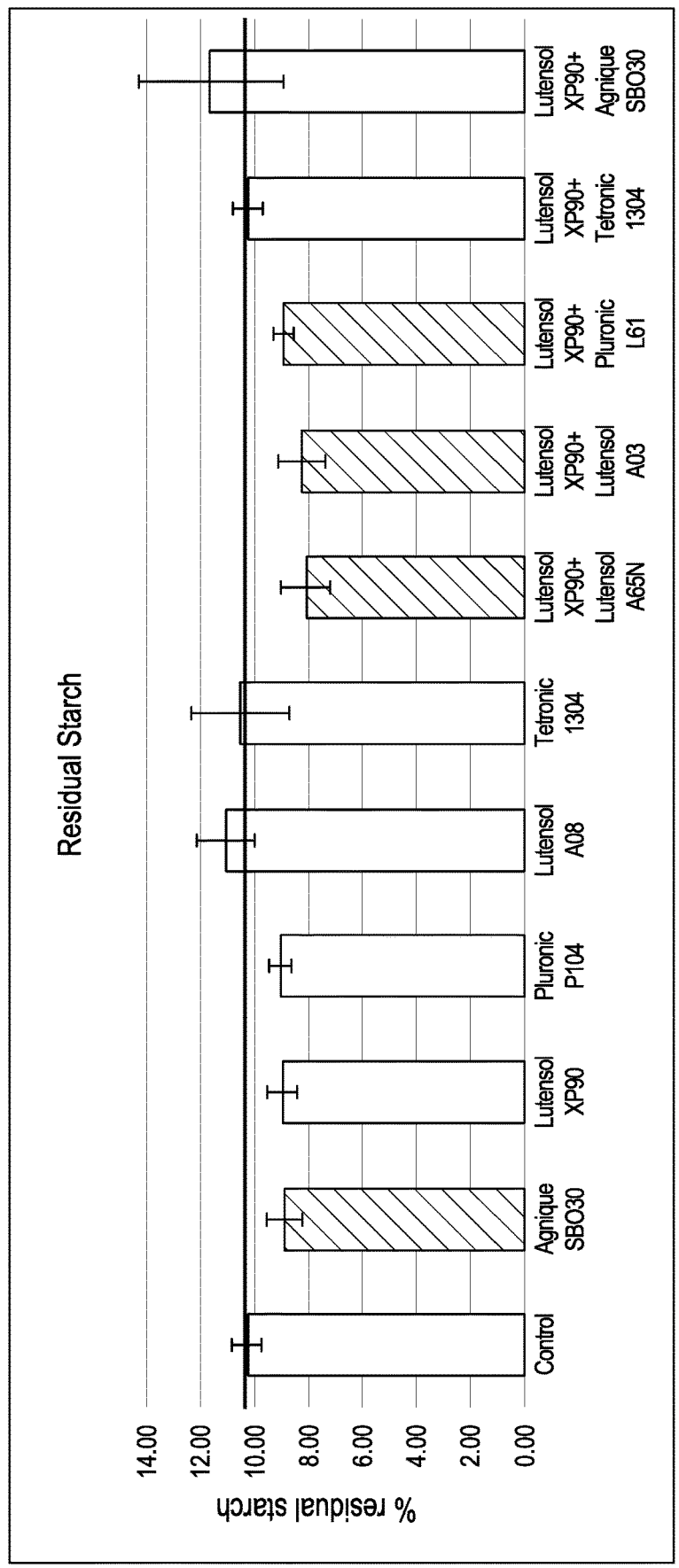
FIG. 4 depicts the impact of the indicated surfactants and surfactant blends on residual starch.

Rehydrated yeast were prepared by mixing 1.37 g of dry yeast with 169.63 mL of sterile water in a 250 mL flask, followed by incubation at 35° C. for 15 minutes at 100 rpm. The following components were then added to 250 mL shake flasks: 75 mL YPD (100 g/L glucose); surfactant (diluted); and 4.5 mL of rehydrated yeast (Ethanol Red). The shake flasks were incubated at 30° C., 100 rpm with airlock.

yeast at 35° C. for 15-30 minutes at 100 rpm. FIGS. 3 and 4 depict the impact of the candidate surfactants on corn oil yield and residual starch, respectively. Selected surfactants showed enhanced corn oil yield and low residual starch, in particular Agnique SB030, Lutensol XP90+Lutensol A65N, Lutensol XP90+Lutensol A03, and Lutensol XP90+Pluronic L61.

TABLE 3

SURFACTANT SOLUTIONS

| Name | Surfactant 1 | % dose (w/w) Surfactant 1 | Surfactant 2 | % dose (w/w) Surfactant 2 | % stock Solution Surfactant 1 | Surfactant 1 Dose (g) per Reaction | Volume of Surfactant 1 Stock (µL) | % stock Solution Surfactant 2 | Surfactant 2 Dose (g) per Reaction | Volume of Surfactant 2 Stock (µL) | Water (µL) |
|---|---|---|---|---|---|---|---|---|---|---|---|
| Control | NA | | NA | | | | | | | | 396 |
| Agnique SBO30 | | | Agnique SBO30 | 0.01% | | | | 1% | 0.0036 | 360 | 36 |
| Lutensol XP90 | | | Lutensol XP90 | 0.0001% | | | | 0.1% | 0.000036 | 36 | 360 |
| Pluronic P104 | | | Pluronic P104 | 0.01% | | | | 1% | 0.0036 | 360 | 36 |
| Lutensol A08 | | | Lutensol A08 | 0.0001% | | | | 0.1% | 0.000036 | 36 | 360 |
| Tetronic 1304 | | | Tetronic 1304 | 0.001% | | | | 1% | 0.00036 | 36 | 360 |
| Lutensol XP90 + Lutensol A65N | Lutensol XP90 | 0.0001% | Lutensol A65N | 0.01% | 0.1% | 0.000036 | 36 | 1% | 0.0036 | 360 | 0 |
| Lutensol XP90 + Lutensol A03 | Lutensol XP90 | 0.0001% | Lutensol A03 | 0.01% | 0.1% | 0.000036 | 36 | 1% | 0.0036 | 360 | 0 |
| Lutensol XP90 + Pluronic L61 | Lutensol XP90 | 0.0001% | Pluronic L61 | 0.01% | 0.1% | 0.000036 | 36 | 1% | 0.0036 | 360 | 0 |
| Lutensol XP90 + Tetronic 1304 | Lutensol XP90 | 0.0001% | Tetronic 1304 | 0.01% | 0.1% | 0.000036 | 36 | 1% | 0.0036 | 360 | 0 |
| Lutensol XP90 + Agnique SBO30 | Lutensol XP90 | 0.0001% | Agnique SBO30 | 0.01% | 0.1% | 0.000036 | 36 | 1% | 0.0036 | 360 | 0 |

Figure 2:
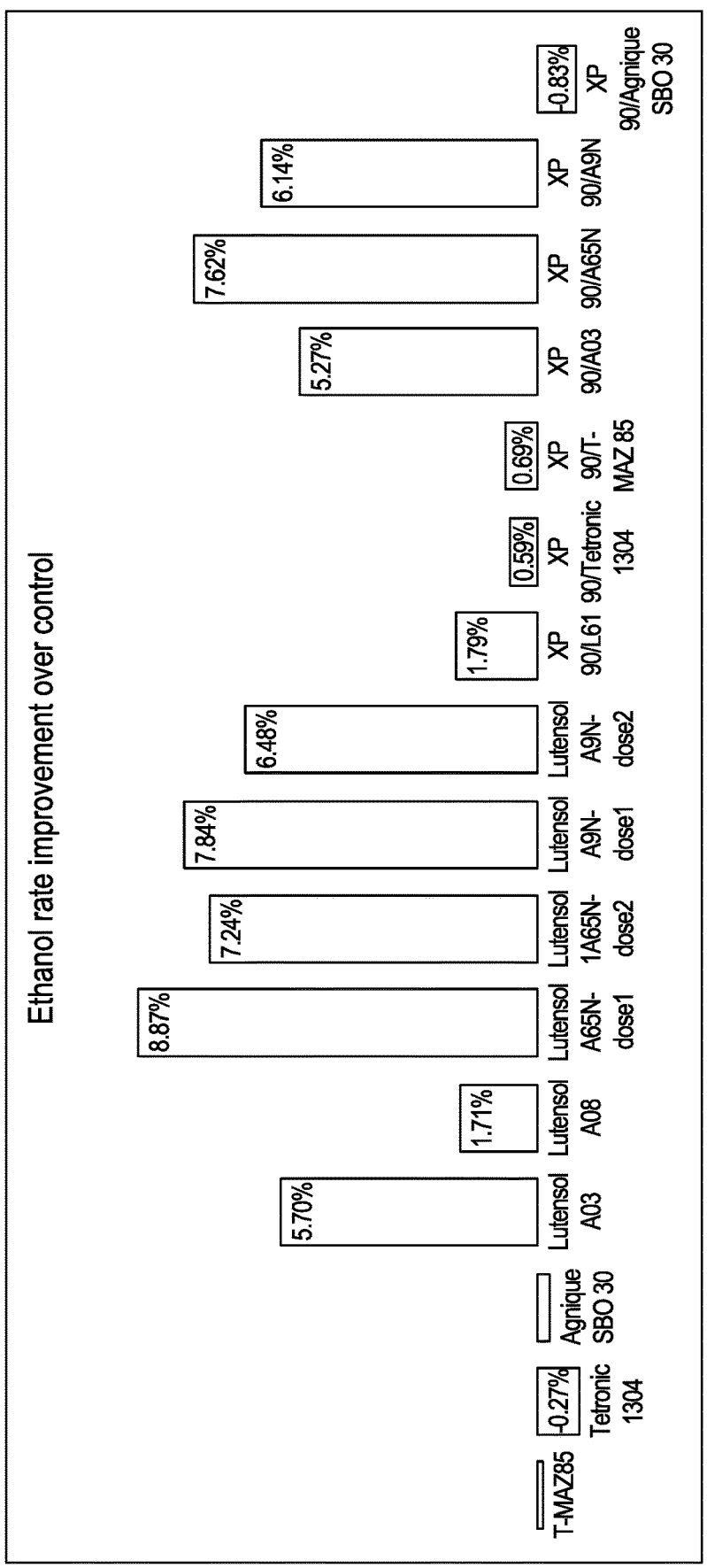
FIG. 2 depicts the impact of the indicated surfactants and surfactant blends on fermentation rate.

Samples were taken at 14 hour and 20 hour time points. GC analysis of ethanol titer of the samples was performed, with the samples compared against the control (no surfactant addition) (FIG. 2). Additionally, HPLC analysis of the sugar profile of selected samples was performed as a confirmation of GC data.

Example 3: Bench Scale Application Study of Candidate Surfactants and Surfactant Blends The top 10 surfactants and surfactant blends screened in Examples 1 and 2 (and depicted in Table 3) were chosen for further examination in a bench scale application study.

Four beakers assayed per condition, and pooled into a bottle after liquefaction. The liquefaction set up (pH was adjusted to pH5.0 with sulfuric acid) included the following: 39.91 g of milled corn (% solid=90.21%); 80.09 g of water; 0.00792 g of alpha-amylase (SEQ ID NO:1); and the surfactant solution indicated in Table 3. Each of the surfactants were added separately, with an alpha-amylase dose of 0.022% (w/w dry basis) selected based on current average usage at commercial scale. Liquefaction comprised the following steps: step 1, 75° C. for 20 minutes; step 2, 102° C. for 8 minutes; and step 3, 90° C. for 120 minutes. Following liquefaction, simultaneous saccharification and fermentation performed by incubating a 500 mL shake flask [containing 150 g of liquefied corn mash, 9 g of rehydrated yeast, 0.441 g of 40% urea (w/v), 0.047 g Glucoamylase (Deltazym GA) and 0.009 g tetracycline (20 mg/ml)] at 30° C. shaking 150 rpm with air lock for 65 hours. Yeast rehydration was performed by mixing 1.869 g of dry yeast and 232.13 g of sterile water, followed by conditioning the In at least some of the previously described embodiments, one or more elements used in one embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

All references cited herein, including patents, patent applications, papers, text books, and the like, and the references cited herein, to the extent that they are not already, are hereby incorporated by reference in their entirety. In the event that one or more of the incorporated literature and similar materials differ from or contradict this application, including but not limited to defined terms, term usage, described techniques, or the like, this application controls.

What is claimed is:

1. A method of starch processing in the production of a fermentation product, comprising the steps of:
   (a) providing an alpha amylase;
   (b) providing at least one surfactant selected from alcohol alkoxylates, alkylphenol ethoxylates, block copolymers of EO/PO, block copolymers of ethylene diamine, alkyl polyglycosides, glycerol esters, polyethylene glycol esters, functionalized polyols, sorbitan esters, ethoxylated sorbitan esters, alkoxylated sorbitan esters, natural oil alkoxylates, polyoxyalkylene glycols, and any combination thereof;
   (c) adding (a) and (b) to a slurry tank comprising a slurry having a starch; wherein the viscosity of the slurry is reduced by at least 3% compared to a slurry not comprising the surfactant of (b); and
   (d) saccharifying and fermenting the slurry of step (c) to produce a fermentation product selected from the group consisting of alcohols, acids, ketones, amino acids, antibiotics, enzymes, vitamins, hormones, and any combination thereof;
   wherein the alpha amylase is a polypeptide comprising an amino acid sequence at least 85% identical to any one of the amino acid sequences of SEQ ID NO:1 to SEQ ID NO: 5.

2. The method of claim 1, wherein (a) and (b) are added to the slurry tank during a preliquefying stage; a gelatinizing stage, a liquefying stage, or any combination thereof.

3. A method of starch processing in the production of a fermentation product, comprising the steps of:
   (a) providing an alpha amylase;
   (b) providing at least one surfactant selected from alcohol alkoxylates, alkylphenol ethoxylates, block copolymers of EO/PO, block copolymers of ethylene diamine, alkyl polyglycosides, glycerol esters, polyethylene glycol esters, functionalized polyols, sorbitan esters, ethoxylated sorbitan esters, alkoxylated sorbitan esters, natural oil alkoxylates, polyoxyalkylene glycols, and any combination thereof;
   (c) adding (a) and (b) to a liquefaction tank comprising a slurry having a starch; wherein the viscosity of the slurry is reduced by at least 3% compared to a slurry not comprising the surfactant of (b); and (d) saccharifying and fermenting the slurry of step (c) to produce a fermentation product selected from the group consisting of alcohols, acids, ketones, amino acids, antibiotics, enzymes, vitamins, hormones, and any combination thereof;

wherein the alpha amylase is a polypeptide comprising an amino acid sequence at least 85% identical to any one of the amino acid sequences of SEQ ID NO:1 to SEQ ID NO: 5.

4. The method of claim 1 or 3, further comprising recovering the fermentation product, wherein the fermentation product is ethanol, wherein the yield of ethanol production is increased, the rate of ethanol production is increased, or both the yield and the rate of ethanol production is increased.

5. The method of claim 1 or 3, wherein the fermentation is performed in the presence of a microorganism, wherein the microorganism is a bacterial species, a yeast species, a fungal species, or any combination thereof, and wherein the fermentation rate is increased by at least 5% compared to a slurry not treated with the one or more surfactants.

6. The method of claim 5 further comprising adding a surfactant to a stillage, a separator, a corn oil extraction, or any combination thereof, wherein the stillage is a whole stillage, a thin stillage, a wet cake, a syrup, or any combination thereof.

7. The method of claim 6, wherein the preliquefaction is performed at a temperature of 60° C. to 95° C., and wherein preliquefaction is performed for a period of 5 minutes to 60 minutes.

8. The method of claim 7, wherein gelatinizing stage comprises jet cooking, wherein the jet cooking is performed at a temperature of 95° C. to 140° C., and wherein the jet cooking is performed for a period of 1 minutes to 15 minutes.

9. The method of claim 8, wherein liquefaction is performed at a temperature of 60° C. to 95° C., and wherein the liquefaction is performed for a period of 20 minutes to 200 minutes.

10. The method of claim 9, wherein one or more of steps (a), (b), and (c) is performed in the presence of one or more additional enzymes, wherein the at least one of the one or more additional enzymes is present in an amount of from 0.001 to 0.2 wt %, and wherein the one or more additional enzymes comprises an enzyme selected from the group consisting of a phytase, cellulase, protease, aminopeptidase, amylase, beta-amylase, carbohydrase, carboxypeptidase, catalase, chitinase, cutinase, cyclodextrin glucanotransferase, deoxyribonuclease, esterase, α-galactosidase, β-galactosidase, glucoamylase, a-glucosidase, β-glucosidase, haloperoxidase, invertase, isomerase, laccase, lipase, mannosidase, oxidase, pectinase, peptidoglutaminase, peroxidase, polyphenoloxidase, nuclease, ribonuclease, transglutaminase, xylanase, pullulanase, isoamylase, carrageenase, protease, and any combination thereof.

11. The method of claim 10, wherein the amylase is present in an amount of from 0.001 to 0.2 wt %, and wherein the amylase comprises an alpha amylase, a beta amylase, a gamma amylase, or any combination thereof.

12. The method of claim 11, wherein the method comprises distilling a beer to produce ethanol and whole stillage, wherein the whole stillage is processed to produce one or more of wet distiller's grains with solubles (WDGS), dried distiller's grains with solubles (DDGS), and corn oil.

13. The method of claim 12, wherein the corn oil yield is increased by at least 5% compared to a slurry not treated with one or more surfactants.

14. The method of claim 1, wherein the amount of residual starch is reduced by at least 5% compared to a comparable method performed in the absence of said one or more surfactants.

15. The method of claim 12, wherein components of the slurry are not separated and reconstituted.

16. The method of claim 15, wherein the method does not comprise adding an acid to the slurry, wherein the acid is or comprises methanesulfonic acid, sulfuric acid, hydrochloric acid, acetic acid, tartaric acid, lactic acid, citric acid, an alkanesulfonic, or any combination thereof.

17. The method of claim 16, wherein the viscosity of the slurry is less than 200 centipoise.

18. The method of claim 17, wherein the pH of the slurry is not adjusted.

19. The method of claim 17, wherein said one or more surfactants has hydrophilic-lipophilic balance (HLB) value of greater than 5.

* * * * *